(12) United States Patent
McKnight et al.

(10) Patent No.: US 9,701,676 B2
(45) Date of Patent: Jul. 11, 2017

(54) PRO-NEUROGENIC COMPOUNDS

(71) Applicant: Board of Regents of The University of Texas System, Austin, TX (US)

(72) Inventors: Steven L. McKnight, Dallas, TX (US); Andrew A. Pieper, Iowa City, IA (US); Joseph M. Ready, Carrollton, TX (US); Enrique Fernandez, Dallas, TX (US)

(73) Assignee: Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 13/974,642

(22) Filed: Aug. 23, 2013

(65) Prior Publication Data

US 2014/0057900 A1  Feb. 27, 2014

Related U.S. Application Data

(60) Provisional application No. 61/693,108, filed on Aug. 24, 2012.

(51) Int. Cl.

| | | |
|---|---|---|
| *A61K 31/403* | (2006.01) | |
| *C07D 209/82* | (2006.01) | |
| *C07D 209/86* | (2006.01) | |
| *C07D 209/88* | (2006.01) | |
| *C07D 471/04* | (2006.01) | |
| *C07D 223/24* | (2006.01) | |
| *C07D 487/04* | (2006.01) | |
| *C07D 209/90* | (2006.01) | |
| *C07D 405/06* | (2006.01) | |
| *C07D 403/06* | (2006.01) | |
| *A61K 31/55* | (2006.01) | |
| *A61K 31/519* | (2006.01) | |

(52) U.S. Cl.
CPC .......... *C07D 471/04* (2013.01); *A61K 31/403* (2013.01); *A61K 31/519* (2013.01); *A61K 31/55* (2013.01); *C07D 209/90* (2013.01); *C07D 223/24* (2013.01); *C07D 403/06* (2013.01); *C07D 405/06* (2013.01); *C07D 487/04* (2013.01)

(58) Field of Classification Search
CPC .. A61K 31/403; C07D 209/82; C07D 209/86; C07D 209/88
USPC .................. 514/411; 548/440, 444
See application file for complete search history.

(56) References Cited

U.S. PATENT DOCUMENTS

| | | |
|---|---|---|
| 3,409,628 A | 11/1968 | Berger et al. |
| 3,518,250 A | 6/1970 | Schumaker |
| 4,495,281 A | 1/1985 | Buckler et al. |
| 5,234,923 A | 8/1993 | Poss et al. |
| 5,306,609 A | 4/1994 | Mihayashi et al. |
| 6,187,785 B1 | 2/2001 | Zefirov et al. |
| 6,468,996 B1 | 10/2002 | Jeppesen et al. |
| 6,514,968 B1 | 2/2003 | TenBrink |
| 6,569,849 B1 | 5/2003 | Jorgensen et al. |
| 6,770,656 B2 | 8/2004 | Halazy et al. |
| 6,835,513 B2 | 12/2004 | Jubran et al. |
| 6,849,640 B2 | 2/2005 | Ennis et al. |
| 6,864,025 B2 | 3/2005 | Law et al. |
| 7,018,988 B2 | 3/2006 | Halazy et al. |
| 7,071,206 B2 | 7/2006 | Zefirov et al. |
| 7,148,259 B1 | 12/2006 | Li et al. |
| 7,438,916 B2 | 10/2008 | Rathore et al. |
| 7,445,877 B2 | 11/2008 | Jubran et al. |
| 7,449,478 B2 | 11/2008 | Hsieh et al. |
| 7,807,704 B2 | 10/2010 | Thomas et al. |
| 7,834,063 B2 | 11/2010 | Turnbull et al. |
| 7,989,127 B2 | 8/2011 | Wu et al. |
| 8,362,277 B2 | 1/2013 | McKnight et al. |
| 8,604,074 B2 | 12/2013 | McKnight et al. |
| 8,735,440 B2 | 5/2014 | McKnight et al. |
| 8,748,473 B2 | 6/2014 | McKnight et al. |
| 8,791,149 B2 | 7/2014 | McKnight et al. |
| 8,877,797 B2 | 11/2014 | McKnight et al. |

(Continued)

FOREIGN PATENT DOCUMENTS

| | | |
|---|---|---|
| CN | 101139347 A | 3/2008 |
| CN | 101429198 A | 5/2009 |

(Continued)

OTHER PUBLICATIONS

AsInEx Chemical Library, Compound "9H-Carbazole-9-Ethanol, 3, 6-dibromo-a-[[(3-chlorophenyl) amino] methyl]" (2001).
Bradshaw et al., The Development of the Antitumour Benzothiazole Prodrug, Phortress, as a Clinical Candidate, Current Medicinal Chemistry 11, pp. 1-13 (pp. 1241-1253) 2004; (retrieved from the Internet) http://www.pharminox.com/pdf/Phortess_rev.pdf.
Certain STN chemicals, entry date ranging from Nov. 6, 2000 to May 19, 2009 (47 pages).
Kemp et al., "Pharmacologic Rescue of Motor and Sensory Function by the Neuroprotective Compound P7C3 Following Neonatal Nerve Injury," Neuroscience (2015), 284, 202-216.

(Continued)

*Primary Examiner* — Brenda Coleman
(74) *Attorney, Agent, or Firm* — Greenberg Traurig, LLP; David J. Dykeman; Fang Xie

(57) ABSTRACT

Compounds and methods for stimulating neurogenesis (e.g., post-natal neurogenesis, including post-natal hippocampal and hypothalamic neurogenesis) and/or protecting neuronal cell from cell death are disclosed herein. In vivo activity tests suggest that these compounds may have therapeutic benefits in neuropsychiatric and/or neurodegenerative diseases such as schizophrenia, major depression, bipolar disorder, normal aging, epilepsy, traumatic brain injury, post-traumatic stress disorder, Parkinson's disease, Alzheimer's disease, Down syndrome, spinocerebellar ataxia, amyotrophic lateral sclerosis, Huntington's disease, stroke, radiation therapy, chronic stress, abuse of a neuro-active drug, retinal degeneration, spinal cord injury, peripheral nerve injury, physiological weight loss associated with various conditions, as well as cognitive decline associated with normal aging, chemotherapy, and the like.

14 Claims, No Drawings

(56) References Cited

U.S. PATENT DOCUMENTS

| | | |
|---|---|---|
| 9,095,571 B2 | 8/2015 | McKnight et al. |
| 9,095,572 B2 | 8/2015 | McKnight et al. |
| 9,156,787 B2 | 10/2015 | McKnight et al. |
| 9,162,980 B2 | 10/2015 | McKnight et al. |
| 9,243,281 B2 | 1/2016 | McKnight et al. |
| 9,278,923 B2 | 3/2016 | McKnight et al. |
| 2003/0171309 A1 | 9/2003 | Halazy et al. |
| 2003/0203296 A1 | 10/2003 | Law et al. |
| 2003/0207188 A1 | 11/2003 | Jubran et al. |
| 2003/0216427 A1 | 11/2003 | Halazy et al. |
| 2005/0124675 A1 | 6/2005 | Hsieh et al. |
| 2005/0277038 A1 | 12/2005 | Jubran et al. |
| 2006/0038170 A1 | 2/2006 | Brunschwiler et al. |
| 2007/0185152 A1 | 8/2007 | Yamashita et al. |
| 2007/0196395 A1 | 8/2007 | Mackerell et al. |
| 2007/0197524 A1 | 8/2007 | Brauer et al. |
| 2007/0203236 A1 | 8/2007 | Smith et al. |
| 2007/0275965 A1 | 11/2007 | Thomas et al. |
| 2007/0293558 A1 | 12/2007 | Gao et al. |
| 2008/0039629 A1 | 2/2008 | Ramesh et al. |
| 2008/0058383 A1 | 3/2008 | Jernstedt et al. |
| 2008/0255124 A1 | 10/2008 | Turnbull et al. |
| 2009/0137420 A1 | 5/2009 | VonHoff et al. |
| 2009/0143376 A1 | 6/2009 | Milburn et al. |
| 2009/0163545 A1 | 6/2009 | Goldfarb |
| 2009/0236229 A1 | 9/2009 | Advincula |
| 2010/0022580 A1 | 1/2010 | Hung et al. |
| 2010/0305121 A1 | 12/2010 | Smith et al. |
| 2011/0003836 A1 | 1/2011 | McKnight et al. |
| 2011/0015217 A1 | 1/2011 | McKnight et al. |
| 2012/0022096 A1 | 1/2012 | McKnight et al. |
| 2013/0040977 A1 | 2/2013 | McKnight et al. |
| 2013/0096181 A1 | 4/2013 | Ashkenazi et al. |
| 2013/0184271 A1 | 7/2013 | McKnight et al. |
| 2013/0184300 A1 | 7/2013 | McKnight et al. |
| 2013/0184301 A1 | 7/2013 | McKnight et al. |
| 2013/0190273 A1 | 7/2013 | McKnight et al. |
| 2013/0190339 A1 | 7/2013 | McKnight et al. |
| 2014/0094480 A1 | 4/2014 | McKnight et al. |
| 2014/0343018 A1 | 11/2014 | McKnight et al. |
| 2015/0057301 A1 | 2/2015 | McKnight et al. |
| 2015/0132783 A1 | 5/2015 | McKnight et al. |
| 2015/0290195 A1 | 10/2015 | McKnight et al. |
| 2016/0074361 A1 | 3/2016 | McKnight et al. |

FOREIGN PATENT DOCUMENTS

| | | |
|---|---|---|
| EP | 1 094 063 | 4/2001 |
| EP | 1 591 511 | 11/2005 |
| FR | 1167510 | 11/1958 |
| GB | 2 355 659 | 5/2001 |
| JP | H04-217657 A | 8/1992 |
| JP | 2007/223916 | 9/2007 |
| WO | WO 92/21660 | 12/1992 |
| WO | WO 96/34863 | 11/1996 |
| WO | WO 00/23425 | 4/2000 |
| WO | WO 00/78795 | 12/2000 |
| WO | WO 01/29028 | 4/2001 |
| WO | WO 01/71430 | 9/2001 |
| WO | WO 02/38142 | 5/2002 |
| WO | WO 02/060867 | 8/2002 |
| WO | WO 03/007069 | 1/2003 |
| WO | WO 03/007070 | 1/2003 |
| WO | WO 03/007071 | 1/2003 |
| WO | WO 03/032072 | 1/2003 |
| WO | WO 03/091247 | 11/2003 |
| WO | WO 2004/052885 | 6/2004 |
| WO | WO 2004/106335 | 9/2004 |
| WO | WO 2005/055951 | 6/2005 |
| WO | WO 2005/056522 | 6/2005 |
| WO | WO 2005/074971 | 8/2005 |
| WO | WO 2007/008541 | 1/2007 |
| WO | WO 2007/041697 | 4/2007 |
| WO | WO 2007/062399 | 5/2007 |
| WO | WO 2007/079239 | 7/2007 |
| WO | WO 2007/081091 | 7/2007 |
| WO | WO 2007/087425 | 8/2007 |
| WO | WO 2007/137227 | 11/2007 |
| WO | WO 2008/021745 | 2/2008 |
| WO | WO 2008/060190 | 5/2008 |
| WO | WO 2008/115098 | 9/2008 |
| WO | WO 2008/123796 | 10/2008 |
| WO | WO 2008/123800 | 10/2008 |
| WO | WO 2008/156105 | 12/2008 |
| WO | WO 2009/040517 | 4/2009 |
| WO | WO 2009/055828 | 4/2009 |
| WO | WO 2009/094668 | 7/2009 |
| WO | 2009/120717 | 10/2009 |
| WO | WO 2010/048446 | 4/2010 |
| WO | WO 2010/051503 | 5/2010 |
| WO | WO 2010/081115 | 7/2010 |
| WO | WO 2011/019417 | 2/2011 |
| WO | 2011/038162 | 3/2011 |
| WO | WO 2011/117668 | 9/2011 |
| WO | WO 2012/006419 | 1/2012 |
| WO | WO 2014/031125 | 2/2014 |
| WO | WO 2014/031986 | 2/2014 |
| WO | 2015/035051 | 3/2015 |

OTHER PUBLICATIONS

Pieper et al., "P7C3 and an unbiased Approach to Drug Discovery for Neurodegenerative Diseases," Chem. Soc. Rev. (2014), 19: 51-59.

PubChem, Compound, 1-[(3-chlorophenyl)amino]-3-(3,6-dibromo-9H-carbazol-9-yl)propan-2-ol, 2005.

STN compounds registry Nos. 305862-95-7, 304893-66-1, 304880-74-8, 304878-30-6, 304868-62-0, 301353-98-0, 301353-96-8, 301160-69-0, 300805-47-4, 300588-31-2, 253448-99-6, 119091-28-0, 119091-27-9, 331416-70-7, 331235-98-4, 331235-97-3, 328076-93-3, 327026-16-4, 317842-35-6, 314052-83-0, 313268-34-7, 313268-19-8, 313268-17-6, and 313268-16-5, entry date Feb. 17, 1989 to Apr. 16, 2001.

STN Registry Entry 312599-43-2 entered Jan. 3, 2001.

Wang et al., "P7C3 Neuroprotective Chemicals Function by Activating the Rate-Limiting Enzyme in NAD Salvage," Cell 158, 11324-1334 (2014).

Yin et al., "P7C3 Neuroprotective Chemicals Block Axonal Degeneration and Preserve Function after Traumatic Brain Injury" Cell Reports, 8, 1-10 (2014).

PCT International Search Report based on PCT/US14/54099 dated Jan. 29, 2015.

USPTO Office Action in U.S. Appl. No. 14/100,515 mailed Feb. 12, 2015.

USPTO Office Action in U.S. Appl. No. 13/594,223 mailed Feb. 13, 2015.

Giancaspro et al., "Synthesis of Disubstituted Tetrahydrocarbazoles with Potential Antidepressive Activity," IL Farmaco, 44(5), 483-493, 1989.

Giancaspro et al., "Trypanocidal Activity of 1,2,3,4-Tetrahydrocarbazoles," Rev. Microbiol., Sao Paulo, 25(3):201-205, 1994.

Kondratov et al., "Small molecules that dramatically alter multidrug resistance phenotype by modulating the substrate specificity of P-glycoprotein," Proceedings of the National Academy of Sciences of the United States of America (2011), 98(24), 14078-14083.

Muruganantham et al., "Synthesis, anticonvulsant and antihypertensive activities of 8-substituted quinoline derivatives," Vel's College of Pharmacy, Biological & Pharmaceutical Bulletin. 27(10):1683-7 (2004).

Naumova et al., CAPLUS Abstract of: Vestsi Akademii Navuk BSSR, Seryya Khimichnykh Navuk (1988), (4), 110-111)).

Pubchem CID 981287 (deposit date Jul. 9, 2005).

Pubchem CID 2851877 (deposit date Jul. 29, 2005).

Pubchem SID 3976298 (deposit date Aug. 9, 2005).

Pubchem SID 7706058 (deposit date Sep. 26, 2005).

Ravlee et al., "Pharmacological evaluation of some new 6-amino/methyl pyridine derivatives," Chem. Pharm. Bull. 51(2): 162-170 (2003).

(56) References Cited

OTHER PUBLICATIONS

Zherebtsov et al., CAPLUS Abstract of: SU 474533, From: Otkrytiya, Izobret., Prom. Obraztsy, Tovarnye Znaki 1975, 52(23), 51-2.
USPTO Office Action in U.S. Appl. No. 13/177,981 mailed Mar. 21, 2014.
USPTO Office Action in U.S. Appl. No. 13/709,531 mailed Apr. 4, 2014.
Extended European Search Report issued in European Application No. EP 11804335 mailed on Apr. 17, 2014.
USPTO Office Action in U.S. Appl. No. 13/177,981 mailed Jun. 26, 2014.
USPTO Office Action in U.S. Appl. No. 13/594,223 mailed Jun. 26, 2014.
USPTO Office Action in U.S. Appl. No. 13/709,531 mailed Jul. 10, 2014.
Abad, J. et al., "Internal Oxidosqualenes: Determination of Absolute Configuration and Activity as Inhibitors of Purified Pig Liver Squalene Epoxidase," *J. Org. Chem.*, 60(12), pp. 3648-3656 (Jun. 1995).
Abrous, D. et al., "Adult Neurogenesis: From Precursors to Network and Physiology," *Physiol Rev*, vol. 85, pp. 523-569 (2005).
Alexander, M. et al., "A Central Strategy for Converting Natural Products into Fluorescent Probes," *ChemBioChem*, 7(3), pp. 409-416 (Mar. 2006).
Altman, J., "Are New Neurons Formed in the Brains of Adult Mammals?" *Science*, 135, pp. 1127-1128 (Mar. 1962).
Altman, J., "Autoradiographic Investigation of Cell Proliferation in the Brains of Rats and Cats," *Anat. Rec.*, 145, pp. 573-591 (Apr. 1963).
Altman, J., "Autoradiographic and Histological Evidence of Postnatal Hippocampal Neurogenesis in Rats," *J. Comp. Neur.*, 124(3), pp. 319-335 (Jun. 1965).
Altman, J., "Autoradiographic and Histological Studies of Postnatal Neurogenesis: I. A Longitudinal Investigation of the Kinetics, Migration and Transformation of Cells Incorporating Tritiated Thymidine in Neonate Rats, with Special Reference to Postnatal Neurogenesis in Some Brain Regions," *J. Comp. Neur.*, 126(3), pp. 337-389 (Mar. 1966).
Altman, J., "Autoradiographic and Histological Studies of Postnatal Neurogenesis: II. A Longitudinal Investigation of the Kinetics, Migration and Transformation of Cells Incorporating Tritiated Thymidine in Infant Rats, with Special Reference to Postnatal Neurogenesis in Some Brain Regions," *J. Comp. Neur.*, 128(4), pp. 431-473 (Dec. 1966).
Altman, J., "Autoradiographic and Histological Studies of Postnatal Neurogenesis: IV. Cell Proliferation and Migration in the Anterior Forebrain, with Special Reference to Persisting Neurogenesis in the Olfactory Bulb," *J. Comp. Neur.*, 137(4), pp. 433-457 (Dec. 1969).
Araki et al., "Increased Nuclear NAD Biosynthesis and SIRT1 Activation Prevent Axonal Degeneration" *Science* 305:1010-1013, Aug. 13, 2004.
Asso, V. et al., "α-Naphthylaminopropan-2-ol Derivatives as BACE1 Inhibitors," *ChemMedChem*, 3(10), pp. 1530-1534 (Oct. 2008).
Bachurin, S. et al., "Antihistamine Agent Dimebon as a Novel Neuroprotector and a Cognition Enhancer," *Ann. N.Y. Acad. Sci.*, 939, pp. 425-435 (Jun. 2001).
Bachurin, S. et al., "Mitochondria as a Target for Neurotoxins and Neuroprotective Agents," *Ann. N.Y. Acad. Sci.*, 993, pp. 334-344 (May 2003).
Bachurin, S. et al., "Questions and Answers: Session VII: Oxidative Stress, Mitochondria, and Approaches to Neuroprotection," *Ann. N.Y. Acad. Sci.*, 993, pp. 345-349 (May 2003).
Berg et al., "New Neuronal Growth Factors " *Ann. Rev. Neurosci.*, 7: 149-170 (Jul. 1984).
Beyer, M. et al., "Synthesis of Novel Aromatic Nitroxides as Potential DNA Intercalators. An EPR Spectroscopical and DFT Computational Study," *J. Org. Chem.*, 68(6), pp. 2209-2215 (Mar. 2003).

Boekelheide, V. et al., "Curariform Activity and Chemical Structure. VII. Some 1-Skatylisoquinoline Derivatives and a Novel Method for their Synthesis," *J. Am. Chem. Soc.*, 72(5), pp. 2134-2137 (May 1950).
Boldrini, M. et al., "Antidepressants Increase Neural Progenitor Cells in the Human Hippocampus," *Neuropsychopharmacology*, 34(11), pp. 2376-2389 (Oct. 2009).
Bombrun, A. et al., "3,6-Dibromocarbazole Piperazine Derivatives of 2-Propanol as First Inhibitors of Cytochrome c Release via Bax Channel Modulation," *J. Med. Chem.*, 46(21), pp. 4365-4368 (Oct. 2003).
Borrell-Pages, M. et al., "Huntington's Disease: From Huntington Function and Dysfunction to Therapeutic Strategies," *Cell. Mol. Life Sci.*, 63(22), pp. 2462-2660 (Nov. 2006).
Brown, J. et al., "Transient Expression of Doublecortin during Adult Neurogenesis," *The Journal of Comparative Neurology*, 467(1), pp. 1-10 (Dec. 2003).
Browne, S. et al., "The Energetics of Huntington's Disease," *Neurochemical Research*, 29(3), pp. 531-546 (Mar. 2004).
Burd, G. et al., "Ultrastructural Characterization of Synaptic Terminals Formed on Newly Generated Neurons in a Song Control Nucleus of the Adult Canary Forebrain," *The Journal of Comparative Neurology*, 240(2), pp. 143-152 (Oct. 1985).
Burns, A. et al., "Dimebon in Alzheimer's Disease: Old Drug for New Indication," *The Lancet*, 372, pp. 179-180 (Jul. 2008).
Cao, R. et al., "Synthesis, Acute Toxicities, and Antitumor Effects of Novel 9-Substituted β-Carboline Derivatives," *Bioorganic & Medicinal Chemistry*, 12(17), pp. 4613-4623 (Sep. 2004).
Cao, R. et al., "Design, Synthesis and In Vitro and In Vivo Antitumor Activities of Novel β-Carboline Derivatives," *European Journal of Medicinal Chemistry*, 40(10), pp. 991-1001 (Oct. 2005).
Cao, R. et al., "DNA Binding Properties of 9-Substituted Harmine Derivatives," *Biochemical and Biophysical Research Communications*, 338(3), pp. 1557-1563 (Dec. 2005).
Cao, R. et al., "Synthesis and Cytotoxic Activities of 1-Benzylidine Substituted β-Carboline Derivatives," *Bioorganic & Medicinal Chemistry Letters*, 18(24), pp. 6558-6561 (Dec. 2008).
Cattaneo, E. et al., "Normal Huntington Function: An Alternative Approach to Huntington's Disease," *Nature Reviews: Neuroscience*, 6, pp. 919-930 (Dec. 2005).
Carter, R. et al., "Characterization of Progressive Motor Deficits in Mice Transgenic for the Human Huntington's Disease Mutation," *The Journal of Neuroscience*, 19(8), pp. 3248-3257 (Apr. 1999).
Cha, J. et al., "Altered Brain Neurotransmitter Receptors in Transgenic Mice Expressing a Portion of an Abnormal Human Huntington Disease Gene," *Proc. Natl. Acad. Sci. USA*, 95, pp. 6480-6485 (May 1998).
Cha, J., "Transcriptional Dysregulation in Huntington's Disease," *TINS*, 23(9), pp. 387-392 (Sep. 2000).
Chakraborti, A. et al., "Lithium Bromide, an Inexpensive and Efficient Catalyst for Opening of Epoxide Rings by Amines at Room Temperature under Solvent-Free Condition," *Eur. J. Org. Chem.*, 2004(17), pp. 3597-3600 (Sep. 2004).
Cimini et al., "Expression of Peroxisome Proliferator-Activated Receptors (PPARs) and Retinoic Acid Receptors (RXRs) in Rat Cortical Neurons.", Neuroscience, vol. 130, pp. 325-337, 2005.
Davies, S. et al., "Formation of Neuronal Intranuclear Inclusions Underlies the Neurological Dysfunction in Mice Transgenic for the HD Mutation," *Cell*, 90, pp. 537-548 (Aug. 1997).
DeJesus-Cortes, H. et al., "Neuroprotective Efficacy of Aminopropyl Carbazoles in a Mouse Model of Parkinson Disease" *PNAS*, vol. 109, No. 42, pp. 17010-17015 (Oct. 16, 2012).
Distelmaier, F. et al., "Life Cell Quantification of Mitochondrial Membrane Potential at the Single Organelle Level," *Cytometry A*, 73(2), pp. 129-138 (Feb. 2008).
Di Santo, R. et al., "Design, Synthesis and QSAR Studies on N-Aryl Heteroarylisopropanolamines, a New Class of Non-Peptidic HIV-1 Protease Inhibitors," *Bioorganic & Medicinal Chemistry*, 10(8), pp. 2511-2526 (Aug. 2002).
Doody, R. et al., "Effect of Dimebon on Cognition, Activities of Daily Living, Behaviour, and Global Function in Patients with

(56) References Cited

OTHER PUBLICATIONS

Mild-to-Moderate Alzheimer's Disease: A Randomised, Double-Blind, Placebo-Controlled Study," *The Lancet*, 372, pp. 207-215 (Jul. 2008).
Doody, R. et al., "Intermittent Preventive Antimalarial Treatment in Infancy," *The Lancet*, 372, pp. 1383-1384 (Oct. 2008).
Dow, R. et al., "Identification of Tricyclic Analogs Related to Ellagic Acid as Potent/Selective Tyrosine Protein Kinase Inhibitors," *J. Med. Chem.*, 37(14), pp. 2224-2231 (Jul. 1994).
Driscoll, I. et al., "The Aging Hippocampus: A Multi-Level Analysis in the Rat," *Neuroscience*, 139(4), pp. 1173-1185 (Mar. 2006).
Enyedy et al., "Discovery of Small-Molecule Inhibitors of Bcl-2 through Structure-Based Computer Screening," *J. Med. Chem.*, 44(25), pp. 4313-4324 (Dec. 6, 2001).
Eriksson, P. et al., "Neurogenesis in the Adult Human Hippocampus," *Nature Medicine*, 4(11), pp. 1313-1317 (Nov. 1998).
Fedele, V. et al., "Neurogenesis in the R6/2 Mouse Model of Huntington's Disease is Impaired at the Level of Neurod1," *Neuroscience*, 173, pp. 76-81 (Jan. 2011).
Fernandes, H. et al., "Mitochondrial Sensitivity and Altered Calcium Handling Underlie Enhanced NMDA-Induced Apoptosis in YAC128 Model of Huntington's Diase," *The Journal of Neuroscience*, 27(50), pp. 13614-13623 (Dec. 2007).
Ferris, R.M. et al., "Rimcazole (BW 234U), a Novel Antipsychotic Agent Whose Mechanism of Action Cannot be Explained by a Direct Blockade of Postsynaptic Dopaminergic Receptors in Brain," *Drug Development Research*, 9(3), pp. 171-188 (Nov. 1986).
Freireich, E. et al., "Quantitative Comparison of Toxicity of Anticancer Agents in Mouse, Rat, Hamster, Dog, Monkey, and Man," *Cancer Chemotherapy Reports*, 50(4), pp. 219-244 (May 1966).
Gennaro, A. et al., "Remington's Pharmaceutical Sciences," *Mack Publishing Company*, 17th Edition, pp. 1418-1419 (1985).
Getautis, V. et al., "Study of the Products from Reaction of 1(2)-Aminoanthraquinones with 1-Chloro-2,3-Epoxypropane," *Chemistry of Heterocyclic Compounds*, 41(4), pp. 426-436 (Apr. 2005).
Gil, J. et al., "Asialoerythropoetin is not Effective in the R6/2 Line of Huntington's Disease Mice," *BMC Neuroscience*, 5(17), pp. 1-10 (May 2004).
Gil, J. et al., "Reduced Hippocampal Neurogenesis in R6/2 Transgenic Huntington's Disease Mice," *Neurobiology of Disease*, 20, pp. 744-751 (Jun. 2005).
Gil, J. et al., "The R6 Lines of Transgenic Mice: A Model for Screening New Therapies for Huntington's Disease," *Brain Research Reviews*, 59(2), pp. 410-431 (Mar. 2009).
Godin, J. et al., "Huntingtin is Required for Mitotic Spindle Orientation and Mammalian Neurogenesis," *Neuron*, 67, pp. 392-406 (Aug. 2010).
Goehler, H. et al., "A Protein Interaction Network links GIT1, an Enhancer of Huntingtin Aggregation, to Huntington's Disease," *Molecular Cell*, 15, pp. 853-865 (Sep. 2004).
Goldberg, Y.P. et al., "Cleavage of Huntingtin by Apopain, a Proapoptotic Cysteine Protease, is Modulated by the Poyglutamine Tract," *Nature Genetics*, 13, pp. 442-449 (Aug. 1996).
Goldman, S. et al., "Neuronal Production, Migration, and Differentiation in a Vocal Control Nucleus of the Adult Female Canary Brain," *Proc. Natl. Acad. Sci. USA*, 80, pp. 2390-2394 (Apr. 1983).
Gross, C. "Neurogenesis in the Adult Brain: Death of a Dogma," *Nature Reviews*, 1, pp. 67-73 (Oct. 2000).
Haggquist, G. et al., "Intramolecular Triplet Energy Transfer. 3. A Carbazole-Naphthalene System Having Short Chain Length Methylene Spacer Units," *J. Phys. Chem.*, 97, pp. 9270-9273 (Sep. 1993).
Harbert, C. et al., "Neuroleptic Activity in 5-Aryltetrahydro-γ-carbolines," *J. Med. Chem.*, 23(6), pp. 635-643 (Jun. 1980).
Hisada, K. et al., "Intramolecular Triplet Energy Transfer. 4. A Carbazole-Naphthalene System Having a Flexible Alkyl Spacer Doped in Poly(methyl methacrylate) Matrixes," *J. Phys. Chem. B*, 102, pp. 2640-2645 (Mar. 1998).

Jackson-Lewis, V. et al., "Protocol for the MPTP Mouse Model of Parkinson's Disease," *Nature Protocols*, 2, pp. 141-151 (Feb. 2007).
Jin, K. et al., "Heparin-Binding Epidermal Growth Factor-Like Growth Factor: Hypoxia-Inducible Expresstion In Vitro and Stimulation of Neurogenesis In Vitro and In Vivo," *The Journal of Neuroscience*, vol. 22, Chapter 13, pp. 5365-5373 (Jul. 1, 2002).
Jorapur, Y. et al., "Potassium Carbonate as a Base for the N-alkylation of Indole and Pyrrole in Ionic Liquids," *Tetrahedron Letters*, 47(14), pp. 2435-2438 (Apr. 2006).
Jun, W. et al., "Inorganic-Organic Hybrid Photorefractive Materials Bearing the Bifunctional Chromophore," *Journal of Nonlinear Optical Physics & Materials*, 14(4), pp. 497-504 (Dec. 2005).
Kaewtong, C. et al., "Self-Assembly and Electrochemical Oxidation of Pollyamidoamine—Carbazole Dendron Surfmer Complexes: Nanoring Formation," *ACS Nano*, 2(8), pp. 1533-1542 (Aug. 2008).
Kamal et al., "Carbazole-pyrrolo [2,1-c] [1, 4] benzodiazepine conjugates: design, synthesis, and biological evaluation", MedChemComm, vol. 2, No. 8, pp. 780-788 (2001).
Kamnasaran, D. et al., "Disruption of the Neuronal PAS3 Gene in a Family Affected with Schizophrenia," *J. Med. Genet.*, 40(5), pp. 325-332 (May 2003).
Kamogawa, H. et al., "Syntheses of N-Substituted Carbazoles Involving Polymerizable Terminal Vinyl Groups," *Journal of Polymer Science*, 17(1), pp. 9-18 (Jan. 1979).
Kempermann, G. et al., "More Hippocampal Neurons in Adult Mice Living in an Enriched Environment," *Nature*, 386, pp. 493-495 (Apr. 1997).
Kim, J. et al., "Mitochondrial Loss, Dysfunction and Altered Dynamics in Huntington's Disease," *Human Molecular Genetics*, 19(20), pp. 3919-3935 (Jul. 2010).
Kim, S. et al., "Treadmill Exercise Prevents Aging-Induced Failure of Memory through an Increase in Neurogenesis and Suppression of Apoptosis in Rat Hippocampus," *Experimental Gerontology*, 45(5), pp. 357-365 (May 2010).
Kim, T. et al., "Molecular Tripods Showing Fluorescence Enhancement upon Binding to Streptavidin," *Organic Letters*, 7(1). pp. 111-114 (Jan. 2005).
Kim, T. et al., "Self-Quenching Mechanism: the Influence of Quencher and Spacer on Quencher-fluorescein Probes," *Bull. Korean. Chem. Soc.*, 28(7), pp. 1221-1223 (2007).
Kohl, Z. et al., "Impaired Adult Olfactory Bulb Neurogenesis in the R6/2 Mouse Model of Huntington's Disease," *BMC Neuroscience*, 11, pp. 1-11 (Sep. 2010).
Krishnan, V. et al., "The Molecular Neurobiology of Depression," *Nature*, 455, pp. 894-902 (Oct. 2008).
Kuhn, G. et al., "Neurogenesis in the Dentate Gyrs of the Adult Rat: Age-Related Decrease of Neuronal Progenitor Proliferation," *The Journal of Neuroscience*, 16(6), pp. 2027-2033 (Mar. 1996).
Landree et al., "C75, a Fatty Acid Synthase Inhibitor, Modulates AMP-activated Protein Kinase to Alter Neuronal Energy Metabolism" *J. Biol. Chem.*, 2004, v. 279, p. 3817-3827 (Jan. 30, 2004).
Lavedan, C. et al., "Effect of a Ciliary Neurotrophic Factor Polymorphism on Schizophrenia Symptom Improvement in an Iloperidone Clinical Trial," *Pharmacogenomics*, 9(3), pp. 289-301 (Mar. 2008).
Lavedan, C. et al., "Association of the *NPAS3* Gene and Five Other Loci with Response to the Antipsychotic Iloperidone Identified in a Whole Genome Association Study," *Molecular Psychiatry*, 14(8), pp. 804-819 (Aug. 2009).
Lee, H. et al., "Structure-Activity Relationship Studies of the Chromosome Segregation Inhibitor, Incentrom A," *Bioorganic & Medicinal Chemistry Letters*, 18(6), pp. 4670-4674 (Aug. 2008).
Li, Z. et al., "Two Types of Nonlinear Optical Polyurethanes Containing the Same Isolation Groups: Syntheses, Optical Properties, and Influence of Binding Mode," *J. Phys. Chem. B*, 113, pp. 14943-14949 (Oct. 2009).
Lione, L. et al., "Selective Discrimination Learning Impairments in Mice Expressing the Human Huntington's Disease Mutation," *The Journal of Neuroscience*, 19(23), pp. 10428-10437 (Dec. 1999).
Liu, X. et al., "Induction of Apoptotic Program in Cell-Free Extracts: Requirement for dATP and Cytochrome c," *Cell*, 86, pp. 147-157 (Jul. 1996).

(56) References Cited

OTHER PUBLICATIONS

Liu et al., "Synthesis and Spectroscopic and Electrochemical Properties of TTF-Derivatized Polycarbazole", Macromolecules, vol. 41, No. 6, pp. 2045-2048 (2011).
Loo, D. et al., "Apoptosis is Inducted by β-Amyloid in Cultured Central Nervous System Neurons," Proc. Natl. Acad. Sci. USA, 90, pp. 7951-7955 (Sep. 1993).
Lygaitis, R. et al., "Synthesis and Photophysical Properties of Bipolar Low-Molar-Mass Amorphous Materials," Journal of Photochemistry and Photobiology A: Chemistry, 167(2-3), pp. 163-168 (Oct. 2004).
MacMillan, et al., "Development of Proneurogenic, Neuroprotective Small Molecules", Journal of the American Chemical Society, vol. 133, No. 5, pp. 1428-1437 (2011).
Maegawa, Y. et al., "A Useful Procedure for Diiodination of Carbazoles and Subsequent Efficient Transformation to Novel 3,6-bis(triethoxysilyl) Carbazoles Giving Mesoporous Materials," Tetrahedron Letters, 47(39), pp. 6957-6960 (Sep. 2006).
Mahapatra, et al., "A Small Molecule Which Protects Newborn Neurons", ACS Chemical Neuroscience, vol. 1, No. 9, pp. 589 (2010).
Mangialasche, F. et al., "Alzheimer's Disease: Clinical Trials and Drug Development," The Lancet, 9, pp. 702-716 (Jul. 2010).
Mangiarini, L. et al., "Exon 1 of the HD Gene with an Expanded CAG Repeat is Sufficient to Cause a Progressive Neurological Phenotype in Transgenic Mice," Cell, 87, pp. 493-506 (Nov. 1996).
Martin, D. et al., "Apoptotic Changes in the Aged Brain are Triggered by Interleukin-1β-Induced Activation of p38 and Reversed by Treatment with Eicosapentaeonic Acid," The Journal of Biological Chemistry, 277(37), pp. 34239-34246 (Sep. 2002).
Mattos et al., "Multiple Binding Modes," in 3D QSAR in Drug Design: Theory, Methods and Applications, ed. H. Kubinyi, Springer, pp. 243-244 (Dec. 31, 1993).
McGrath, J. et al., "Novel Carbazole Phenoxy-Based Methacrylates to Produce High-Refractive Index Polymers," Polymer, 47, pp. 4042-4057 (Mar. 2006).
Menalled, L. et al., "Mouse Models of Huntington's Disease," TRENDS in Pharmacological Sciences, 23(1), pp. 32-39 (Jan. 2002).
Morcuende, A. et al., "Microwave-Promoted Transformations: Fast and Chemoselective N-Acylation of Amino Alcohols Using Catalytic Amounts of Dibutyltin Oxide. Influence of the Power Output and the Nature of the Acylating Agent on the Selectivity," J. Org. Chem., 61(16), pp. 5264-5270 (Aug. 1996).
Murphy, K. et al., "Abnormal Synaptic Plasticity and Impaired Spatial Cognition in Mice Transgenic for Exon 1 of the Human Huntington's Disease Mutation," The Journal of Neuroscience, 20(13), pp. 5115-5123 (Jul. 2000).
Naidoo, J. et al., "Development of a Scalable Synthesis of P7C3-A20, a Potent Neuroprotective Agent" Tetrahedron Letters, vol. 54, pp. 4429-4431 (2013).
Negrin, C.M. et al., "In Vivo-In Vitro Study of Biodegradable Methadone Delivery Systems," Biomaterials, 22(6), pp. 563-570 (Mar. 2001).
Neitzert, H.C. et al., "Monitoring of the Initial Degradation of Oxadiazole Based Blue OLED's," Journal of Non-Crystalline Solids, 352, pp. 1695-1699 (Mar. 2006).
Nucifora, Jr., F. et al., "Interference by Huntingtin and Atrophin-1 with CBP-Mediated Transcription Leading to Cellular Toxicity," Science, 291, pp. 2423-2428 (Mar. 2001).
O'Brien, J. "A Promising New Treatment for Alzheimer's Disease?" The Lancet, 7, pp. 768-769 (Sep. 2008).
Okumura, H. et al., "Phenothiazine and Carbazole-Related Compounds Inhibit Mitotic Kinesin Eg5 and Trigger Apoptosis in Transformed Culture Cells," Toxicology Letters, 166(1), pp. 44-52 (Sep. 2006).
Olla, S. et al., "Indolyl-Pyrrolone as a New Scaffold for Pim1 Inhibitors," Bioorganic & Medical Chemistry Letters, 19(5), pp. 1512-1516 (Mar. 2009).

Pan, J. et al., "Synthesis of Carrier-Transporting Dendrimers with Perylenebis(dicarboximide)s as a Luminescent Core," Eur. J. Org. Chem., 2006(4) pp. 986-1001 (Feb. 2006).
Panov, A. et al., "Early Mitochondrial Calcium Defects in Huntington's Disease are a Direct Effect of Polyglutamines," Nature Neuroscience, 5(8), pp. 731-736 (Aug. 2002).
Park, K. et al., "Promoting Axon Regeneration in the Adult CNS by Modulation of the PTEN/mTOR Pathway," Science, 322, pp. 963-966 (Nov. 2008).
Paton, J. et al., "Neurons Generated in the Adult Brain Are Recruited into Functional Circuits," Science, 225(4666), pp. 1046-1048 (Sep. 1984).
Pattison, L. et al., "Apoptotic Cascades as Possible Targets for Inhibiting Cell Death in Huntington's Disease," J Neurol, 253(9), pp. 1137-1142 (Sep. 2006).
Perutz, M., "Glutamine Repeats and Neurodegenerative Diseases: Molecular Aspects," TIBS, 24, pp. 58-63 (Feb. 1999).
Petit, S. et al., "Structure-Activity Relationship Analysis of the Peptide Deformylase Inhibitor 5-Bromo-1H-indole-3-acetohydroxamic Acid," ChemMedChem, 4(2), pp. 261-275 (Feb. 2009).
Petruska, J. et al., "Analysis of Strand Slippage in DNA Polymerase Expansions of CAG/CTG Triplet Repeats Associated with Neurodegenerative Disease," The Journal of Biological Chemistry, 273(9), pp. 5204-5210 (Feb. 1998).
Phillips, W. et al., "Abnormalities of Neurogenesis in the R6/2 Mouse Model of Huntington's Disease are Attributable to the In Vivo Microenvironment," The Journal of Neuroscience, 25(50), pp. 11564-11576 (Dec. 2005).
Pickard, B. et al., "Disruption of a Brain Transcription Factor, NPAS3, is Associated with Schizophrenia and Learning Disability," American Journal of Medical Genetics Part B, 136B(1), pp. 26-32 (Jul. 2005).
Pickard, B. et al., "The NPAS3 Gene—Emerging Evidence for a Role in Psychiatric Illness," Annals of Medicine, 38(6), pp. 439-448 (2006).
Pickard, B. et al., "Interacting Haplotypes at the NPAS3 Locus Alter Risk of Schizophrenia and Bipolar Disorder," Molecular Psychiatry, 14(9), pp. 874-884 (Sep. 2009).
Pieper, A. et al., "The Neuronal PAS Domain Protein 3 Transcription Factor Controls FGF-Mediated Adult Hippocampal Neurogenesis in Mice," PNAS, 102(39), pp. 14052-14057 (Sep. 2005).
Pieper, A. et al., "Discovery of a Proneurogenic, Neuroprotective Chemical," Cell, 142, pp. 39-51 (Jul. 2010).
Poesen, K. et al., "Novel Role for Vascular Endothelial Growth Factor (VEGF) Receptor-1 and its Ligand VEGF-B in Motor Neuron Degeneration," The Journal of Neuroscience, 28(42), pp. 10451-10459 (Oct. 2008).
Ponce, M. et al., "Synthesis and Isolation of Bromo-β-Carbolines Obtained by Bromination of β-Carboline Alkaloids," J. Heterocyclic Chem., 38, pp. 1087-1095 (Sep.-Oct. 2001).
Racke et al., PPARs in Neuroinflammation, Hindawi Publishing (Special Issue), 107 pgs., 2008.
Ramamoorthy, "Synthesis of small molecular inhibitors targeting signal transduction pathways," University of South Florida Thesis, pp. 1-70 (Jun. 10, 2009).
Raoul, C et al., "Motoneuron Death Triggered by a Specific Pathway Downstream of Fas: Potentiation by ALS-Linked SOD1 Mutations" Neuron, vol. 35, pp. 1067-1083 (Sep. 12, 2002).
Rische, T. et al., "One-Pot Synthesis of Pharmacologically Active Diamines via Rhodium-Catalysed Carbonylative Hydroaminomethylation of Heterocyclic Allylic Amines," Tetrahedron, 55(32), pp. 9801-9816 (Aug. 1999).
Rubinsztein, D., "Lessons from Animal Models of Huntington's Disease," TRENDS in Genetics, 18(4), pp. 202-209 (Apr. 2002).
Rubinsztein, D. et al., "Huntington's Disease: Molecular Basis of Neurodegeneration," Expert Reviews in Molecular Medicine, 5(22), pp. 1-21 (Aug. 2003).
Sadri-Vakili, G. et al., "Mechanisms of Disease: Histone Modifications in Huntington's Disease," Nature Clinical Practice: Neurology, 2(6), pp. 330-338 (Jun. 2006).

(56) References Cited

OTHER PUBLICATIONS

Schmidt, H. et al., "The Role of Neurotrophic Factors in Adult Hippocampal Neurogenesis, Antidepressant Treatments and Animal Models of Depressive-Like Behavior," *Behavioural Pharmacology*, 18(5-6), pp. 391-418 (Sep. 2007).
Stanfield, B. et al., "The Development of the Hippocampal Region," *Cerebral Cortex* (ed. Alan Peters and Edward G. Gones), vol. 7, pp. 91-131 (1988).
Sun, W. et al., "Programmed Cell Death of Adult-Generated Hippocampal Neurons is Mediated by the Proapoptotic Gene Bax," *The Journal of Neuroscience*, 24(49), pp. 11205-11213 (Dec. 2004).
Sundararajan, C. et al., "Photolytic Release of Carboxylic Acids Using Linked Donor-Acceptor Molecules: Direct versus Mediated Photoinduced Electron Transfer to N-Alkyl-4-picolinium Esters," *Organic Letters*, 7(13), pp. 2631-2634 (Jun. 2005).
Suzdalev, K.F. et al., "Synthesis of Indole 2,3-Epoxypropyl Derivatives and their Reactions with Amines," *Russian Journal of Organic Chemistry*, 41(2), pp. 233-237 (Feb. 2005).
Tang, T-S et al., "Disturbed $Ca^{2+}$ Signaling and Apoptosis of Medium Spiny Neurons in Huntington's Disease," *PNAS*, 102(7), pp. 2602-2607 (Feb. 2005).
Tatton, N.A. et al., "In Situ Detection of Apoptotic Nuclei in the Substantia Nigra Compacta of 1-methyl-4-phenyl-1,2,3,6-tetrahydropyridine-treated Mice Using Terminal Deoxynucleotidyl Transferase Labelling and Acridine Orange Staining," *Neuroscience*, 77(4), pp. 1037-1048 (Apr. 1997).
Teles, A.V.F.F. et al., "Increase in Bax Expression and Apoptosis are Associated in Huntington's Disease Progression," *Neuroscience Letters*, 438(1), pp. 59-63 (Jun. 2008).
Terfloth et al., "Electronic Screening: Lead Finding from Database Mining," in *The Practice of Medicinal Chemistry*, ed. C. Wermuth, Academic Press, pp. 131-157 (Mar. 7, 1996).
Tesla, R. et al., "Neuroprotective Efficacy of Aminopropyl Carbazoles in a Mouse Model of Amyotrophic Lateral Sclerosis" *PNAS*, vol. 109, No. 42, pp. 17016-17021 (Oct. 16, 2012).
Thiel, M. et al., "Contributions to the Development of Psychotropic Substances, 3 Mitt: Diphenylamine Derivatives with Pyridyl-substituted Side Chains and Guanidyl," *Chemical Monthly*, 93(5), pp. 1080-1089 (1962).
Van Praag, H. et al., "Running Increases Cell Proliferation and Neurogenesis in the Adult Mouse Dentate Gyrus," *Nature Neuroscience*, 2(3), pp. 266-270 (Mar. 1999).
Wanker, E. et al., "HIP-I: A Huntingtin Interacting Protein Isolated by the Yeast Two-Hybrid System," *Human Molecular Genetics*, 6(3), pp. 487-495 (Mar. 1997).
Watanabe, T. et al., "Palladium-Catalyzed Direct Synthesis of Carbazoles via One-Pot N-Arylation and Oxidative Biaryl Coupling: Synthesis and Mechanistic Study," *J. Org. Chem.*, 74, pp. 4720-4726 (Jul. 2009).
Weissman, S. et al., "Ligand-Free Palladium-Catalyzed Cyanation of Aryl Halids," *J. Org. Chem.*, 70(4), pp. 1508-1510 (Jan. 2005).
Wermuth, C., "Molecular Variations Based on Isosteric Replacements," *The Practice of Medicinal Chemistry* (ed. Camille G. Wermuth), pp. 203-237 (1996).
Wilde, R. et al., "Acyl CoA:Cholesterol Acyltransferase (ACAT) Inhibitors: Heterocyclic Bioisosteres for the Urea Group in DuP 128," *Bioorganic & Medicinal Chemistry Letters*, 5(2), pp. 177-180 (Jan. 1995).
Wilen, S., *Tables of Resolving Agents and Optical Resolutions* (Ed. Ernest L. Eliel) pp. 268-298 (1972).
Wilen, S. et al, "Strategies in Optical Resolutions," *Tetrahedron*, 33, pp. 2725-2736 (1977).
Xuan, A.G. et al., "BDNF Improves the Effects of Neural Stem Cells on the Rat Model of Alzheimer's Disease with Unilateral Lesion of Fimbria-Fornix," *Neuroscience Letters*, 400(3), pp. 331-335 (Aug. 2008).
Xue, Y. et al., "Novel Hypoglycemic Compounds-synthesis of Glycine Derivatives and Research on the Role of PPARS," *Jiefangjun Yaoxue Xueao*, 25(1), pp. 5-10 (2009).
Yang, J. et al., "Prevention of Apoptosis by Bcl-2: Release of Cytochrome c from Mitochondria Blocked," *Science*, 275, pp. 1129-1132 (Feb. 1997).
Yonemura, H. et al., "Spectroscopic Studies on Exchange Properties in Through-Ring Cyclodextrin Complexes of Carbazole-Viologen Linked Compounds: Effects of Spacer Chain Length," *J. Phys. Chem.*, 96, pp. 5765-5770 (Jul. 1992).
Yonemura, H. et al., "Effect of π-System on Long-Rang Photoinduced Electron Transfer in Through-Ring α-Cyclodextrin Complexes of Carbazole-Viologen Linked Compounds," *Tetrahedron Letters*, 39(38), pp. 6915-6918 (Sep. 1998).
Zeron, M. et al., "Mutant Huntingtin Enhances Excitotoxic Cell Death," *Molecular and Cellular Neuroscience*, 17(1), pp. 41-53 (Jan. 2001).
Zhang, H. et al., "Implantation of Neural Stem Cells Embedded in Hyaluronic Acid and Collagen Composite Conduit Promotes Regeneration in a Rabbit Facial Nerve Injury Model," *Journal of Translational Medicine*, 6(67), pp. 41-53 (Nov. 2008).
Zoidis, G. et al., "Design and Synthesis of 1,2-annulated Adamantane Piperidines with Anti-Influenza Virus Activity," *Bioorganic & Medicinal Chemistry*, 17(4), pp. 1534-1541 (Feb. 2009).
Zuccato, C. et al., "Huntingtin Interacts with REST/NRSF to Modulate the Transcription of NRSE-controlled Neuronal Genes," *Nature Genetics*, 35(1), pp. 76-83 (Sep. 2003).
PCT International Search Report based on PCT/US2010/020681 dated Jun. 17, 2010.
USPTO Office Action in U.S. Appl. No. 12/832,056 mailed Feb. 9, 2012.
PCT International Search Report based on PCT/2011/043185 dated Apr. 10, 2012.
USPTO Office Action in U.S. Appl. No. 12/832,056 mailed Jul. 11, 2012.
USPTO Office Action in U.S. Appl. No. 12/685,652 mailed Jul. 19, 2012.
PCT International Search Report based on PCT/2012/052283 dated Oct. 24, 2012.
USPTO Notice of Allowance in U.S. Appl. No. 12/832,056 mailed Nov. 20, 2012.
USPTO Office Action in U.S. Appl. No. 12/685,652 mailed Mar. 20, 2013.
USPTO Office Action in U.S. Appl. No. 13/177,981 mailed Apr. 16, 2013.
USPTO Office Action in U.S. Appl. No. 12/685,652 mailed Apr. 26, 2013.
PCT International Preliminary Report on Patentability based on PCT/2011/043185 dated Jun. 25, 2013.
USPTO Office Action in U.S. Appl. No. 13/740,876 mailed Jul. 12, 2013.
USPTO Office Action in U.S. Appl. No. 13/709,531 mailed Jul. 17, 2013.
USPTO Office Action in U.S. Appl. No. 13/770,676 mailed Sep. 6, 2013.
USPTO Office Action in U.S. Appl. No. 13/177,981 mailed Nov. 18, 2013.
USPTO Office Action in U.S. Appl. No. 13/740,807 mailed Dec. 5, 2013.
USPTO Office Action in U.S. Appl. No. 13/594,223 mailed Jan. 13, 2014.
PCT International Search Report based on PCT/US13/56440 dated Jan. 22, 2014.
USPTO Office Action in U.S. Appl. No. 13/770,706 mailed Jan. 27, 2014.
Awasthi et al., "Modulation of Doxorubicin Cytotoxicity by Ethacrynic Acid", Int. J. Cancer, vol. 69, pp. 333-339 (1996).
Jantas et al., "Protective Effect of Memantine Against Doxorubicin Toxicity in Primary Neuronal Cell Cultures: Influence a Development Stage", Neurotox Res., vol. 15, pp. 24-37 (2009).
Newman et al., "Amelioration of Adriamycin and Daunorubicin Myocardial Toxicity by Adenosine", Cancer Research, vol. 41, pp. 3483-3488, Sep. 1981.

(56) References Cited

OTHER PUBLICATIONS

Pereira et al., "Photosensitization of Human Diploid Cell, Cultures by Intracellular Flavins and Protection by Antioxidants", Photochemistry and Photobiology, vol. 24, Issue 3, pp. 237-242 (Sep. 1976).
STN Registry Entry 448231-97-8 entered Sep. 9, 2002.
USPTO Office Action in U.S. Appl. No. 13/594,223 mailed Apr. 19, 2016.
Supplementary European Search Report issued in European Application No. EP 12883358 mailed on May 6, 2016.
Supplementary European Search Report issued in European Application No. EP 13830535 mailed Jul. 1, 2016.
Van Waarde et al., "The Cholinergic System, Sigma-1 receptors and cognition", Behavioural Brain Research, vol. 221, No. 2, pp. 543-554, Dec. 26, 2009.
Schwarcz et al., "Open label evaluation of the novel antipsychotic compound BW234U in chronic schizophrenics". Drug Development Research, vol. 5, No. 4, pp. 387-393, Jan. 1, 1985.

PRO-NEUROGENIC COMPOUNDS

CROSS REFERENCE TO RELATED APPLICATIONS

This application claims priority to and the benefit of U.S. Provisional Application No. 61/693,108 filed Aug. 24, 2012, the entire content of which application is hereby incorporated herein by reference.

STATEMENT REGARDING FEDERALLY SPONSORED RESEARCH

This invention was made with government support under Grant Numbers 5DP1OD00027605, 5R37MH05938809, and 1RO1MH087986, which were awarded by the National Institute of Health; the Government has certain rights in the invention.

TECHNICAL FIELD

This presently disclosed embodiments relate generally to the discovery of pro-neurogenic compounds capable of promoting neurogenesis and/or reducing neuronal cell death.

BACKGROUND

It is now accepted that the adult vertebrate brain fosters the birth and functional incorporation of newly formed neurons (Goldman and Nottebohm, Proc Natl Acad Sci USA 1983, 80: 2390-2394; Paton and Nottebohm, Science 1984, 225, 1046-1048; Burd and Nottebohm, J Comp Neurol 1985, 240:143-152). However, it was long thought that no new neurons could be added to the adult mammalian brain. This dogma was challenged in the 1960's when autoradiographic evidence of new neuron formation in the hippocampal dentate gyms, olfactory bulb, and cerebral cortex of the adult rat was presented (Altman, J. Science 1962, 135, 1127-1128; Altman, J. J Comp Neurol 1966, 128:431-474; Altman, Anat Rec 1963, 145:573-591; Altman and Das, J. Comp. Neurol. 1965, 124, 319-335; Altman and Das, J Comp Neurol 1966, 126:337-390). It is now accepted that within all mammalian species, including humans (Eriksson et al., Nat. Med. 1998, 4(11), 1313-1317), there are two major reservoirs of neuronal stem cells, one located in the subgranular zone (SGZ) of the hippocampal dentate gyms and another in the subventricular zone (SVZ) (Gross, Natl. Rev. 2000, 1, 67-72). Neural stem cells in the SVZ facilitate formation of new neurons that migrate rostrally to populate the olfactory bulb, while neural stem cells in the SGZ produce neurons that integrate locally in the granular layer of the dentate gyrus, a region of the hippocampus that exhibits lifelong structural and functional plasticity.

The process of new neuron formation in the adult mouse brain can be influenced by environmental, chemical and genetic variables. As demonstrated by Gage and colleagues, neurogenesis in the adult mouse brain is enhanced when animals are exposed to an enriched environment (Kempermann et al., Nature 1997, 386, 493-495) or able to exercise voluntarily (van Praag et al., Nat. Neuro-sci. 1999, 2, 266-270). More recently, anti-depressant drugs have been shown to enhance levels of adult neurogenesis in animals, including humans (Schmidt et al., Behav Pharmacol. 2007 September; 18(5-6):391-418; Boldrini et al., Neuropsychopharmacology 2009, 34, 2376-2389). Among many genes reported to impact adult neurogenesis is the gene encoding neuronal PAS domain protein 3 (NPAS3), a central nervous system (CNS)-specific transcription factor that has been associated with schizophrenia and bipolar disorder (Kamnasaran et al., J. Med. Genet. 2003, 40, 325-332; Pickard et al., Am. J. Med. Genet. B. Neuropsychiatr. Genet. 2005, 136B, 26-32; Pickard et al., Ann Med. 2006, 38, 439-448; Pickard et al., Mol. Psychiatry. 2009, 14, 874-884; Lavedan et al., Pharmacogenomics 2008, 9: 289-301) Animals missing both copies of the NPAS3 gene suffer a profound loss of adult hippocampal neurogenesis coupled with significant behavioral deficits (Pieper et al., Proc. Natl. Acad. Sci. USA 2005, 102, 14052-14057). Knowing that impaired post-natal neurogenesis elicits unfavorable phenotypic deficits, it is predicted that pro-neurogenic chemical compounds should exhibit favorable therapeutic benefits.

SUMMARY

The presently disclosed embodiments relate generally to compounds that promote the generation or the survival of existing neurons in the mammalian brain. For the purpose of simplicity these compounds are referred to as being pro-neurogenic. In certain embodiments, the compounds promote the generation or survival of neurons in the post-natal mammalian brain. In certain embodiments, the compounds promote the survival, growth, development and/or function of neurons, particularly CNS, brain, cerebral, and hippocampal neurons. In certain embodiments, the compounds stimulate post-natal hippocampal neurogenesis, which while not wishing to be bound by theory, is believed to represent a therapeutic target for a variety of neuropsychiatric and neurodegenerative diseases, including (but not limited to) schizophrenia, major depression, bipolar disorder, normal aging, epilepsy, traumatic brain injury, post-traumatic stress disorder, Parkinson's disease, Alzheimer's disease, Down syndrome, spinocerebellar ataxia, amyotrophic lateral sclerosis, Huntington's disease, stroke, radiation therapy, chronic stress, abuse of neuro-active drugs (such as alcohol, opiates, methamphetamine, phencyclidine, and cocaine), retinal degeneration, spinal cord injury, and peripheral nerve injury. In certain embodiments, the compounds stimulate post-natal hypothalamic neurogenesis, which can provide therapeutic benefits in weight management, such as physiological weight loss associated with various conditions, including but not limited to, normal aging, chemotherapy, radiation therapy, stress, drug abuse, anorexia, as well as other diseases discussed herein.

In an aspect, compounds of the presently disclosed embodiments may include those represented by formula (I):

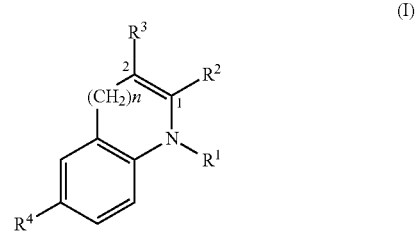

wherein:
R² and R³, together with C1 and C2, form the optionally substituted phenyl, pyridine or pyrimidine ring of formulas (II)-(IV) described below, or are defined as $R^{2d}$ and $R^{3d}$ of formula (V), respectively;

$R^4$ is defined as any one of $R^{4a}$-$R^{4d}$ in formulas (II)-(IV); and n is 0 or 2.

For example, a compound or pharmaceutically acceptable salt thereof, for promoting neurogenesis and/or reducing neuronal cell death, can be represented by formula (II):

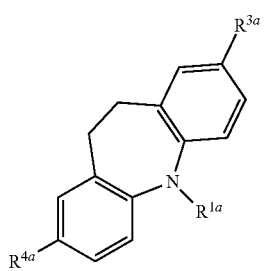

(II)

wherein $R^{1a}$ is selected from the group consisting of: —$CH_2$—C(O)—$Z^{1a}$ and —$CH_2$—C($R^{A1}$)($R^{A2}$)—$CH_2$—$Z^{2a}$; and $R^{3a}$ and $R^{4a}$ are each independently selected from the group consisting of: hydrogen, halo, hydroxyl, $C_{1-3}$ alkoxyl, cyano, carboxyl, and formamide;

wherein $Z^{1a}$ is selected from the group consisting of: hydroxyl; $C_{1-6}$ alkoxyl; amine optionally substituted with 1 or more $C_{1-12}$ alkyl, $C_{2-12}$ alkenyl, $C_{3-12}$ cycloalkyl, $C_{1-12}$ alkyl sulfonyl optionally substituted with 1-6 halo, $C_{6-12}$ aryl sulfonyl optionally substituted with 1-6 halo, $C_{4-12}$ heteroaryl sulfonyl optionally substituted with 1-6 halo, $C_{2-12}$ alkyl carbonyl optionally substituted with 1-6 halo, and/or $C_{2-12}$ carboxyalkyl optionally substituted with 1-6 halo; $C_{2-12}$ heterocyclyl; $C_{6-12}$ aryl optionally substituted with 1 or more halo, hydroxyl, $C_{1-6}$ alkyl and/or $C_{1-6}$ alkoxyl; and $C_{4-12}$ heteroaryl optionally substituted with 1 or more halo, hydroxyl, $C_{1-6}$ alkyl and/or $C_{1-6}$ alkoxyl;

wherein one of $R^{A1}$ and $R^{A2}$ is hydroxyl, halo, or amine optionally substituted with 1 or more $C_{1-6}$ alkyl, $C_{2-6}$ alkenyl, $C_{3-6}$ cycloalkyl, $C_{2-6}$ heterocyclyl, $C_{6-12}$ aryl, and/or $C_{4-12}$ heteroaryl; and the other of $R^{A1}$ and $R^{A2}$ is hydrogen;

wherein $Z^{2a}$ is selected from the group consisting of: halo, O($R^a$), S($R^b$) and N($R^c$)($R^d$);

wherein $R^a$ and $R^b$ are each independently selected from the group consisting of: $C_{1-12}$ alkyl; $C_{2-12}$ alkenyl; $C_{3-12}$ cycloalkyl; $C_{2-6}$ heterocyclyl; $C_{6-12}$ aryl optionally substituted with 1 or more halo, hydroxyl, $C_{1-6}$ alkyl and/or $C_{1-6}$ alkoxyl; and $C_{4-12}$ heteroaryl optionally substituted with 1 or more halo, hydroxyl, $C_{1-6}$ alkyl and/or $C_{1-6}$ alkoxyl;

wherein $R^c$ and $R^d$ are each independently selected from the group consisting of: hydrogen; $C_{1-12}$ alkyl; $C_{2-12}$ alkenyl; $C_{3-12}$ cycloalkyl; $C_{2-6}$ heterocyclyl; $C_{6-12}$ aryl optionally substituted with 1 or more halo, hydroxyl, $C_{1-6}$ alkyl and/or $C_{1-6}$ alkoxyl; and $C_{4-12}$ heteroaryl optionally substituted with 1 or more halo, hydroxyl, $C_{1-6}$ alkyl and/or $C_{1-6}$ alkoxyl; or wherein $R^c$ and $R^d$ together with the nitrogen they are attached to form a $C_{4-14}$ heteroaryl optionally substituted with 1 or more halo, hydroxyl, $C_{1-6}$ alkyl and/or $C_{1-6}$ alkoxyl.

In some embodiments, one or more of the following definitions apply:

(1) $R^{3a}$ and $R^{4a}$ are both hydrogen or both bromo;

(2) $Z^{1a}$ is hydroxyl or amine optionally substituted with 1 or more $C_{1-12}$ alkyl, $C_{2-12}$ alkenyl, and/or $C_{3-12}$ cycloalkyl;

(3) one of $R^{A1}$ and $R^{A2}$ is hydroxyl or halo; and the other of $R^{A1}$ and $R^{A2}$ is hydrogen;

(4) $Z^{2a}$ is O($R^a$) or S($R^b$); and/or (5) $Z^{2a}$ is N($R^c$)($R^d$).

For example, $R^{1a}$ may be —$CH_2$—C(O)—$Z^{1a}$ or —$CH_2$—C($R^{A1}$)($R^{A2}$)—$CH_2$—$Z^{2a}$.

When $R^{1a}$ is —$CH_2$—C(O)—$Z^{1a}$, $Z^{1a}$ may be hydroxyl or $C_{1-6}$ alkoxyl. $Z^{1a}$ may also be amine optionally substituted with 1 or more $C_{1-12}$ alkyl, $C_{2-12}$ alkenyl, $C_{3-12}$ cycloalkyl, $C_{1-12}$ alkyl sulfonyl optionally substituted with 1-6 halo, $C_{6-12}$ aryl sulfonyl optionally substituted with 1-6 halo, $C_{4-12}$ heteroaryl sulfonyl optionally substituted with 1-6 halo, $C_{2-12}$ alkyl carbonyl optionally substituted with 1-6 halo, and/or $C_{2-12}$ carboxyalkyl optionally substituted with 1-6 halo. For example, $Z^{1a}$ can be amine optionally substituted with 1 or more $C_{1-12}$ alkyl, $C_{2-12}$ alkenyl, and/or $C_{3-12}$ cycloalkyl. $Z^{1a}$ may also be $C_{2-12}$ heterocyclyl; $C_{6-12}$ aryl optionally substituted with 1 or more halo, hydroxyl, $C_{1-6}$ alkyl and/or $C_{1-6}$ alkoxyl; or $C_{4-12}$ heteroaryl optionally substituted with 1 or more halo, hydroxyl, $C_{1-6}$ alkyl and/or $C_{1-6}$ alkoxyl.

When $R^{1a}$ is —$CH_2$—C($R^{A1}$)($R^{A2}$)—$CH_2$—$Z^{2a}$, both of $R^{A1}$ and $R^{A2}$ can be hydrogen. Alternatively, one of $R^{A1}$ and $R^{A2}$ is hydroxyl, halo (e.g., fluoro), or amine optionally substituted with 1 or more $C_{1-6}$ alkyl (e.g., methyl), $C_{2-6}$ alkenyl, $C_{3-6}$ cycloalkyl, $C_{2-6}$ heterocyclyl, $C_{6-12}$ aryl, and/or $C_{4-12}$ heteroaryl; and the other of $R^{A1}$ and $R^{A2}$ is hydrogen. $Z^{2a}$ can be halo, O($R^a$), S($R^b$) or N($R^c$)($R^d$). $R^a$ and $R^b$ are each common substitutients such as: $C_{1-12}$ alkyl; $C_{2-12}$ alkenyl; $C_{3-12}$ cycloalkyl; $C_{2-6}$ heterocyclyl; $C_{6-12}$ aryl optionally substituted with 1 or more halo, hydroxyl, $C_{1-6}$ alkyl and/or $C_{1-6}$ alkoxyl; and $C_{4-12}$ heteroaryl optionally substituted with 1 or more halo, hydroxyl, $C_{1-6}$ alkyl and/or $C_{1-6}$ alkoxyl. $R^c$ and $R^d$ can both be hydrogen or each common substitutients such as: $C_{1-12}$ alkyl; $C_{2-12}$ alkenyl; $C_{3-12}$ cycloalkyl; $C_{2-6}$ heterocyclyl; $C_{6-12}$ aryl optionally substituted with 1 or more halo, hydroxyl, $C_{1-6}$ alkyl and/or $C_{1-6}$ alkoxyl; and $C_{4-12}$ heteroaryl optionally substituted with 1 or more halo, hydroxyl, $C_{1-6}$ alkyl and/or $C_{1-6}$ alkoxyl. Alternatively, $R^c$ and $R^d$ together with the nitrogen they are attached to can form a ring structure, such as a $C_{4-14}$ heteroaryl optionally substituted with 1 or more halo, hydroxyl, $C_{1-6}$ alkyl and/or $C_{1-6}$ alkoxyl.

$R^{3a}$ may be hydrogen, halo (e.g., bromo), hydroxyl, $C_{1-3}$ alkoxyl (e.g., methoxyl), cyano, carboxyl, or formamide. In certain embodiments, $R^{3a}$ is hydrogen. In some embodiments, $R^{3a}$ is bromo.

$R^{4a}$ may be hydrogen, halo (e.g., bromo), hydroxyl, $C_{1-3}$ alkoxyl (e.g., methoxyl), cyano, carboxyl, or formamide. In certain embodiments, $R^{4a}$ is hydrogen. In some embodiments, $R^{4a}$ is bromo.

In certain embodiments, the presently disclosed embodiments include a compound or pharmaceutically acceptable salt thereof, for promoting neurogenesis and/or reducing neuronal cell death, the compound having formula (III):

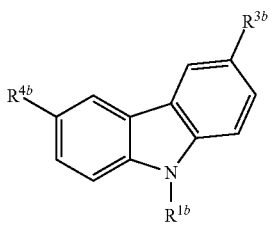

(III)

wherein $R^{1b}$ is selected from the group consisting of: hydrogen; $C_{1-6}$ alkyl optionally substituted with 1 or more halo, hydroxyl, cyano and/or azide; —CH($R^5$)—C(O)—$Z^{1b}$; and —CH$_2$—C($R^{41}$)($R^{42}$)—CH$_2$—$Z^{2b}$;

wherein $R^5$ is hydrogen or $C_{1-3}$ alkyl;

wherein one of $R^{41}$ and $R^{42}$ is hydroxyl or halo and the other is hydrogen;

wherein $Z^{1b}$ is selected from the group consisting of: hydroxyl; $C_{1-6}$ alkoxyl; and amine optionally substituted with a hydroxyl, $C_{1-12}$ alkyl sulfonyl optionally substituted with 1-6 halo, $C_{6-12}$ aryl sulfonyl optionally substituted with 1-6 halo, $C_{4-12}$ heteroaryl sulfonyl optionally substituted with 1-6 halo, $C_{2-12}$ alkyl carbonyl optionally substituted with 1-6 halo, and/or $C_{2-12}$ carboxyalkyl optionally substituted with 1-6 halo;

wherein $Z^{2b}$ is selected from the group consisting of: $C_{1-3}$ alkyl, azide, and N($R^6$)($R^7$);

wherein $R^6$ and $R^7$ are each independently selected from the group consisting of: hydrogen; carboxamide optionally substituted with 1 or more $C_{1-6}$ alkyl, $C_{6-12}$ aryl and/or $C_{4-12}$ heteroaryl; $C_{6-12}$ aryl optionally substituted with 1 or more halo, hydroxyl, $C_{1-6}$ alkyl and/or $C_{1-6}$ alkoxyl; $C_{1-12}$ alkyl sulfonyl optionally substituted with 1-6 halo; $C_{6-12}$ aryl sulfonyl optionally substituted with 1-6 halo; and $C_{4-12}$ heteroaryl sulfonyl optionally substituted with 1-6 halo; wherein no more than one of $R^6$ and $R^7$ is hydrogen; and wherein $R^{3b}$ and $R^{4b}$ are each independently selected from the group consisting of: hydrogen, halo, hydroxyl, $C_{1-3}$ alkoxyl, cyano, carboxyl, and formamide.

In some embodiments, one or more of the following definitions apply:

(1) when $R^{1b}$ is optionally substituted $C_{1-6}$ alkyl, Rib selected from unsubstituted $C_{1-6}$ alkyl or $C_{3-6}$ alkyl substituted with 1 hydroxyl or $C_{1-6}$ alkyl substituted with 1 cyano;

(2) when Rib unsubstituted $C_{1-6}$ alkyl, $R^{1b}$ is unsubstituted $C_{2-6}$ alkyl;

(3) when $R^5$ is hydrogen, $Z^{1b}$ is amine optionally substituted with a hydroxyl, $C_{1-12}$ alkyl sulfonyl optionally substituted with 1-6 halo, $C_{6-12}$ aryl sulfonyl optionally substituted with 1-6 halo, $C_{4-12}$ heteroaryl sulfonyl optionally substituted with 1-6 halo, $C_{2-12}$ alkyl carbonyl optionally substituted with 1-6 halo, and/or $C_{2-12}$ carboxyalkyl optionally substituted with 1-6 halo; and/or (4) $Z^{2b}$ is azide or N(R6)(R7).

For example, $R^{1b}$ may be hydrogen. $R^{1b}$ may also be $C_{1-6}$ alkyl optionally substituted with 1 or more halo, hydroxyl, cyano and/or azide, such as unsubstituted $C_{1-6}$ alkyl (e.g., methyl, ethyl, n-propyl, isopropyl, or tert-butyl) or $C_{3-6}$ alkyl substituted with 1 hydroxyl (e.g., at the beta-carbon) or $C_{1-6}$ alkyl substituted with 1 cyano. $R^{1b}$ may also be —CH($R^5$)—C(O)—$Z^{1b}$ or —CH$_2$—C($R^{41}$)($R^{42}$)—CH$_2$—$Z^{2b}$.

$R^5$ can be hydrogen or $C_{1-3}$ alkyl (e.g., methyl). $Z^{1b}$ can be hydroxyl or $C_{1-6}$ alkoxyl. $Z^{1b}$ can also be amine optionally substituted with 1 hydroxyl, or amine optionally substituted with $C_{1-12}$ alkyl sulfonyl, $C_{6-12}$ aryl sulfonyl, $C_{4-12}$ heteroaryl sulfonyl, $C_{2-12}$ alkyl carbonyl, or $C_{2-12}$ carboxyalkyl (e.g., —CH$_2$C(O)OH). The $C_{1-12}$ alkyl sulfonyl, $C_{6-12}$ aryl sulfonyl, $C_{4-12}$ heteroaryl sulfonyl, $C_{2-12}$ alkyl carbonyl, and $C_{2-12}$ carboxyalkyl groups can contain one or more common substitutients such as alkyl, halo, hydroxyl, alkoxyl, aryl and/or heteroaryl.

One of $R^{41}$ and $R^{42}$ can be hydroxyl or halo (e.g., fluoro) and the other of $R^{41}$ and $R^{42}$ can be hydrogen. Alternatively, both $R^{41}$ and $R^{42}$ can be hydrogen. $Z^{2b}$ can be $C_{1-3}$ alkyl. $Z^{2b}$ can also be azide or N($R^6$)($R^7$). $R^6$ and $R^7$ can both be hydrogen. Alternatively, only one of $R^6$ and $R^7$ is hydrogen, or none of $R^6$ and $R^7$ is hydrogen. $R^6$ and $R^7$ can also be carboxamide optionally substituted with 1 or more $C_{1-6}$ alkyl, $C_{6-12}$ aryl and/or $C_{4-12}$ heteroaryl; $C_{6-12}$ aryl optionally substituted with 1 or more halo, hydroxyl, $C_{1-6}$ alkyl and/or $C_{1-6}$ alkoxyl; $C_{1-12}$ alkyl sulfonyl optionally substituted with 1-6 halo; $C_{6-12}$ aryl sulfonyl optionally substituted with 1-6 halo; or $C_{4-12}$ heteroaryl sulfonyl optionally substituted with 1-6 halo.

$R^{3b}$ may be hydrogen, halo (e.g., bromo), hydroxyl, $C_{1-3}$ alkoxyl (e.g., methoxyl), cyano, carboxyl, or formamide. In certain embodiments, $R^{3b}$ is hydrogen. In some embodiments, $R^{3b}$ is bromo.

$R^{4b}$ may be hydrogen, halo (e.g., bromo), hydroxyl, $C_{1-3}$ alkoxyl (e.g., methoxyl), cyano, carboxyl, or formamide. In certain embodiments, $R^{4b}$ is hydrogen. In some embodiments, $R^{4b}$ is bromo.

For example, both $R^{3b}$ and $R^{4b}$ are hydrogen. Both $R^{3b}$ and $R^{4b}$ can be bromo.

In certain embodiments, the presently disclosed embodiments include a compound or pharmaceutically acceptable salt thereof, for promoting neurogenesis and/or reducing neuronal cell death, the compound having formula (IV):

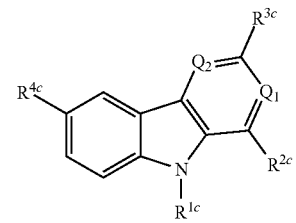

(IV)

wherein:

$R^{1c}$ is selected from the group consisting of: hydrogen, $C_{1-6}$ alkyl, $C_{1-6}$carboxyalkyl, $C_{1-12}$ alkyl sulfonyl optionally substituted with 1-6 halo, $C_{6-12}$ aryl sulfonyl optionally substituted with 1-6 halo and $C_{4-12}$ heteroaryl sulfonyl optionally substituted with 1-6 halo;

$R^{2c}$ is selected from the group consisting of: hydrogen; hydroxyl; cyano; halo; amine optionally substituted with 1 or more $C_{1-6}$ alkyl, $C_{2-6}$ alkenyl, $C_{3-6}$ cycloalkyl, aryl, and/or heteroaryl; and $C_{1-12}$ alkoxyl;

$R^{3c}$ is selected from the group consisting of: carboxyl; $C_{1-6}$ alkoxycarbonyl; hydroxyl; $C_{1-12}$ alkoxyl; cyano; halo; and amine optionally substituted with 1 or more $C_{1-6}$ alkyl, $C_{2-6}$ alkenyl, $C_{3-6}$ cycloalkyl, aryl, and/or heteroaryl;

$R^{4c}$ is selected from the group consisting of: hydrogen, halo, hydroxyl, and $C_{1-3}$ alkoxyl; and one or both of $Q_1$ and $Q_2$ are nitrogen.

In some embodiments, one or more of the following definitions apply:
(1) $R^{2c}$ is hydrogen; hydroxyl; or $C_{1-12}$ alkoxyl; and/or
(2) $R^{3c}$ is carboxyl; $C_{1-6}$ alkoxycarbonyl; hydroxyl; or amine substituted with 1-2 $C_{1-6}$ alkyl.

For example, $R^{1c}$ can be hydrogen. $R^{1c}$ can also be $C_{1-6}$ alkyl or $C_{2-6}$ carboxyalkyl (e.g., —CH$_2$C(O)OH). $R^{1c}$ can also be $C_{1-12}$ alkyl sulfonyl optionally substituted with 1-6 halo or $C_{6-12}$ aryl sulfonyl (e.g., —S(O)$_2$Ph) optionally substituted with 1-6 alkyl, substituted alkyl (e.g., CF$_3$) and/or halo. $R^{1c}$ can also be $C_{4-12}$ heteroaryl sulfonyl optionally substituted with 1-6 alkyl, substituted alkyl (e.g., CF$_3$) and/or halo.

$R^{2c}$ can be hydrogen or hydroxyl. $R^{2c}$ can also be cyano; halo; or amine optionally substituted with 1 or more $C_{1-6}$ alkyl, $C_{2-6}$ alkenyl, $C_{3-6}$ cycloalkyl, aryl, and/or heteroaryl. $R^{2c}$ can also be $C_{1-12}$ alkoxyl.

$R^{3c}$ can be carboxyl or $C_{1-6}$ alkoxycarbonyl (e.g., —C(O)OCH$_3$ or —C(O)OCH$_2$CH$_3$). $R^{3c}$ can also be hydroxyl. $R^{3c}$ can also be $C_{1-12}$ alkoxyl; cyano; or halo (e.g., bromo). $R^{3c}$ can also be amine optionally substituted with 1 or more $C_{1-6}$ alkyl, $C_{2-6}$ alkenyl, $C_{3-6}$ cycloalkyl, aryl, and/or heteroaryl, such as N(CH$_3$)$_2$.

$R^{4c}$ can be hydrogen or halo (e.g., bromo). $R^{4c}$ can also be hydroxyl or and $C_{1-3}$ alkoxyl.

$Q_1$ and $Q_2$ can both be nitrogen. Alternatively, one of $Q_1$ and $Q_2$ is nitrogen and the other of $Q_1$ and $Q_2$ is carbon. In some embodiments, when both $Q_1$ and $Q_2$ are be nitrogen and both $R^{2c}$ and $R^{3c}$ are hydroxyl, the corresponding ring structure is typically represented by:

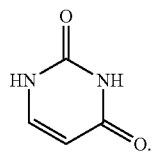

In certain embodiments, the presently disclosed embodiments include a compound or pharmaceutically acceptable salt thereof, for promoting neurogenesis and/or reducing neuronal cell death, the compound having formula (V):

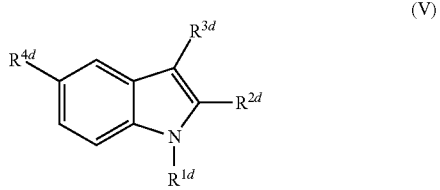

(V)

wherein $R^{1d}$ is selected from the group consisting of:
hydrogen and CH$_2$—C(R$^{41}$)(R$^{42}$)—CH$_2$—N(R$^6$)(R$^7$);
wherein one of $R^{41}$ and $R^{42}$ is hydroxyl or halo and the other is hydrogen; and
wherein $R^6$ and $R^7$ are each independently selected from the group consisting of:
hydrogen; $C_{6-12}$ aryl optionally substituted with 1 or more halo, hydroxyl, $C_{1-6}$ alkyl and/or $C_{1-6}$ alkoxyl; and $C_{4-12}$ heteroaryl optionally substituted with 1 or more halo, hydroxyl, $C_{1-6}$ alkyl and/or $C_{1-6}$ alkoxyl;
wherein $R^{2d}$ is selected from the group consisting of: halo, hydroxyl, $C_{1-12}$ alkoxyl, cyano, aryl, and heteroaryl;
wherein $R^{3d}$ is selected from the group consisting of:
hydrogen and amine optionally substituted with 1 or more $C_{1-6}$ alkyl, $C_{2-6}$ alkenyl, $C_{3-6}$ cycloalkyl, $C_{2-6}$ heterocyclyl, aryl, and/or heteroaryl; and
wherein $R^{4d}$ is selected from the group consisting of:
hydrogen, halo, hydroxyl, and $C_{1-3}$ alkoxyl.

In some embodiments, $R^{2d}$ is cyano, and/or $R^{4d}$ is hydrogen, bromo or methoxy.

For example, $R^{1d}$ can be hydrogen. $R^{1d}$ can also be CH$_2$—C(R$^{41}$)(R$^{42}$)—CH$_2$—N(R$^6$)(R$^7$). One of $R^{41}$ and $R^{42}$ can be hydroxyl and the other is hydrogen. One of $R^{41}$ and $R^{42}$ can be halo (e.g., fluoro) and the other is hydrogen. Alternatively, both $R^{41}$ and $R^{42}$ can be hydrogen. $R^6$ and $R^7$ can both be hydrogen. Alternatively, one or both of $R^6$ and $R^7$ can be $C_{6-12}$ aryl optionally substituted with 1 or more halo, hydroxyl, $C_{1-6}$ alkyl and/or $C_{1-6}$ alkoxyl; or $C_{4-12}$ heteroaryl optionally substituted with 1 or more halo, hydroxyl, $C_{1-6}$ alkyl and/or $C_{1-6}$ alkoxyl.

$R^{2d}$ can be halo, hydroxyl, or $C_{1-12}$ alkoxyl. $R^{2d}$ can also be cyano. $R^{2d}$ can also be aryl (e.g., $C_{6-12}$) or heteroaryl (e.g., $C_{4-12}$).

$R^{3d}$ can be hydrogen. $R^{3d}$ can also be amine optionally substituted with 1 or more $C_{1-6}$ alkyl, $C_{2-6}$ alkenyl, $C_{3-6}$ cycloalkyl, $C_{2-6}$ heterocyclyl, aryl (e.g., $C_{6-12}$), and/or heteroaryl (e.g., $C_{4-12}$).

$R^{4d}$ can be hydrogen, halo (e.g., bromo), hydroxyl, or $C_{1-3}$ alkoxyl (e.g., methoxyl).

Compounds or salts thereof having any combinations of the above definitions of the various groups are all included in the presently disclosed embodiments.

The presently disclosed embodiments also include compositions (e.g., pharmaceutical compositions) that include such compounds as well as methods of making, identifying, and using such compounds. Other features and advantages are described in, or will be apparent from, the present specification and accompanying drawings.

Any of the compounds disclosed herein can be used in any of the methods or compositions described anywhere herein. The presently disclosed embodiments relate generally to stimulating neurogenesis (e.g., post-natal neurogenesis, e.g., post-natal hippocampal and/or hypothalamic neurogenesis) and protecting neurons from death with a compound of any of the formulae described herein or a salt (e.g., a pharmaceutically acceptable salt) thereof as defined anywhere herein.

For example, methods of promoting the generation of neurons are featured. As another example, methods of promoting the survival, growth, development and/or function of neurons, particularly CNS, brain, cerebral, hippocampal and hypothalamic neurons are featured. As a further example, methods of stimulating post-natal hippocampal and/or hypothalamic neurogenesis are featured.

In some embodiments, such methods can include in vitro methods, e.g., contacting a sample (e.g., a cell or tissue) with a compound of any of the formulae described herein or a salt (e.g., a pharmaceutically acceptable salt) thereof as defined anywhere herein. In other embodiments, the methods can include administering a compound of any of the formulae described herein or a salt (e.g., a pharmaceutically acceptable salt) thereof as defined anywhere herein to a subject (e.g., a mammal, such as a human).

Accordingly, in an aspect, the presently disclosed embodiments include and feature methods of screening for (thereby identifying) compounds that stimulate neurogenesis (e.g., post-natal neurogenesis, e.g., post-natal hippocampal and/or hypothalamic neurogenesis) or protect newborn neurons from cell death.

In another aspect, methods for treating (e.g., controlling, relieving, ameliorating, alleviating, or slowing the progression of) or methods for preventing (e.g., delaying the onset of or reducing the risk of developing) one or more diseases, disorders, or conditions caused by, or associated with insufficient (e.g., aberrant) neurogenesis or unwanted neuronal cell death in a subject in need thereof are featured. The methods include administering to the subject an effective amount of a compound of any of the formulae described herein or a salt (e.g., a pharmaceutically acceptable salt) thereof as defined anywhere herein to the subject.

In another aspect, the use of a compound of any of the formulae described herein or a salt (e.g., a pharmaceutically acceptable salt) thereof as defined anywhere herein in the preparation of, or for use as, a medicament for the treatment (e.g., controlling, relieving, ameliorating, alleviating, or slowing the progression of) or prevention (e.g., delaying the onset of or reducing the risk of developing) of one or more diseases, disorders, or conditions caused by, or associated with, insufficient (e.g., aberrant) neurogenesis or unwanted neuronal cell death is featured.

In some embodiments, the one or more diseases, disorders, or conditions can include neuropathies, nerve trauma, and neurodegenerative diseases. In some embodiments, the one or more diseases, disorders, or conditions can be diseases, disorders, or conditions caused by, or associated with insufficient neurogenesis (e.g., aberrant hippocampal and/or hypothalamic neurogenesis) as is believed to occur in neuropsychiatric diseases, or aberrant neuronal cell death as is believed to occur in neurodegenerative diseases. Examples of the one or more diseases, disorders, or conditions include, but are not limited to, schizophrenia, major depression, bipolar disorder, normal aging, epilepsy, traumatic brain injury, post-traumatic stress disorder, Parkinson's disease, Alzheimer's disease, Down syndrome, spinocerebellar ataxia, amyotrophic lateral sclerosis, Huntington's disease, stroke, radiation therapy, chronic stress, and abuse of neuroactive drugs (such as alcohol, opiates, methamphetamine, phencyclidine, and cocaine), retinal degeneration, spinal cord injury, peripheral nerve injury, physiological weight loss associated with various conditions, and cognitive decline associated with normal aging, radiation therapy, and chemotherapy.

In some embodiments, the subject can be a subject in need thereof (e.g., a subject identified as being in need of such treatment, such as a subject having, or at risk of having, one or more of the diseases or conditions described herein). Identifying a subject in need of such treatment can be in the judgment of a subject or a health care professional and can be subjective (e.g. opinion) or objective (e.g. measurable by a test or diagnostic method). In some embodiments, the subject can be a mammal. In certain embodiments, the subject can be a human.

In some embodiments, methods of making the compounds described herein are featured. In embodiments, the methods include taking any one of the intermediate compounds described herein and reacting it with one or more chemical reagents in one or more steps to produce a compound of any of the formulae described herein or a salt (e.g., a pharmaceutically acceptable salt) thereof as defined anywhere herein.

In some embodiments, methods of making the pharmaceutical compositions described herein are featured. In embodiments, the methods include taking any one or more of the compounds of any of the other formulae described herein or a salt (e.g., a pharmaceutically acceptable salt) thereof as defined anywhere herein, and mixing said compound(s) with one or more pharmaceutically acceptable carriers. In one aspect, kits for the treatment (e.g., controlling, relieving, ameliorating, alleviating, or slowing the progression of) or prevention (e.g., delaying the onset of or reducing the risk of developing) of one or more diseases, disorders, or conditions caused by, or associated with insufficient (e.g., aberrant) neurogenesis or unwanted neuronal cell death are featured. The kits include (i) a compound of any of the formulae described herein or a salt (e.g., a pharmaceutically acceptable salt) thereof as defined anywhere herein; and (ii) instructions that include a direction to administer said compound to a subject (e.g., a patient).

In various embodiments, compounds of formula (I), (II), (III), (IV) and (V) can be used in a method for the treatment of a disease, disorder, or condition caused by unwanted neuronal cell death or associated with insufficient neurogenesis in a subject in need thereof. The method can include administering to the subject an effective amount of a compound having formula (I), (II), (III), (VI), or (V) or a pharmaceutically acceptable salt thereof, as defined herein.

The methods can further include detecting a resultant neurotrophism (e.g., neurogenesis; and/or determining that the patient has aberrant neurotrophism, particularly aberrant neurogenesis, particularly aberrant hippocampal and/or hypothalamic neurogenesis, or a disease or disorder associated therewith, particularly by detecting and/or diagnosing the same.

The methods can further include detecting determining that the subject has aberrant neurogenesis or death of neurons or a disease or disorder associated therewith, by detecting the same in said subject.

The methods can further include detecting a resultant hippocampal and/or hypothalamic neurogenesis. The compounds of the presently disclosed embodiments may be used to block neuron cell death in a manner that not only protects mature neurons, but also augments hippocampal neurogenesis by promoting survival of newborn neurons. In some embodiments, the compounds of the presently disclosed embodiments may have a pro-neurogenic activity that is attributable to their ability to impede the death of newborn hippocampal neurons. Instead of stimulating the birth of neuronal stem cells, the compounds may favor their post-birth survival along the differentiation pathway required for them to evolve into properly wired, granular neurons. In the absence of compound administration, upwards of 80% of newborn neurons die. Administration of the compounds of the presently disclosed embodiments can significantly enhance the survival of newborn hippocampal neurons in the adult brain.

The disease, disorder, or condition can be a neuropsychiatric and neurodegenerative disease, including (but not limited to) schizophrenia, major depression, bipolar disorder, normal aging, epilepsy, traumatic brain injury, post-traumatic stress disorder, Parkinson's disease, Alzheimer's disease, Down syndrome, spinocerebellar ataxia, amyotrophic lateral sclerosis, Huntington's disease, stroke, radiation therapy, chronic stress, and abuse of neuro-active drugs (such as alcohol, opiates, methamphetamine, phencyclidine, and cocaine), retinal degeneration, spinal cord injury, peripheral nerve injury, physiological weight loss associated with various conditions, and cognitive decline associated with normal aging, and chemotherapy.

In certain embodiments, the compounds of the presently disclosed embodiments can be used to treat a depressive disorder. For example, the compounds may augment ghrelin-induced hippocampal neurogenesis, thereby treating the depressice disorder. The depressive disorder can be associated with insufficient ghrelin response. In an embodiment, the insufficient ghrelin response may result in impaired or reduced hippocampal neurogenesis.

In some embodiments, the compounds or salt (e.g., a pharmaceutically acceptable salt) thereof provide at least about 27 ($\times 10^{-06}$) BrdU+ cells/mm$^3$ dentate gyms when evaluated in the assay described in conjunction with Table 1 (i.e., evaluated for pro-neurogenic efficacy/neuroprotection in a standard in vivo hippocampal neurogenesis assay at 10 μM concentration in four 12 week old adult male C57/B16 mice.

In some embodiments, the compounds or salt (e.g., a pharmaceutically acceptable salt) thereof provide at least about 19 ($\times 10^{-06}$) BrdU+ cells/mm$^3$ dentate gyms when evaluated in the hippocampal neurogenesis assay described in conjunction with Table 1.

In some embodiments, the compounds or salt (e.g., a pharmaceutically acceptable salt) thereof provide from about 18 to about 30 (e.g., 18-27, 19-26, 20-25, 27-30, 27-29) ($\times 10^{-06}$) BrdU+ cells/mm$^3$ dentate gyms when evaluated in the hippocampal neurogenesis assay described in conjunction with Table 1.

In some embodiments, the compounds or salt (e.g., a pharmaceutically acceptable salt) thereof provide from about 18 to about 26 (e.g., 19-26, 20-25) ($\times 10^{-06}$) BrdU+ cells/mm$^3$ dentate gyms when evaluated in the hippocampal neurogenesis assay described in conjunction with Table 1.

In some embodiments, the compounds or salt (e.g., a pharmaceutically acceptable salt) thereof provide from about 27 to about 30 (e.g., 27-29) ($\times 10^{-06}$) BrdU+ cells/mm$^3$ dentate gyms when evaluated in the hippocampal neurogenesis assay described in conjunction with Table 1.

In embodiments, a composition (e.g., a pharmaceutical composition) can include an amount effective to achieve the levels described above.

In embodiments, any compound, composition, or method described herein can also include any one or more of the other features delineated in the detailed description and/or in the claims.

DETAILED DESCRIPTION

Provided herein are embodiments related generally to stimulating neurogenesis (e.g., post-natal neurogenesis, e.g., post-natal hippocampal and/or hypothalamic neurogenesis) and/or promoting the survival of existing neurons by reducing neuronal cell death.

In certain embodiments, the compounds described herein may be neurotrophic. By "neurotrophic" it is generally meant that the compounds may exert survival-promoting and/or trophic actions on existing neuronal cells, and/or stimulate generation of new neurons.

In certain embodiments, the compounds described herein may be pro-neurogenic and/or neuroprotective. By "pro-neurogenic" it is generally meant that the compounds may be useful in promoting, stimulating and/or enhancing neurogenesis, which is the generation of new neurons. By "neuroprotective" it is generally meant that the compounds may protect or prevent neuronal cells from cell death or apoptosis.

The neurotrophic, pro-neurogenic and/or neuroprotective compounds described herein are attractive candidates as therapeutic agents in many clinical conditions and neuropsychiatric or neurodegenerative diseases such as schizophrenia, major depression, bipolar disorder, normal aging, epilepsy, traumatic brain injury, post-traumatic stress disorder, Parkinson's disease, Alzheimer's disease, Down syndrome, spinocerebellar ataxia, amyotrophic lateral sclerosis, Huntington's disease, stroke, radiation therapy, chronic stress, abuse of a neuro-active drug, retinal degeneration, spinal cord injury, peripheral nerve injury, physiological weight loss associated with various conditions, as well as cognitive decline associated with normal aging, chemotherapy, and the like.

DEFINITIONS

"An effective amount" refers to an amount of a compound that confers a therapeutic effect (e.g., treats, e.g., controls, relieves, ameliorates, alleviates, or slows the progression of; or prevents, e.g., delays the onset of or reduces the risk of developing, a disease, disorder, or condition or symptoms thereof; on the treated subject. The therapeutic effect may be objective (i.e., measurable by some test or marker) or subjective (i.e., subject gives an indication of or feels an effect). An effective amount of the compound described above may range from about 0.01 mg/kg to about 1000 mg/kg, (e.g., from about 0.1 mg/kg to about 100 mg/kg, from about 1 mg/kg to about 100 mg/kg). Effective doses will also vary depending on route of administration, as well as the possibility of co-usage with other agents.

The term "halo" or "halogen" refers to any radical of fluorine, chlorine, bromine or iodine.

In general, and unless otherwise indicated, substituent (radical) prefix names are derived from the parent hydride by either (i) replacing the "ane" in the parent hydride with the suffixes "yl," "diyl," "triyl," "tetrayl," etc.; or (ii) replacing the "e" in the parent hydride with the suffixes "yl," "diyl," "triyl," "tetrayl," etc. (here the atom(s) with the free valence, when specified, is (are) given numbers as low as is consistent with any established numbering of the parent hydride). Accepted contracted names, e.g., adamantyl, naphthyl, anthryl, phenanthryl, furyl, pyridyl, isoquinolyl, quinolyl, and piperidyl, and trivial names, e.g., vinyl, phenyl, and thienyl are also used herein throughout. Conventional numbering/lettering systems are also adhered to for substituent numbering and the nomenclature of fused, bicyclic, tricyclic, polycyclic rings.

The following definitions are used, unless otherwise described. Specific and general values listed below for radicals, substituents, and ranges, are for illustration only; they do not exclude other defined values or other values within defined ranges for the radicals and substituents. Unless otherwise indicated, alkyl, alkoxy, alkenyl, and the like denote both straight and branched groups.

The term "alkyl" refers to a saturated hydrocarbon chain that may be a straight chain or branched chain, containing the indicated number of carbon atoms. For example, $C_{1-6}$ alkyl indicates that the group may have 1 to 6 (inclusive) carbon atoms in it. Any atom can be optionally substituted, e.g., by one or more substituents. Examples of alkyl groups include without limitation methyl, ethyl, n-propyl, isopropyl, and tert-butyl.

As referred to herein, the term "alkoxy" refers to a group of formula —O(alkyl). Alkoxy can be, for example, methoxy (—OCH$_3$), ethoxy, propoxy, isopropoxy, butoxy, iso-butoxy, sec-butoxy, pentoxy, 2-pentoxy, 3-pentoxy, or hexyloxy. As used herein, the term "hydroxyl," employed alone or in combination with other terms, refers to a group of formula —OH.

The term "alkenyl" refers to a straight or branched hydrocarbon chain containing the indicated number of carbon atoms and having one or more carbon-carbon double bonds. Any atom can be optionally substituted, e.g., by one or more substituents. Alkenyl groups can include, e.g., vinyl, allyl, 1-butenyl, and 2-hexenyl. One of the double bond carbons can optionally be the point of attachment of the alkenyl substituent.

The term "alkynyl" refers to a straight or branched hydrocarbon chain containing the indicated number of carbon atoms and having one or more carbon-carbon triple bonds. Alkynyl groups can be optionally substituted, e.g., by one or more substituents. Alkynyl groups can include, e.g., ethynyl, propargyl, and 3-hexynyl. One of the triple bond carbons can optionally be the point of attachment of the alkynyl substituent.

The term "heterocyclyl" refers to a fully saturated monocyclic, bicyclic, tricyclic or other polycyclic ring system having one or more constituent heteroatom ring atoms independently selected from O, N (it is understood that one or two additional groups may be present to complete the nitrogen valence and/or form a salt), or S. The heteroatom or ring carbon can be the point of attachment of the heterocyclyl substituent to another moiety. Any atom can be optionally substituted, e.g., by one or more substituent. Heterocyclyl groups can include, e.g., tetrahydrofuryl, tetrahydropyranyl, piperidyl (piperidine), piperazinyl, morpholinyl (morpholino), pyrrolinyl, and pyrrolidinyl. By way of example, the phrase "heterocyclic ring containing from 5-6 ring atoms, wherein 1-2 of the ring atoms is independently selected from N, NH, N($C_1$-$C_6$ alkyl), NC(O)($C_1$-$C_6$ alkyl), O, and S; and wherein said heterocyclic ring is optionally substituted with 1-3 independently selected $R^{a'''}$ would include (but not be limited to) tetrahydrofuryl, tetrahydropyranyl, piperidyl (piperidino), piperazinyl, morpholinyl (morpholino), pyrrolinyl, and pyrrolidinyl.

The term "cycloalkyl" refers to a fully saturated monocyclic, bicyclic, tricyclic, or other polycyclic hydrocarbon groups. Any atom can be optionally substituted, e.g., by one or more substituents. A ring carbon serves as the point of attachment of a cycloalkyl group to another moiety. Cycloalkyl moieties can include, e.g., cyclopropyl, cyclobutyl, cyclopentyl, cyclohexyl, cycloheptyl, adamantyl, and norbornyl (bicycle[2.2.1]heptyl).

The term "aryl" refers to an aromatic monocyclic, bicyclic (2 fused rings), or tricyclic (3 fused rings), or polycyclic (>3 fused rings) hydrocarbon ring system. One or more ring atoms can be optionally substituted, e.g., by one or more substituents. Aryl moieties include, e.g., phenyl and naphthyl.

The term "heteroaryl" refers to an aromatic monocyclic, bicyclic (2 fused rings), tricyclic (3 fused rings), polycyclic (>3 fused rings) hydrocarbon groups having one or more heteroatom ring atoms independently selected from O, N (it is understood that one or two additional groups may be present to complete the nitrogen valence and/or form a salt), or S. One or more ring atoms can be optionally substituted, e.g., by one or more substituents. Examples of heteroaryl groups include, but are not limited to, 2H-pyrrolyl, 3H-indolyl, acridinyl, benzo[b]thienyl, benzothiazolyl, P-carbolinyl, carbazolyl, coumarinyl, chromenyl, dibenzo[b,d]furanyl, furazanyl, furyl, imidazolyl, imidizolyl, indazolyl, isobenzofuranyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl quinazolinyl quinolyl quinoxalinyl, thiadiazolyl, thianthrenyl, thiazolyl, thienyl, triazolyl, and xanthenyl.

The descriptors "C=O" or "C(O)" refers to a carbon atom that is doubly bonded to an oxygen atom. Similarly, "S(O)" refers to a sulfur atom that is doubly bonded to an oxygen atom.

The term "carboxyl" refers to a group of formula C(O)OH. The term "alkoxycarbonyl" refers to a group of formula. The term "carboxyalkyl" refers to a group of formula (alkyl)-C(O)OH wherein the carboxyl group may be attached to any carbon atom in the alkyl group.

As used herein, the term "cyano," employed alone or in combination with other terms, refers to a group of formula —CN, wherein the carbon and nitrogen atoms are bound together by a triple bond. In general, when a definition for a particular variable includes both hydrogen and non-hydrogen (halo, alkyl, aryl, etc.) possibilities, the term "substituent(s) other than hydrogen" refers collectively to the non-hydrogen possibilities for that particular variable.

The term "substituent" refers to a group "substituted" on, e.g., an alkyl, haloalkyl, cycloalkyl, heterocyclyl, heterocycloalkenyl, cycloalkenyl, aryl, or heteroaryl group at any atom of that group. In one aspect, the substituent(s) on a group are independently any one single, or any combination of two or more of the permissible atoms or groups of atoms delineated for that substituent. In another aspect, a substituent may itself be substituted with any one of the above substituents. Further, as used herein, the phrase "optionally substituted" means unsubstituted (e.g., substituted with an H) or substituted. As used herein, the term "substituted" means that a hydrogen atom is removed and replaced by a substituent. It is understood that substitution at a given atom is limited by valency.

Compounds

Compounds of formula (I)-(V) as defined herein, or any combinations of the definitions of the various groups, are encompassed by the presently disclosed embodiments. Various compounds will be further described in the following examples. It should be understood that these examples are for illustrative purposes only and are not to be construed as limiting the presently disclosed embodiments in any manner.

P7C3-S132: 1-(10,11-dihydro-5H-dibenzo[b,f]azepin-5-yl)-3-(1H-indol-1-yl)propan-2-ol Step 1: Synthesis of 5-(oxiran-2-ylmethyl)-10,11-dihydro-5H-dibenzo[b,f]azepine

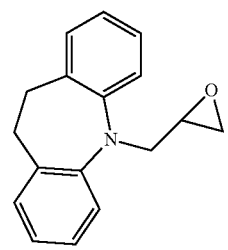 [SMILES: c1ccc2c(c1)CCc1ccccc1N2CC1CO1]

n-BuLi (25.6 mL, 40.9 mmol) was added to a stirred solution of iminodibenzyl (4.00 g, 20.2 mmol) in dry THF (24 mL) at −78° C. and under atmosphere of $N_2$. The mixture was allowed to stir at the same temperature for 20 min and then epibromohydrin (8.48 mL, 102 mmol) was added. The resulting mixture was stirred overnight allowing the reaction to warm up to room temperature. Upon completion, the reaction was partitioned between EtOAc and $H_2O$.

The aqueous layer was washed with EtOAc. The combined organic extracts were washed with brine, dried over MgSO$_4$, filtered, and concentrated in vacuo. The crude residue was purified by chromatography (SiO$_2$, 98:2 Hexanes/EtOAc) to afford the desired product as colorless solid (3.00 g, 59%). The spectroscopic data were in full agreement with those reported in the literature (Levy, O.; Erez, M.; Varon, D.; Keinan, E. *Bioorg. Med. Chem. Lett.* 2001, 11, 2921-2926).

Step 2: 1-(10,11-dihydro-5H-dibenzo[b,f]azepin-5-yl)-3-(1H-indol-1-yl)propan-2-ol. (P7C3-S132)

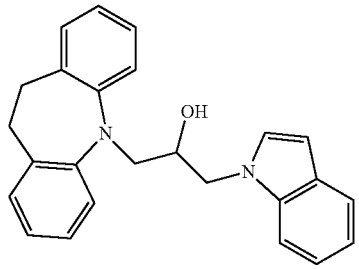 [SMILES: OC(CN1c2ccccc2CCc2ccccc21)Cn1ccc2ccccc21]

Indole (36.0 mg, 0.30 mmol) was added to a suspension of NaH (20.0 mg, 0.48 mmol) in of DMF (5 mL) at 0° C. The mixture was allowed to stir at 0° C. for 10 min and then at room temperature for 30 min. 5-(oxiran-2-ylmethyl)-10,11-dihydro-5H-dibenzo[b,f]azepine (75.0 mg, 0.30 mmol) was then added and the reaction mixture was stirred overnight at room temperature. Upon completion, the reaction was partitioned between EtOAc and H$_2$O. The aqueous layer was washed EtOAc. The combined organic extracts were washed with brine, dried over MgSO$_4$, filtered, and concentrated in vacuum. The crude residue was purified by chromatography (SiO$_2$, 9:1 Hexanes/EtOAc) to afford the desired product as colorless solid (90.3 mg, 82%).

$^1$H NMR (CDCl$_3$, 500 MHz) δ 7.60 (d, 1H, J=7.2 Hz), 7.18-7.05 (m, 7H), 7.05-6.95 (m, 5H), 6.47 (d, 1H, J=2.8 Hz), 4.36 (dd, 1H, J=3.2, 14.4 Hz), 4.20 (m$_c$, 1H), 4.05 (dd, 1H, J=7.5, 14.5 Hz), 3.80 (d, 2H, J=6.5 Hz), 3.27-3.18 (m, 4H), 2.14 (br s, 1H). $^{13}$C NMR (CDCl$_3$, 126 MHz) δ 147.9, 136.4, 134.3, 130.4, 128.9, 128.8, 127.0, 123.6, 121.8, 121.2, 119.9, 119.7, 109.5, 101.8, 68.3, 54.4, 50.6, 32.3. MS (ESI) m/z: 369.0 [M+H]$^+$ ([M+H]$^+$ for C$_{25}$H$_{25}$N$_2$O requires 369.1).

P7C3-S133: 1-(9H-carbazol-9-yl)-3-(10,11-dihydro-5H-dibenzo[b,f]azepin-5-yl)propan-2-ol

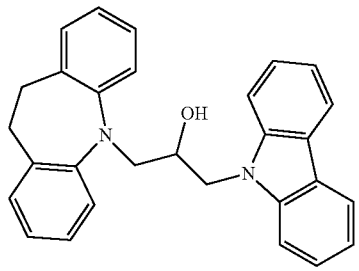 [SMILES: OC(CN1c2ccccc2CCc2ccccc21)Cn1c2ccccc2c2ccccc21]

Following the same procedure as for P7C3-S132, P7C3-S133 was prepared from 5-(oxiran-2-ylmethyl)-10,11-dihydro-5H-dibenzo[b,f]azepine (75.0 mg, 0.30 mmol) and 9H-carbazole (51 mg, 0.3 mmol) with NaH (20.0 mg, 0.48 mmol) in DMF (5 mL) and isolated as a colorless solid (101.4 mg, 81%).

$^1$H NMR (CDCl$_3$, 500 MHz) δ 8.10 (d, 2H, J=7.7 Hz), 7.40 (m$_c$, 2H), 7.29-7.13 (m, 8H), 7.10-7.01 (m, 4H), 4.51 (dd, 1H, J=2.7, 14.7 Hz), 4.43 (m$_c$, 1H), 4.35 (dd, 1H, J=7.9, 14.6 Hz), 4.01 (dd, 1H, J=6.5, 12.7 MHz), 3.90 (dd, 1H, J=6.6, 12.7 MHz), 3.33-3.23 (m, 4H), 2.14 (br s, 1H). $^{13}$C NMR (CDCl$_3$, 126 MHz) δ 147.9, 141.0, 134.3, 130.4, 127.0, 126.0, 123.6, 123.1, 120.4, 119.9, 119.4, 109.1, 68.2, 54.6, 47.7, 32.3. MS (ESI) m/z: 419.0 [M+H]$^+$ ([M+H]$^+$ for C$_{29}$H$_{27}$N$_2$O requires 419.2).

P7C3-S134: 1-(10,11-dihydro-5H-dibenzo[b,f]azepin-5-yl)-3-(phenylthio)propan-2-ol

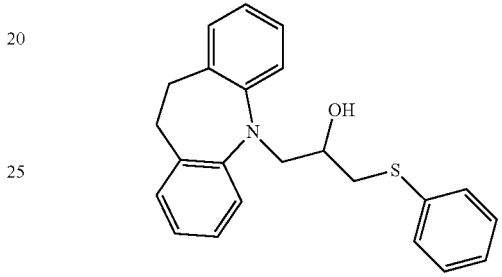

Benzenethiol (34 µL, 0.33 mmol) was added to a solution of 5-(oxiran-2-ylmethyl)-10,11-dihydro-5H-dibenzo[b,f]azepine (75.0 mg, 0.30 mmol) in MeOH (5.6 mL) at room temperature. The reaction mixture was heated to 80° C. and stirred overnight at the same temperature. The reaction was monitored by LC/MS for the consumption of starting material. The reaction was cooled to room temperature, diluted with EtOAc and washed with H$_2$O and brine. The organic layer was dried over Na$_2$SO$_4$, filtered and condensed. The crude residue was purified by chromatography (SiO$_2$, 9:1 Hexanes/EtOAc) to afford the desired product (66.0 mg, 61%).

$^1$H NMR (CDCl$_3$, 500 MHz) δ 7.19-7.05 (m, 11H), 6.96 (m$_c$, 2H), 3.97 (m$_c$, 1H), 3.89 (d, 1H, J=6.3 Hz), 3.26 (dd, 2H, J=4.1, 13.9 Hz), 3.18 (s, 4H), 2.96 (dd, 1H, J=7.3, 13.9 Hz). $^{13}$C NMR (CDCl$_3$, 126 MHz) δ 147.9, 134.2, 130.2, 129.1, 126.8, 126.2, 123.3, 119.9, 66.9, 55.7, 39.2, 32.3. MS (ESI) m/z: 361.9 [M+H]$^+$ ([M+H]$^+$ for C$_{23}$H$_{24}$NOS requires 362.1).

P7C3-S135: 1-(10,11-dihydro-5H-dibenzo[b,f]azepin-5-yl)-3-phenoxypropan-2-ol

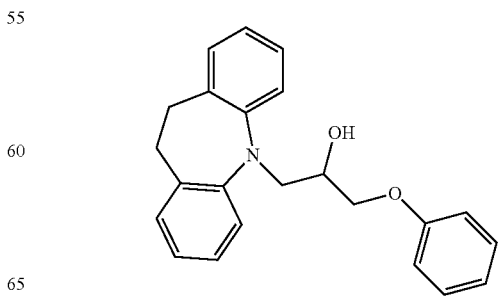

To a stirred solution of iminodibenzyl (75 mg, 0.38 mmol) in dry THF (1.5 mL) was added n-BuLi (0.3 mL, 0.68 mmol, 2.5 M in hexanes) at −78° C. and the resulting mixture was stirred for 30 min. 2-(phenoxymethyl)oxirane (0.13 mL, 0.95 mL) was added and the reaction was allowed to warm slowly to ambient temperature and stirred overnight. Upon completion, the reaction was quenched with saturated aqueous $NH_4Cl$ and the mixture was extracted with EtOAc. The combined organic layers were washed with brine, dried over $Na_2SO_4$, filtered, and concentrated. The crude residue was purified by chromatography ($SiO_2$, 9:1 Hexanes/EtOAc) to afford the desired product (92.0 mg, 70%).

$^1$H NMR ($CDCl_3$, 500 MHz) δ 7.29 (t, 2H, J=8.0 Hz), 7.20-7.11 (m, 6H), 7.02-6.95 (m, 3H), 6.88 (d, 2H, J=8.5 Hz), 4.23 ($m_c$, 1H), 4.11 (dd, 2H, J=3.7, 9.6 Hz), 4.06-3.95 (m, 2H), 3.21 (s, 4H). $^{13}$C NMR ($CDCl_3$, 126 MHz) δ 158.6, 148.0, 134.4, 130.2, 129.6, 126.8, 123.3, 121.2, 119.9, 114.6, 70.3, 67.4, 53.7, 32.2. MS (ESI) m/z: 346.0 $[M+H]^+$ ($[M+H]^+$ for $C_{23}H_{24}NO_2$ requires 346.1).

P7C3-S139: 1-(10,11-dihydro-5H-dibenzo[b,f]azepin-5-yl)-3-(dimethylamino)propan-2-ol

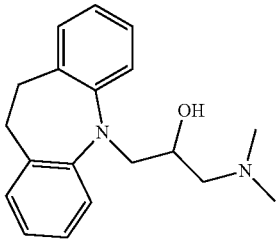 [SMILES: CN(C)CC(O)CN1c2ccccc2CCc2ccccc21]

5-(Oxiran-2-ylmethyl)-10,11-dihydro-5H-dibenzo[b,f]azepine (75 mg, 0.3 mmol) was added to a 25 mL scintillation vial followed by $Me_2NH \cdot HCl$ (37.0 mg, 0.45 mmol) and $K_2CO_3$ (125 mg, 0.9 mmol). The vial was heated to reflux for 2 h. Upon completion the reaction was cooled to room temperature, the solids were filtered off and the solvent was evaporated in vacuum. The crude residue was purified by chromatography ($SiO_2$, 98:2 $CH_2Cl_2$/MeOH+1% $NH_4OH$) to afford the desired product as a white solid (76.0 mg, 86%).

$^1$H NMR ($CDCl_3$, 500 MHz) δ 7.10-7.00 (m, 6H), 6.87 ($m_c$, 2H), 3.86-3.75 (m, 2H), 3.73 (brs, 1H), 3.58 (dd, 1H, J=6.2, 12.2 Hz), 3.11 (s, 4H), 2.41-2.28 (m, 2H), 2.09 (s, 6H). $^{13}$C NMR ($CDCl_3$, 126 MHz) δ 148.0, 134.1, 129.9, 126.5, 122.8, 119.8, 65.3, 64.4, 55.3, 45.6, 32.1. MS (ESI) m/z: 297.0 $[M+H]^+$ ($[M+H]^+$ for $C_{19}H_{25}N_2O$ requires 297.1).

P7C3-S140: 1-amino-3-(10,11-dihydro-5H-dibenzo[b,f]azepin-5-yl)propan-2-ol

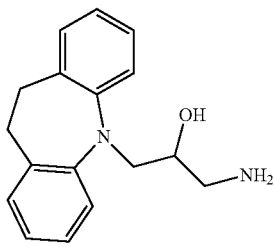 [SMILES: NCC(O)CN1c2ccccc2CCc2ccccc21]

5-(Oxiran-2-ylmethyl)-10,11-dihydro-5H-dibenzo[b,f]azepine (262 mg, 1.04 mmol) was added to a 25 mL scintillation vial followed by $NH_3$-MeOH (7N, 6.0 mL). The vial was heated to reflux for 12 h. Upon completion the reaction was cooled to room temperature and concentrated under reduced pressure to remove the remaining methanol. The crude residue was purified by chromatography ($SiO_2$, 98:2 $CH_2Cl_2$/MeOH+1% $NH_4OH$) to afford the desired product as an amorphous yellow foam (76.0 mg, 86%).

$^1$H NMR ($CDCl_3$, 500 MHz) δ 7.10-7.02 (m, 6H), 6.88 ($m_c$, 2H), 3.76 (dd, 1H, J=6.0, 12.1 Hz), 3.68 (brs, 1H), 3.63 (dd, 1H, J=6.2, 12.1 Hz), 3.31 (brs, 2H), 3.11 (s, 4H), 2.78 (d, 1H, J=13.1 Hz), 2.55 (dd, 1H, J=7.3, 13.1 Hz). $^{13}$C NMR ($CDCl_3$, 126 MHz) δ 148.1, 134.2, 130.1, 126.7, 123.1, 120.0, 67.3, 67.2, 55.1, 53.6, 53.5, 32.2. MS (ESI) m/z: 269.0 $[M+H]^+$ ($[M+H]^+$ for $C_{17}H_{21}N_2O$ requires 269.1).

P7C3-S143: 1-(10,11-dihydro-5H-dibenzo[b,f]azepin-5-yl)-3-(methylamino)propan-2-ol

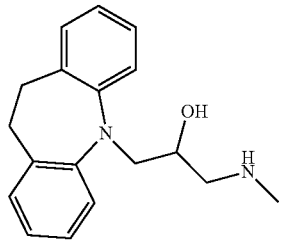 [SMILES: CNCC(O)CN1c2ccccc2CCc2ccccc21]

Following the same procedure as for P7C3-S139, P7C3-S143 was prepared from 5-(oxiran-2-ylmethyl)-10,11-dihydro-5H-dibenzo[b,f]azepine (75.0 mg, 0.30 mmol) and $MeNH_2 \cdot HCl$ (30.4 mg, 0.45 mmol) with $K_2CO_3$ (125 mg, 0.9 mmol) and isolated as a white solid (57.0 mg, 68%).

$^1$H NMR ($CDCl_3$, 500 MHz) δ 7.21-7.10 (m, 6H), 6.98 ($m_c$, 2H), 3.98 (brs, 1H), 3.91 (dd, 1H, J=5.7, 12.9 Hz), 3.84 (dd, 1H, J=7.2, 12.9 Hz), 3.53 (dd, 1H, J=3.4, 9.6 Hz), 3.43 (dd, 1H, J=5.7, 9.6 Hz), 3.37 (s, 3H), 3.20 (s, 4H), 2.51 (d, 1H, J=3.0 Hz).

$^{13}$C NMR ($CDCl_3$, 126 MHz) δ 148.1, 134.3, 130.1, 126.7, 123.1, 120.0, 75.0, 67.6, 59.4, 53.7, 32.2.

MS (ESI) m/z: 284.0 $[M+H]^+$ ($[M+H]^+$ for $C_{18}H_{23}N_2O$ requires 283.1).

P7C3-S144: 1-(10,11-dihydro-5H-dibenzo[b,f]azepin-5-yl)-3-(isopropylamino)propan-2-ol

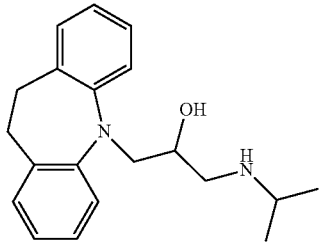 [SMILES: CC(C)NCC(O)CN1c2ccccc2CCc2ccccc21]

5-(Oxiran-2-ylmethyl)-10,11-dihydro-5H-dibenzo[b,f]azepine (100 mg, 0.4 mmol) was added to a 25 mL scintillation vial followed by isopropanol (2 mL) and isopropylamine (2 mL, 23.3 mmol). The vial was heated to reflux for 12 h. Upon completion the reaction was cooled to room temperature, and the solvent was evaporated in vacuum. The crude residue was recrystallized (Hexanes/EtOAc) to give the desired product as a white solid (74.0 mg, 60%).

$^1$H NMR (CDCl$_3$, 500 MHz) δ 7.16-7.08 (m, 6H), 6.94 (m$_c$, 2H), 3.86 (dd, 1H, J=6.6, 11.9 Hz), 3.81 (brs, 1H), 3.74 (dd, 1H, J=5.0, 11.9 Hz), 3.18 (s, 4H), 2.82 (dd, 1H, J=2.9, 11.9 Hz), 2.73 (m, 1H), 2.54 (dd, 1H, J=7.5, 11.9 Hz), 2.14 (brs, 1H), 1.01 (d, 6H, J=6.2 Hz). $^{13}$C NMR (CDCl$_3$, 126 MHz) δ 148.2, 134.3, 130.1, 126.7, 123.1, 120.1, 67.2, 55.3, 50.1, 49.0, 32.3, 23.2, 23.1. MS (ESI) m/z: 311.0 [M+H]$^+$ ([M+H]$^+$ for C$_{20}$H$_{27}$N$_2$O requires 311.2).

P7C3-S145: 1-(tert-butylamino)-3-(10,11-dihydro-5H-dibenzo[b,f]azepin-5-yl)propan-2-ol

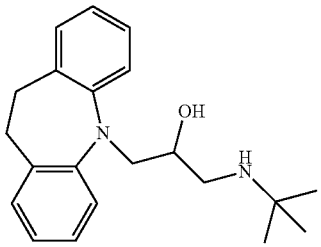 [SMILES: CC(C)(C)NCC(O)CN1c2ccccc2CCc2ccccc21]

5-(Oxiran-2-ylmethyl)-10,11-dihydro-5H-dibenzo[b,f]azepine (100 mg, 0.4 mmol) was added to a 25 mL scintillation vial followed by tert-butanol (1 mL) and tert-butylamine (3 mL, 28.5 mmol). The vial was heated to reflux for 12 h. Upon completion the reaction was cooled to room temperature, and the solvent was evaporated in vacuum. The crude residue was purified by chromatography (SiO$_2$, 98:2 CH$_2$Cl$_2$/MeOH+1% NH$_4$OH) to afford the desired product as a white solid (123 mg, 95%).

$^1$H NMR (CDCl$_3$, 500 MHz) δ 7.18-7.07 (m, 6H), 6.95 (m$_c$, 2H), 3.94 (dd, 1H, J=6.0, 12.6 Hz), 3.76 (brs, 1H), 3.69 (dd, 1H, J=6.5, 12.6 Hz), 3.19 (s, 4H), 2.79 (dd, 1H, J=2.7, 11.7 Hz), 2.50 (dd, 1H, J=7.9, 11.7 Hz), 1.05 (s, 9H). $^{13}$C NMR (CDCl$_3$, 126 MHz) δ 148.3, 134.3, 130.0, 126.7, 123.0, 120.1, 67.5, 55.3, 50.3, 46.2, 32.3, 29.2.

MS (ESI) m/z: 325.0 [M+H]$^+$ ([M+H]$^+$ for C$_{21}$H$_{29}$N$_2$O requires 325.2).

P7C3-S148: 3-(10,11-dihydro-5H-dibenzo[b,f]azepin-5-yl)-2-fluoro-N,N-dimethylpropan-1-amine

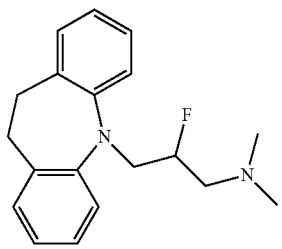 [SMILES: CN(C)CC(F)CN1c2ccccc2CCc2ccccc21]

An oven dried 20 mL scintillation vial containing 1-(10,11-dihydro-5H-dibenzo[b,f]azepin-5-yl)-3-(dimethylamino)propan-2-ol (47.0 mg, 0.16 mmol) was purged with N$_2$ and charged with anhydrous CH$_2$Cl$_2$ (9.0 mL, 0.018 M). The sealed vial was cooled in a dry ice acetone bath before the dropwise addition of morpholinosulfur trifluoride (morpho-DAST, 39 µL, 0.32 mmol). The reaction temperature was maintained at 78° C. for an hour and then slowly warmed to room temperature and stirred overnight. The reaction was quenched with saturated NaHCO$_3$ solution and diluted with CH$_2$Cl$_2$ and extracted three times. The combined organics were dried over Na$_2$SO$_4$, filtered and condensed. The crude residue was purified by chromatography (SiO$_2$, 8:2 Hexanes/EtOAc) to afford the desired product (12.3 mg, 26%).

$^1$H NMR (CDCl$_3$, 500 MHz) δ 7.187-7.08 (m, 6H), 6.94 (m$_c$, 2H), 4.81-4.64 (m, 1H), 4.00 (d, 1H, J=6.0 Hz), 3.97 (t, 1H, J=5.6 Hz), 3.17 (s, 4H), 2.64-2.56 (m, 1H), 2.56-2.52 (m, 1H), 2.23 (s, 6H). $^{13}$C NMR (CDCl$_3$, 126 MHz) δ 147.9, 134.7, 130.1, 126.7, 123.1, 120.2, 90.5, 88.7, 62.1 (d, J=20.6 Hz), 53.9 (d, J=25.8 Hz), 46.3, 32.1. MS (ESI) m/z: 299.0 [M+H]$^+$ ([M+H]$^+$ for C$_{19}$H$_{24}$FN$_2$ requires 299.1).

P7C3-S149: 1-(10,11-dihydro-5H-dibenzo[b,f]azepin-5-yl)-3-fluoro-N,N-dimethylpropan-2-amine

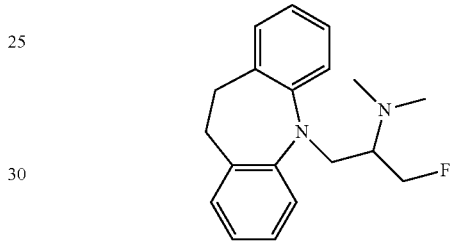

1-(10,11-dihydro-5H-dibenzo[b,f]azepin-5-yl)-3-fluoro-N,N-dimethylpropan-2-amine was obtained as main product in the synthesis of (P7C3-S148) (28.5 mg, 60%).

$^1$H NMR (CDCl$_3$, 500 MHz) δ 7.17-7.08 (m, 6H), 6.95 (m$_c$, 2H), 4.61 (dd, 2H, J=3.7, 47.8 Hz), 4.09 (dt, 1H, J=3.3, 12.5 Hz), 3.62 (m, 1H), 3.16 (s, 4H), 2.94 (ddd, 1H, J=4.3, 9.4, 25.6 Hz), 2.42 (s, 6H). $^{13}$C NMR (CDCl$_3$, 126 MHz) δ 148.3, 134.4, 130.2, 126.7, 123.0, 119.8, 61.0, 60.9, 48.4, 42.0, 32.2. MS (ESI) m/z: 299.0 [M+H]$^+$ ([M+H]$^+$ for C$_{19}$H$_{24}$FN$_2$ requires 299.1).

P7C3-S152: 3-(10,11-dihydro-5H-dibenzo[b,f]azepin-5-yl)-2-fluoro-N-methylpropan-1-amine Step 1. Synthesis of N-(3-(10,11-dihydro-5H-dibenzo[b,f]azepin-5-yl)-2-hydroxypropyl)-N-methyl-4-nitrobenzenesulfonamide

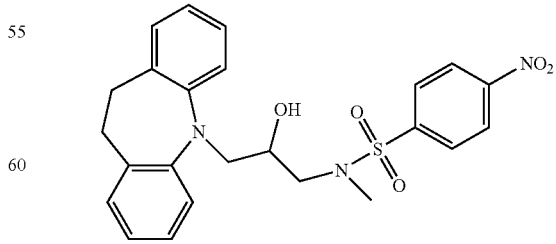

A heterogeneous mixture of N-methyl-4-nitrobenzenesulfonamide (95.0 mg, 0.44 mmol) (synthesized following a reported procedure: Harshani R. L.; Kazi, A; Ge, Y; Guida, W. C.; Sebti, S.; Luo, Y.; Kendig, R.; Jain, S.; Daniel, K.; Santiago, D., *Bioorg. Med. Chem.* 2010, 18, 5576-5592) in toluene (3.4 mL, 0.13 M) under a $N_2$ atmosphere was cooled in a dry ice/acetone bath before dropwise addition of n-BuLi (0.240 mL of 2.5 M in hexanes, 0.60 mmol). The reaction was stirred at 78° C. for 20 minutes before addition of 5-(oxiran-2-ylmethyl)-10,11-dihydro-5H-dibenzo[b,f] azepine (100 mg, 0.4 mmol). The heterogeneous mixture was stirred at room temperature for 5 min before heating at 100° C. for 72 h. The cooled reaction was diluted with EtOAc and washed 3×5% acetic acid solution, followed by a brine wash. The organic layer was dried over $Na_2SO_4$, filtered and condensed. The crude residue was purified by chromatography ($SiO_2$, 7:3 Hexanes/EtOAc) to afford the desired product (45.0 mg, 25%).

$^1$H NMR (CDCl$_3$, 500 MHz) δ 8.32 (d, 2H, J=8.6 Hz), 7.90 (d, 2H, J=8.6 Hz), 7.20-7.07 (m, 6H), 6.98 (m$_c$, 2H), 3.99-3.91 (m, 2H), 3.75 (m$_c$, 1H), 3.34-3.27 (m, 1H), 3.16 (s, 4H), 2.85 (s, 3H). $^{13}$C NMR (CDCl$_3$, 126 MHz) δ 147.8, 134.2, 130.3, 128.6, 126.9, 124.5, 123.6, 119.9, 63.3, 54.5, 54.3, 37.0, 32.2. MS (ESI) m/z: 467.9 [M+H]$^+$ ([M+H]$^+$ for $C_{24}H_{26}N_3O_5S$ requires 468.1).

Step 2. Synthesis of N-(3-(10,11-dihydro-5H-dibenzo[b,f]azepin-5-yl)-2-fluoropropyl)-N-methyl-4-nitrobenzenesulfonamide

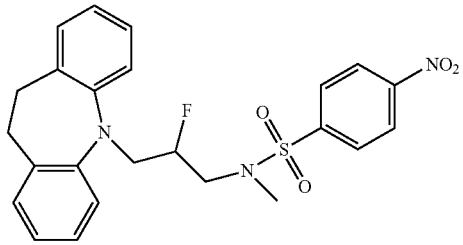 [SMILES: CN(CC(F)CN1c2ccccc2CCc2ccccc21)S(=O)(=O)c1ccc([N+](=O)[O-])cc1]

This intermediate was prepared analogously to P7C3-S148. The crude product was carried forward without further purification.

$^1$H NMR (CDCl$_3$, 500 MHz) δ 8.24 (d, 2H, J=8.8 Hz), 7.77 (d, 2H, J=8.8 Hz), 7.20-7.05 (m, 6H), 7.01 (m$_c$, 2H), 4.76-4.55 (m, 1H), 4.10 (td, 1H, J=5.8, 13.4 Hz), 3.87 (td, 1H, J=6.6, 13.9, 14.8 Hz), 3.78-3.60 (m, 2H), 3.20 (s, 4H), 2.87 (s, 3H). $^{13}$C NMR (CDCl$_3$, 126 MHz) δ 147.6, 134.8, 130.4, 128.4, 126.8, 124.5, 123.6, 119.9, 91.0, 89.2, 67.0, 52.7 (dd, J=23.7, 32.1 Hz), 44.4, 36.5, 32.0. MS (ESI) m/z: 469.9 [M+H]$^+$ ([M+H]$^+$ for $C_{24}H_{25}FN_3O_4S$ requires 470.1).

Step 3. Synthesis of 3-(10,11-dihydro-5H-dibenzo[b,f]azepin-5-yl)-2-fluoro-N-methylpropan-1-amine (P7C3-S152)

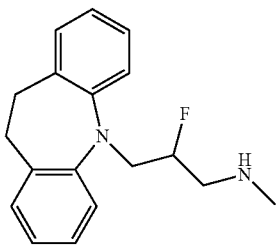 [SMILES: CNCC(F)CN1c2ccccc2CCc2ccccc21]

To a vial containing N-(3-(10,11-dihydro-5H-dibenzo[b,f]azepin-5-yl)-2-fluoropropyl)-N-methyl-4-nitrobenzenesulfonamide (53.2 mg, 0.113 mmol) was added lithium hydroxide (12.2 mg, 0.510 mmol), DMF (2.0 mL, 0.06 M) and mercaptoacetic acid (16.0 µL, 0.227 mmol). After stirring at room temperature for 1 h the reaction mixture was diluted with EtOAc and washed sequentially with $H_2O$, saturated aqueous $NaHCO_3$, $H_2O$ (3×) and brine. The organic layer was dried over $Na_2SO_4$, filtered and condensed. The crude residue was purified by chromatography ($SiO_2$, 98:2 $CH_2Cl_2$/MeOH+1% $Et_3N$) to afford the desired product (14.5 mg, 47%).

$^1$H NMR (CDCl$_3$, 500 MHz) δ 7.09-6.95 (m, 6H), 6.86 (m$_c$, 2H), 4.77-4.55 (m, 1H), 3.97 (td, 1H, J=6.6, 13.8 Hz), 3.85 (m$_c$, 1H), 3.07 (s, 4H), 2.82-2.75 (m, 1H), 2.74-2.68 (m, 1H), 2.31 (s, 3H). $^{13}$C NMR (CDCl$_3$, 126 MHz) δ 147.6, 134.5, 130.0, 126.6, 123.2, 119.9, 90.4, 88.7, 53.3 (dd, J=22.7, 46.9 Hz), 49.0 (dp, J=21.4, 42.9 Hz), 35.6, 31.9.

MS (ESI) m/z: 285.0 [M+H]$^+$ ([M+H]$^+$ for $C_{18}H_{22}FN_2$ requires 285.1).

P7C3-S158: 1-(10,11-dihydro-5H-dibenzo[b,f]azepin-5-yl)-3-((3-methoxyphenyl)amino)propan-2-ol

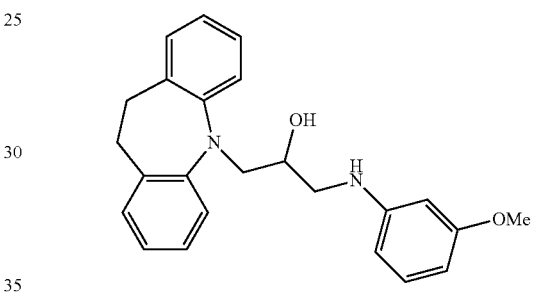

Following the same procedure as for P7C3-S135, P7C3-S158 was prepared from iminodibenzyl (68.2 g, 0.35 mmol) and 3-methoxy-N-(oxiran-2-ylmethyl)aniline (75.1 mg, 0.42 mmol) with n-BuLi (0.167 mL of 2.5 M in hexanes, 0.42 mmol) in dry THF (1 mL) and isolated after chromatography ($SiO_2$, 7:3 Hexanes/EtOAc) (10.5 mg, 8%).

$^1$H NMR (CDCl$_3$, 400 MHz) δ 7.17-7.09 (m, 6H), 7.04 (m$_c$, 2H), 7.00-6.94 (m, 2H), 6.30 (dd, 1H, J=2.3, 8.2 Hz), 6.22-6.15 (m, 2H), 4.07 (m$_c$, 1H), 3.94 (dd, 1H, J=4.9, 13.0 Hz), 3.82 (dd, 1H, J=8.0, 13.0 Hz), 3.74 (s, 3H), 3.38 (dd, 1H, J=3.4, 12.8 Hz), 3.20 (s, 4H), 3.12 (dd, 1H, J=7.0, 12.8 Hz). $^{13}$C NMR (CDCl$_3$, 126 MHz) δ 148.0, 134.3, 130.3, 130.2, 126.8, 123.5, 119.9, 106.6, 103.7, 99.5, 67.1, 55.2, 54.9, 48.2, 32.3.

MS (ESI) m/z: 375.0 [M+H]$^+$ ([M+H]$^+$ for $C_{24}H_{27}N_2O_2$ requires 375.2).

P7C3-S162: 3,6-dibromo-9H-carbazole

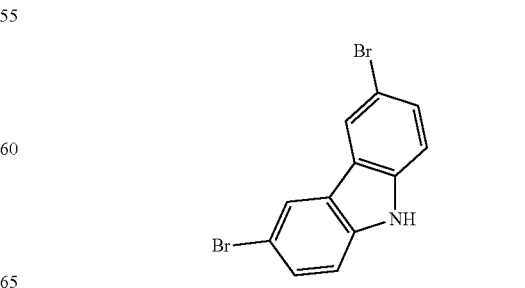

This analog was purchased from SigmaAldrich

P7C3-S163: 3,6-dibromo-9-methyl-9H-carbazole

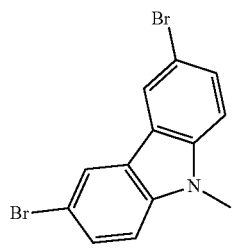 [SMILES: Cn1c2ccc(Br)cc2c2cc(Br)ccc21]

The title compound was prepared from P7C3-S162 by methylation with NaH and methyl iodide.

The ¹H NMR data was consistent with that reported in Eur. J. Med. Chem. 1997 (32) 781.

P7C3-S164: ethyl 2-(3,6-dibromo-9H-carbazol-9-yl)acetate

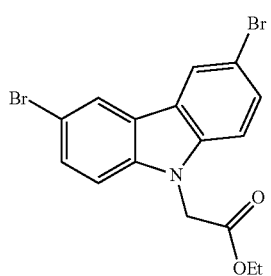 [SMILES: CCOC(=O)Cn1c2ccc(Br)cc2c2cc(Br)ccc21]

Sodium Hydride was added to a stirred solution of 3,6-dibromocarbazole (250 mg, 0.77 mmol) in DMF (4 ml). The solution was stirred for 30 minutes before the dropwise addition of ethyl chloroacetate. After 12 hours water was added and a fine white precipitate formed which was filtered and rinsed with water and hexanes to afford the desired ethyl ester in 93% yield.

¹H NMR (500 MHz, CDCl$_3$) δ 8.15 (s, 2H), 7.56 (d, J=8.6 Hz, 2H), 7.21 (d, J=8.5 Hz, 2H), 4.94 (s, 2H), 4.20 (q, J=6.3 Hz, 2H), 1.26-1.18 (m, 3H). ESI m/z: 409.7 ([M+H]$^+$, C$_{16}$H$_{13}$Br$_2$NO$_2$ requires 409.9)

P7C3-S165: 2-(3,6-dibromo-9H-carbazol-9-yl)acetic acid

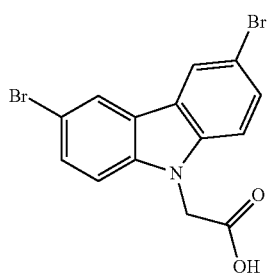 [SMILES: O=C(O)Cn1c2ccc(Br)cc2c2cc(Br)ccc21]

Ethyl 2-(3,6-dibromo-9H-carbazol-9-yl)acetate (50 mg, 0.12 mmol) was dissolved in 0.6 ml of THF. To this stirred solution was added 0.4 ml of methanol, 0.2 ml of water, and lithium hydroxide (14.5 mg, 0.6 mmol). After 1 hour all starting material had been consumed. The solution was acidified with 1N HCl. Upon reaching a pH of about 4 precipitate had formed which was collected and rinsed with fresh water to afford the desired acid in 95% yield.

¹H NMR (500 MHz, Acetone-d$_6$) δ 8.41 (s, 2H), 7.62 (dt, J=8.6, 1.7 Hz, 2H), 7.58 (dd, J=8.7, 1.5 Hz, 2H), 5.31 (d, J=1.6 Hz, 2H). ESI m/z: 381.7 ([M+H]$^+$, C$_{14}$H$_9$Br$_2$NO$_2$ requires 381.9)

P7C3-S169: 1-(3,6-dibromo-9H-carbazol-9-yl)-2-methylpropan-2-ol

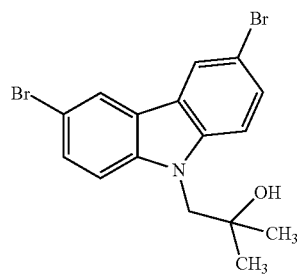 [SMILES: CC(C)(O)Cn1c2ccc(Br)cc2c2cc(Br)ccc21]

A flask was charged with ethyl 2-(3,6-dibromo-9H-carbazol-9-yl)acetate (100 mg, 0.243 mmol) and purged with nitrogen gas. Anhydrous THF (2 ml) was added and the solution was cooled to −78° C. in a dry ice/acetone bath. Methyl magnesium bromide (0.19 mL of a 3M ether solution) was added drop wise. The reaction was warmed to room temperature and stirred overnight. Upon completion the reaction was cooled to 0° C. and NH$_4$Cl (sat.) was added. The mixture was extracted with ethyl acetate, washed with water, brine and dried over magnesium sulfate. The crude mixture was purified on SiO$_2$ (10% EtOAc/hexanes. Isolated yield was 69%.

¹H NMR (500 MHz, CDCl$_3$) δ 8.14 (s, 2H), 7.55 (d, J=8.7 Hz, 2H), 7.41 (d, J=8.7 Hz, 2H), 4.24 (s, 2H), 1.35 (s, 6H). ESI m/z: 439.95 ([M+HCOO]$^-$, C$_{16}$H$_{15}$Br$_2$NO requires 394.95)

P7C3-S170: 1,3-bis(10,11-dihydro-5H-dibenzo[b,f]azepin-5-yl)propan-2-ol

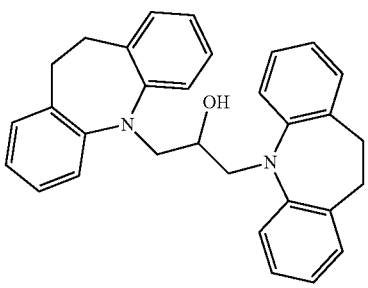 [SMILES: OC(CN1c2ccccc2CCc2ccccc21)CN1c2ccccc2CCc2ccccc21]

P7C3-S170 was obtained as a by-product in the synthesis of 5-(oxiran-2-ylmethyl)-10,11-dihydro-5H-dibenzo[b,f]azepine and isolated as a white solid (74.7 mg, 33%).

¹H NMR (CDCl₃, 500 MHz) δ 7.14 (d, 4H, J=7.3 Hz), 7.03 (d, 4H, J=7.1 Hz), 6.99-6.84 (m, 8H), 4.10 (m_c, 1H), 3.97 (dd, 2H, J=5.3, 12.9 Hz), 3.79 (dd, 2H, J=7.2, 12.9 Hz), 3.24 (m_c, 8H). ¹³C NMR (CDCl₃, 126 MHz) δ 148.0, 134.1, 130.1, 126.7, 123.1, 119.7, 65.4, 55.2, 32.3. MS (ESI) m/z: 447.0 [M+H]⁺ ([M+H]⁺ for $C_{31}H_{31}N_2O$ requires 447.2).

P7C3-S171:
2-(3,6-dibromo-9H-carbazol-9-yl)ethanol

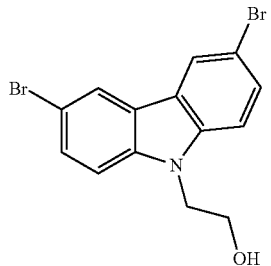 [SMILES: OCCn1c2ccc(Br)cc2c2cc(Br)ccc21]

Ethyl 2-(3,6-dibromo-9H-carbazol-9-yl)acetate (50 mg, 0.12 mmol) was dissolved in 1 ml of THF. LiBH₄ (5.3 mg, 0.24 mmol) was added, and the mixture was heated to 60° C. for 45 minutes. The reaction was cooled to room temperature and 10% NaHCO₃ was added. This material was extracted with EtOAc, washed with 1N HCl, H₂O, and brine. The crude material did not require further purification.
¹H NMR (500 MHz, CDCl₃) δ 8.15 (s, 2H), 7.56 (d, J=8.7 Hz, 2H), 7.35 (d, J=8.7 Hz, 2H), 4.44 (t, J=4.8 Hz, 2H), 4.05 (t, J=4.8 Hz, 2H). ESI m/z: 367.7 ([M+H]⁺, $C_{14}H_{11}Br_2NO$ requires 367.92)

P7C3-S185: 1-(naphthalen-1-ylamino)-3-(2-phenyl-1H-indol-1-yl)propan-2-ol

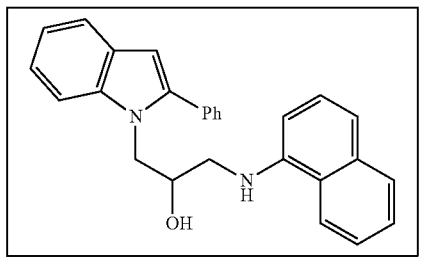 [SMILES: OC(CNc1cccc2ccccc12)Cn1c(-c2ccccc2)cc2ccccc21]

The title compound was synthesized according to Asso et al., Chem Med Chem, 2008, (3) 1530.

P7C3-S189: 9-(3-azido-2-fluoropropyl)-3,6-dibromo-9H-carbazole

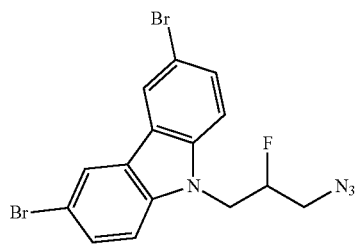 [SMILES: [N-]=[N+]=NCC(F)Cn1c2ccc(Br)cc2c2cc(Br)ccc21]

The title compound was prepared by opening 3,6-dibromo-9-(oxiran-2-ylmethyl)-9H-carbazole with NaN₃ in ethanol, followed by fluorination according to Representative Procedure 4.
MS (ESI) m/z: 468.6, [M+formate]–, $C_{15}H_{11}Br_2FN_4$ requires 423.9

P7C3-S193: Melatonin

This compound was purchased from SigmaAldrich.

P7C3-S199: Vinpocetine

This compound was purchased from SigmaAldrich

P7C3-S200: PK 11195

This compound was purchased from SigmaAldrich

P7C3-S201: N,N-Dihexyl-2-(4-fluorophenyl)indole-3-acetamide, also known as FGIN-1-27

This compound was purchased from SigmaAldrich.

P7C3-S203: 4'-chlorodiazepam

This compound was purchased from SigmaAldrich.

P7C3-S207: 5-bromo-DL-tryptophan

This compound was purchased from SigmaAldrich.

P7C3-S206:
6-bromo-9H-pyrido[3,4-b]indole-3-carboxylic acid

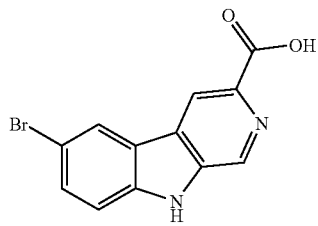 [SMILES: O=C(O)c1cc2c(cn1)[nH]c1ccc(Br)cc12]

Ethyl 6-bromo-9H-pyrido[3,4-b]indole-3-carboxylate was suspended in 10% NaOH_(aq.) and heated to reflux for 3 hours. Upon completion the reaction was cooled to room temperature and acidified with ice cold HCl_(conc.). The temperature was maintained at 0° C. and stirred for 1 hour. The precipitate was filtered, rinsed with water, and dried under vacuum to afford the desired compound in 91% yield.
¹H NMR (500 MHz, DMSO-d₆) δ 12.92 (s, 1H), 9.30 (s, 1H), 9.18 (s, 1H), 8.90 (s, 1H), 7.87 (d, J=8.7 Hz, 1H), 7.80 (d, J=8.8 Hz, 1H). ESI m/z: 290.8 ([M+H]⁺, $C_{12}H_7BrN_2O_2$ requires 290.97)

P7C3-S209: Synthesis of
3-bromo-6-methoxy-9H-carbazole

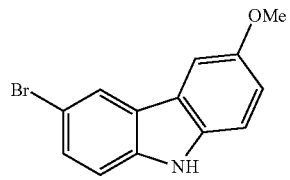 [SMILES: COc1ccc2[nH]c3ccc(Br)cc3c2c1]

3-Methoxy-9H-carbazole (Bedford, R. B.; Betham, M. *J. Org. Chem.* 2006, 71, 9403-9410) (0.029 g, 0.147 mmol) was dissolved in dry DMF (0.28 mL) and NBS (0.026 g, 0.147 mmol) was added to the solution. The reaction mixture was stirred at room temperature for 2 h under absence of light. The solution was poured into water (2 mL), filtered and washed with water. The title compound was isolated as a grey solid (0.033 g, 82%).

$^1$H NMR (CDCl$_3$, 400 MHz) δ 8.13 (s, 1H), 7.91 (brs, 1H), 7.50-7.43 (m, 2H), 7.30 (d, 1H, J=8.7 Hz), 7.25 (d, 1H, J=5.6 Hz), 7.08 (d, 1H, J=8.7 Hz), 3.91 (s, 3H). MS (ESI) m/z 276.9 [M+H]$^+$ ([M+H]$^+$, C$_{13}$H$_{11}$BrNO requires 276.0).

P7C3-S210:
2-(10,11-dihydro-5H-dibenzo[b,f]azepin-5-yl)acetic acid

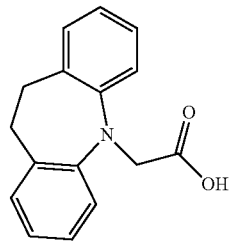 [SMILES: O=C(O)CN1c2ccccc2CCc2ccccc21]

P7C3-S210 was prepared analogously to P7C3-S165 (276 mg, 85%).

$^1$H NMR (CDCl$_3$, 500 MHz) δ 7.15-7.09 (m, 4H), 7.03 (d, 2H, J=7.9 Hz), 6.96 (t, 2H, J=7.3 Hz), 4.58 (s, 2H), 3.21 (s, 4H). $^{13}$C NMR (CDCl$_3$, 126 MHz) δ 175.5, 147.5, 134.5, 130.2, 126.8, 123.4, 119.6, 54.6, 32.6. MS (ESI) m/z: 254.0 [M+H]$^+$ ([M+H]$^+$ for C$_{16}$H$_{16}$NO$_2$ requires 254.1).

P7C3-S211:
2-(3,6-dibromo-9H-carbazol-9-yl)propanoic acid

Step 1: ethyl 2-(3,6-dibromo-9H-carbazol-9-yl)propanoate

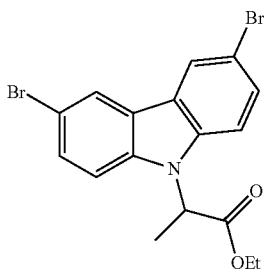 [SMILES: CCOC(=O)C(C)n1c2ccc(Br)cc2c2cc(Br)ccc21]

Synthesized analogously to P7C3-S164.

$^1$H NMR (500 MHz, CDCl$_3$) δ 8.15 (d, J=1.8 Hz, 2H), 7.54 (dd, J=8.7, 1.9 Hz, 2H), 7.26 (d, J=8.7 Hz, 2H), 5.31 (q, J=7.3 Hz, 1H), 4.17 (q, J=7.1 Hz, 2H), 1.80 (d, J=7.3 Hz, 3H), 1.12 (t, J=7.1 Hz, 3H). ESI m/z: 423.7 ([M+H]$^+$, C$_{17}$H$_{15}$Br$_2$NO$_2$ requires 423.95)

Step 2: P7C3-S211:
2-(3,6-dibromo-9H-carbazol-9-yl)propanoic acid

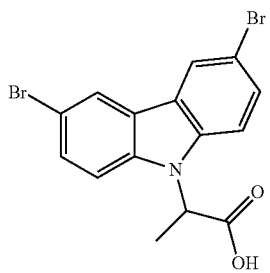 [SMILES: CC(C(=O)O)n1c2ccc(Br)cc2c2cc(Br)ccc21]

Synthesized analogously to P7C3-S165.

$^1$H NMR (400 MHz, CDCL$_3$) δ 8.16 (d, J=1.8 Hz, 2H), 7.55 (dd, J=8.7, 1.8 Hz, 2H), 7.27 (s, 2H), 5.39 (dd, J=14.7, 7.3 Hz, 1H), 1.85 (d, J=7.3 Hz, 3H). ESI m/z: 395.7 ([M+H]$^+$, C$_{15}$H$_{21}$Br$_2$NO$_2$ requires 395.92)

P7C3-S212: iminodibenzyl

This compound was purchased from SigmaAldrich.

P7C3-S216: 6-bromo-9H-carbazole-3-carbonitrile

Step 1: 9-H-carbazole-3-carbonitrile

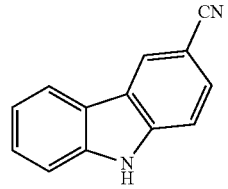 [SMILES: N#Cc1ccc2[nH]c3ccccc3c2c1]

3-bromo-9H-carbazole (150 mg, 0.61 mmol) and CuCN (60 mg, 0.67 mmol) were dissolved in 3 ml of NMP and heated to 200° C. overnight. Upon completion the reaction was warmed to room temperature, diluted with 3 ml of H$_2$O and filtered to remove CuBr salts. The filtrate was extracted 3× with EtOAc, washed with H$_2$O, brine, and dried over MgSO$_4$. The crude mixture was purified on SiO$_2$ (0 to 50% EtOAc/hexanes to afford 9-H-carbazole-3-carbonitrile.

$^1$H NMR (500 MHz, DMSO-d$_6$) δ 11.87 (s, 1H), 8.71 (s, 1H), 8.24 (d, J=7.8 Hz, 1H), 7.75 (d, J=8.4 Hz, 1H), 7.63 (d, J=8.4 Hz, 1H), 7.57 (d, J=7.9 Hz, 1H), 7.49 (t, J=7.6 Hz, 1H), 7.26 (t, J=7.5 Hz, 1H). ESI m/z: 193.0 ([M+H]$^+$, C$_{13}$H$_8$N$_2$ requires 193.07)

Step 2: 6-bromo-9H-carbazole-3-carbonitrile (P7C3-S216)

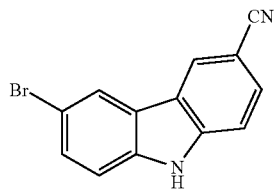 [SMILES: N#Cc1ccc2[nH]c3ccc(Br)cc3c2c1]

9-H-carbazole-3-carbonitrile (185 mg, 0.962 mmol) and N-bromosuccinimide (171 mg, 0.92 mmol) were added to 5 ml of EtOAc and 13 ml of toluene. This mixture was stirred for 3 days at room temperature. Upon completion of the reaction, the reaction was concentrated, diluted in EtOAc, washed with NaHCO₃, H₂O, brine, and dried over Na₂SO₄. The crude mixture was purified on SiO₂ (0 to 50% EtOAc/hexanes to afford the desired product in 90% yield.

$^1$H NMR (400 MHz, CDCl₃) δ 8.38 (s, 1H), 8.35 (s, 1H), 8.22 (s, 1H), 7.69 (dd, J=8.5, 1.4 Hz, 1H), 7.60 (dd, J=8.6, 1.8 Hz, 1H), 7.50 (d, J=8.5 Hz, 1H), 7.38 (d, J=8.6 Hz, 1H). ESI m/z: 270.9 ([M+H]⁺, C₁₃H₇BrN₂ requires 270.98)

P7C3-S222:
3-amino-5-bromo-1H-indole-2-carbonitrile

Step 1. Synthesis of
5-bromo-2-((cyanomethyl)amino)benzonitrile

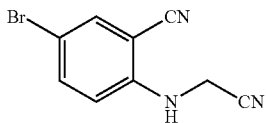 [SMILES: N#CCNc1ccc(Br)cc1C#N]

Following Representative Procedure 1,2-((cyanomethyl)amino)benzonitrile (Michaelidou, S. S.; Koutentis, P. A. *Tetrahedron* 2010, 66, 685-688) (0.020 g, 0.127 mmol) was treated with NBS (0.034 g, 0.191 mmol) in CH₂Cl₂:MeOH (1:1) (25 mL) to afford the title product (0.017 g, 58%). $^1$H NMR (CDCl₃-MeOD [4:2], 500 MHz) δ 7.59-7.54 (m, 2H), 6.67 (d, 1H, J=8.8 Hz). 4.16 (s, 2H). MS (ESI) m/z 235.8 [M−H]⁻ ([M−H]⁻, C₉H₅BrN₃ requires 235.0).

Step 2. Synthesis of
3-amino-5-bromo-1H-indole-2-carbonitrile
(P7C3-S222)

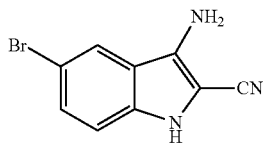 [SMILES: N#Cc1[nH]c2ccc(Br)cc2c1N]

Following a literature procedure (Michaelidou, S. S.; Koutentis, P. A. *Tetrahedron* 2010, 66, 685-688), 5-bromo-2-((cyanomethyl)amino)benzonitrile (0.290 g, 1.234 mmol) and K₂CO₃ (0.085 g, 0.617 mmol) were dissolved in EtOH (3.9 mL) and heated to 120° C. in a microwave reactor for 10 min. The reaction mixture was then cooled to room temperature, diluted with water and extracted with CH₂Cl₂. The organic layers were dried over Na₂SO₄, filtered and condensed. The crude mixture was purified by chromatography (SiO₂, 0-50% EtOAc/Hexanes) to afford the title compound (0.254 g, 88%).

$^1$H NMR (CDCl₃-MeOD [4:2], 500 MHz) δ 7.46 (d, 1H, J=1.7 Hz), 7.04 (dd, 1H, J=1.7, 8.8 Hz), 6.83 (d, 1H, J=8.8 Hz). MS (ESI) m/z 236.8 [M+H]⁺ ([M+H]⁺, C₉H₇BrN₃ requires 237.0).

P7C3-S224: 2-(3-bromo-6-cyano-9H-carbazol-9-yl)acetic acid

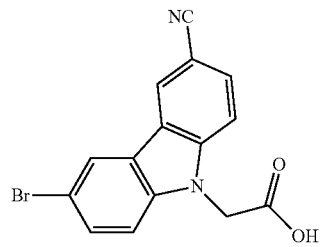 [SMILES: N#Cc1ccc2c(c1)c1cc(Br)ccc1n2CC(=O)O]

The title compound was prepared analogously to P7C3-S165.

$^1$H NMR (CDCl₃₊ (CD₃)₂CO, 400 MHz) δ 8.18 (d, J=1.6 Hz, 1H), 8.04 (d, J=1.9 Hz, 1H), 7.51 (dd, J=8.5, 1.6 Hz, 1H), 7.40 (dd, J=8.6, 1.9 Hz, 1H), 7.31 (d, J=8.6 Hz, 1H), 7.17 (d, J=8.7 Hz, 1H), 4.91 (s, 2H). MS (ESI), m/z: calculated 327.98. Found 328.8 (M+1).

P7C3-S225: 6-bromo-9H-carbazole-3-carboxylic acid

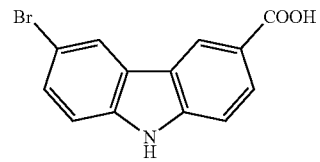 [SMILES: O=C(O)c1ccc2[nH]c3ccc(Br)cc3c2c1]

P7C3-S216 (299.6 mg, 1.1 mmol) was treated with HCl in dioxane (4.0 M, 3 ml) and concentrated HCl at 100° C. for 60 hours. The crude mixture was taken up in EtOAc, neutralized with 1N NaOH and washed with brine. The organic layer was dried over Na₂SO₄, filtered and condensed. Column chromatography in 5% MeOH/DCM (+0.1% formic acid) gave desired in 90% yield.

$^1$H NMR (DMSO, 400 MHz) δ δ 11.69 (s, 1H), 8.75 (d, J=1.6 Hz, 1H), 8.33 (d, J=1.9 Hz, 1H), 7.98 (dd, J=8.5, 1.7 Hz, 1H), 7.89 (bs, 1H), 7.62-7.42 (m, 2H), 7.24 (bs, 1H). MS (ESI), m/z: calculated 288.97. Found 289.8 (M+1).

P7C3-S227: 6-bromo-9-(carboxymethyl)-9H-pyrido[3,4-b]indole-3-carboxylic acid

Step 1: ethyl 6-bromo-9-(2-ethoxy-2-oxoethyl)-9H-pyrido[3,4-b]indole-3-carboxylate

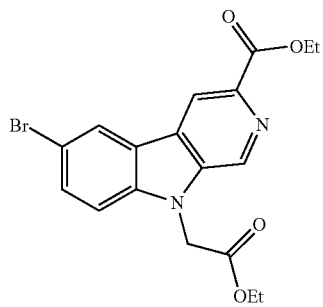 [SMILES: CCOC(=O)Cn1c2ccc(Br)cc2c2cc(C(=O)OCC)ncc21]

Ethyl 6-bromo-9-(2-ethoxy-2-oxoethyl)-9H-pyrido[3,4-b]indole-3-carboxylate was synthesized analogously to P7C3-S164. The crude material was purified on SiO$_2$ (0-60% EtOAc/hexanes) to give the desired compound in 92% yield.

$^1$H NMR (500 MHz, DMSO-d$_6$) δ 9.13 (s, 1H), 9.03 (s, 1H), 8.78 (s, 1H), 7.80 (dd, J=8.8, 1.5 Hz, 1H), 7.74 (d, J=8.9 Hz, 1H), 5.59 (s, 2H), 4.39 (q, J=7.1 Hz, 2H), 4.21-4.12 (m, 2H), 1.38 (t, J=7.1 Hz, 3H), 1.21 (t, J=7.1 Hz, 3H). ESI m/z: 404.8 ([M+H]$^+$, C$_{12}$H$_{17}$BrN$_2$O$_4$ requires 405.04)

Step 2:—6-bromo-9-(carboxymethyl)-9H-pyrido[3,4-b]indole-3-carboxylic acid

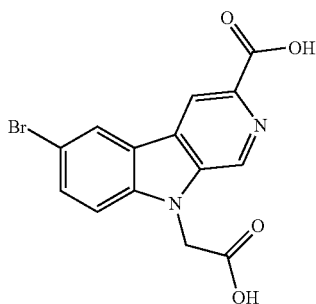

6-bromo-9-(carboxymethyl)-9H-pyrido[3,4-b]indole-3-carboxylic acid (P7C3-S227) was synthesized analogously to P7C3-S165.

$^1$H NMR (500 MHz, DMSO-d$_6$) δ 9.13 (s, 1H), 9.02 (s, 1H), 8.75 (s, 1H), 7.80 (d, J=9.2 Hz, 1H), 7.75 (d, J=8.8 Hz, 1H), 5.49 (s, 2H). ESI m/z: 348.7 ([M+H]$^+$, C$_{14}$H$_9$BrN$_2$O$_4$ requires 348.97)

P7C3-S228: 3-bromo-6-methyl-9H-carbazole

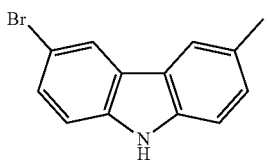

This compound was prepared according to U.S. Pat. No. 6,018,046 A1, incorporated herein by reference in its entirety.

P7C3-S229: 1-(9H-carbazol-9-yl)-3-(phenylamino)propan-2-ol

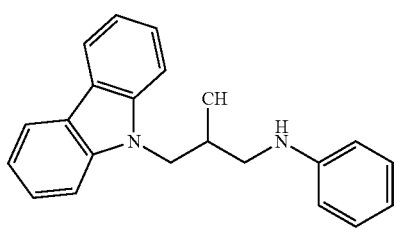 [SMILES: CC(CNc1ccccc1)Cn1c2ccccc2c2ccccc21]

The title compound was prepared according to the procedure of Asso et al, Chem Med Chem, 2008 (3) 1530.

MS (ESI): 317.1 [M+H]$^+$, C$_{21}$H$_{20}$N$_2$O requires 316.2.

P7C3-S230—2-(3,6-dibromo-9H-carbazol-9-yl)-N-(phenylsulfonyl)acetamide

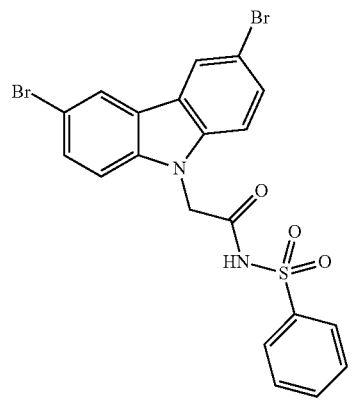 [SMILES: O=C(Cn1c2ccc(Br)cc2c2cc(Br)ccc21)NS(=O)(=O)c1ccccc1]

2-(3,6-dibromo-9H-carbazol-9-yl)-N-(phenylsulfonyl)acetamide was synthesized analogously to P7C3-S232 except benzensulfonamide was used.

$^1$H NMR (400 MHz, Acetone-d$_6$) δ 8.37 (d, J=1.8 Hz, 2H), 8.00 (dd, J=8.4, 1.2 Hz, 2H), 7.75-7.69 (m, 1H), 7.63-7.57 (m, 2H), 7.53 (dd, J=8.7, 2.0 Hz, 2H), 7.38 (d, J=8.7 Hz, 2H), 5.33 (s, 2H). ESI m/z: 518.5 ([M−H]$^+$, C$_{20}$H$_{14}$Br$_2$N$_2$O$_3$S requires 518.91)

P7C3-S231—2-(3,6-dibromo-9H-carbazol-9-yl)-N-hydroxyacetamide

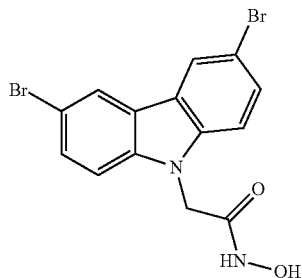 [SMILES: O=C(Cn1c2ccc(Br)cc2c2cc(Br)ccc21)NO]

Following a published procedure (J. Med. Chem., 2011, 54, 5576-5582), ethyl 2-(3,6-dibromo-9H-carbazol-9-yl)acetate (P7C3-S164) (50 mg, 0.12 mmol) was suspended in a 1:1 (v/v) mixture of methanol (500 ul) and 50% hydroxylamine (aq.). To this suspension was added 1 N NaOH$_{(aq)}$ (250 ul). Upon completion 1N HCl was added, upon which the product precipitated from solution. The precipitate was further purified on SiO$_2$ (0-60% EtOAc/hexanes.)

$^1$H NMR (500 MHz, Acetone-d$_6$) δ 8.39 (s, 2H), 7.59 (dd, J=25.4, 8.4 Hz, 4H), 5.08 (s, 2H). ESI m/z: 394.5 ([M−H]$^+$, C$_{14}$H$_{10}$Br$_2$N$_2$O$_2$ requires 394.91)

P7C3-S232: 2-(3,6-dibromo-9H-carbazol-9-yl)-N-(methylsulfonyl)acetamide

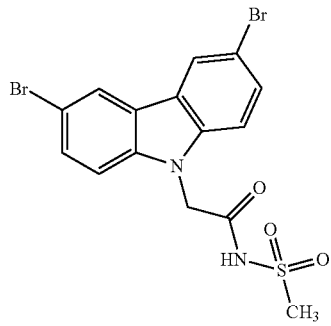 [SMILES: CS(=O)(=O)NC(=O)Cn1c2ccc(Br)cc2c2cc(Br)ccc21]

Following a published procedure (*Bioorg. Med. Chem.*, 2006, 1331-1338) a solution of 2-(3,6-dibromo-9H-carbazol-9-yl)acetic acid (P7C3-S165) (100 mg, 0.26 mmol) in dry THF was added to a stirred solution of carbonyldiimidazole (42.3 mg, 0.261 mmol) in THF. The mixture was stirred 30 min at room temperature and 30 min at reflux. The mixture was cooled to room temperature and methanesulfonamide (25 mg, 0.261 mmol) was added in one portion and stirred for 10 minutes. A solution of 1,8-Diazabicyclo[5.4.0]undec-7-ene (40 mg, 0.261 mmol) in THF was added dropwise. The solution was stirred overnight at room temperature. The solution was poured into ice cold 1 N HCl and extracted with EtOAc. The organic layer was washed with water, brine, dried over $MgSO_4$ and concentrated. The crude material was purified on $SiO_2$ (0-50% EtOAc/hexanes.)

$^1$H NMR (500 MHz, Acetone-$d_6$) δ 8.39 (s, 2H), 7.57 (dd, J=22.2, 8.7 Hz, 4H), 5.22 (s, 2H), 3.11 (s, 3H) ESI m/z: 458.5 ([M–H]$^+$, $C_{15}H_{12}Br_2N_2O_3S$ requires 456.89)

P7C3-S235: 2-(3,6-dibromo-9H-carbazol-9-yl)acetonitrile

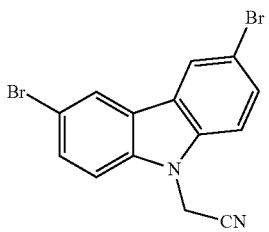 [SMILES: N#CCn1c2ccc(Br)cc2c2cc(Br)ccc21]

3,6-dibromocarbazole (500 mg, 1.54 mmol) was dissolved in DMF (7.5 ml) and treated with KOH (86 mg, 1.54 mmol) for 30 minutes. $K_2CO_3$ (319 mg, 2.3 mmol) and bromoacetonitrile (332 mg, 2.77 mmol) were added. The reaction was stirred overnight at room temperature. Upon addition of $H_2O$ a precipitate formed which was filtered and purified on $SiO_2$ (0-25% EtOAc/hexanes.)

$^1$H NMR (500 MHz, Acetone-$d_6$) δ 8.47 (s, 2H), 7.74 (dd, J=20.1, 8.7 Hz, 4H), 5.73 (s, 2H). ESI m/z: 360.6 ([M–H]$^+$, $C_{14}H_8Br_2N_2$ requires 360.91)

P7C3-S236: 3-bromo-9H-carbazole

This compound was purchased from SigmaAldrich.

P7C3-S237: 3,6-dimethyl-9H-carbazole

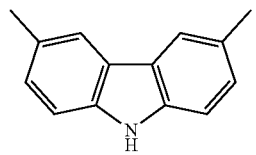

This compound was prepared as reported in Beyer, M. et al. J. Org. Chem. 2003 (68) 2209.

P7C3-S238: 2-(3-bromo-6-carbamoyl-9H-carbazol-9-yl)acetic acid

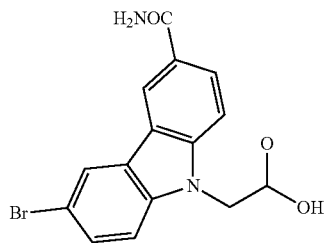 [SMILES: NC(=O)c1ccc2c(c1)c1cc(Br)ccc1n2CC(O)O]

The title compound was prepared analogously to P7C3-S165.

MS (ESI) m/z: 346.9 [M+H]$^+$, C15H11BrN2O3 requires 346.0

P7C3-S239: 6-bromo-9-(carboxymethyl)-9H-carbazole-3-carboxylic acid

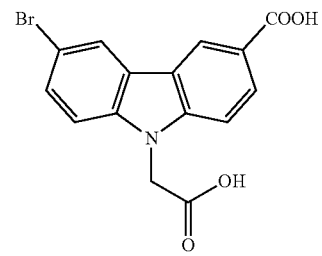 [SMILES: O=C(O)Cn1c2ccc(Br)cc2c2cc(C(=O)O)ccc21]

The title compound was prepared analogously to P7C3-165

$^1$H NMR (DMSO, 500 MHz) δ 13.16 (s, 1H), 8.78 (s, 1H), 8.38 (s, 1H), 8.02 (d, J=8.6 Hz, 1H), 7.93 (s, 1H), 7.62 (d, J=15.0 Hz, 2H), 7.29 (s, 1H), 5.29 (s, 2H). MS (ESI), m/z: calculated 346.98. Found 347.9 (M+1).

P7C3-S240: 2-(3-bromo-6-methyl-9H-carbazol-9-yl) acetic acid

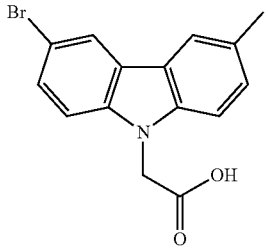 [SMILES: Cc1ccc2c(c1)c1cc(Br)ccc1n2CC(=O)O]

The title compound was prepared analogously to P7C3-165.

$^1$H NMR (CDCl$_3$+(CD$_3$)$_2$CO, 400) δ 8.09 (d, J=2.0 Hz, 1H), 7.79 (s, 1H), 7.54 (d, J=8.6 Hz, 2H), 7.43 (dd, J=8.7, 2.0 Hz, 1H), 7.26 (m, 1H), 4.99 (s, 2H), 2.44 (s, 3H). MS (ESI), m/z: calculated 317.01. Found 318.0 (M+1).

P7C3-S241: N-(3-(3,6-dibromo-9H-carbazol-9-yl)-2-fluoropropyl)-1,1,1-trifluoro-N-(3-methoxyphenyl)methanesulfonamide

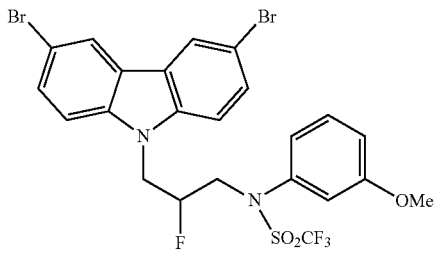

Following Representative Procedure 4, P7C3-S244 was fluorinated to give the title compound. $^1$H NMR (400 MHz, CDCl$_3$) δ 8.15 (d, J=1.9 Hz, 2H), 7.56 (dd, J=8.7, 1.9 Hz, 2H), 7.32 (t, J=8.2 Hz, 1H), 7.21 (d, J=8.6 Hz, 2H), 6.99-6.90 (m, 2H), 6.86 (m, 1H), 5.08-4.86 (dm, 1H), 4.57-4.44 (m, 2H), 4.09 (m, 2H), 3.79 (s, 3H). MS (ESI), m/z: calculated 635.93. Found 680.6 (M+HCOO$^-$)$^-$.

P7C3-S242: 3-indolepropionic acid

This compound was purchased from SigmaAldrich.

P7C3-S244: N-(3-(3,6-dibromo-9H-carbazol-9-yl)-2-hydroxypropyl)-1,1,1-trifluoro-N-(3-methoxyphenyl)methanesulfonamide Step 1: 1,1,1-trifluoro-N-(3-methoxyphenyl)methanesulfonamide

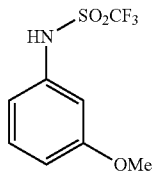

A solution of trifluoromethanesulfonic anhydride (45 ml, 26.7 mmol) in methylene chloride (250 ml) was added dropwise to an ice chilled solution of m-anisidine (25 ml, 22.3 mmol) and triethylamine (39 ml, 28.0 mmol) in methylene chloride (1.25 L). The reaction was stirred overnight at ambient temperature. Workup was performed portionwise. Each of the two portions was basified by addition of 250 ml of 2.5 N NaOH solution and 625 ml MeOH. The aqueous was extracted thrice (100 ml each) with methylene chloride. The combined aqueous phases was acidified to pH 2 with 18% HCl and again extracted with methylene chloride three times. The organic layer is dried over MgSO$_4$, filtered and condensed to give 17.69 g of brown solid in 77% yield.

$^1$H NMR (CDCl$_3$, 400 MHz) δ7.48-7.13 (m, 1H), 6.97-6.61 (m, 3H), 3.82 (s, 3H). MS (ESI), m/z: calculated 255.21. Found 255.9 (M+1)$^+$.

Step 2: N-(3-(3,6-dibromo-9H-carbazol-9-yl)-2-hydroxypropyl)-1,1,1-trifluoro-N-(3-methoxyphenyl)methanesulfonamide (P7C3-S244)

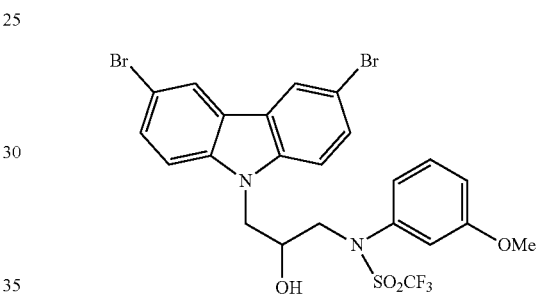

N-butyllithium (2.5 M in hexanes, 48 ml) was added dropwise to an ice-cooled solution of 1,1,1-trifluoro-N-(3-methoxyphenyl)methanesulfonamide (22.07 g, 86.5 mmol) in dry dioxane (145 ml) over a 40 minute period. The solution was then stirred at ambient temperature for 15 minutes before addition of 3,6-dibromo-9-(oxiran-2-ylmethyl)-9H-carbazole (25.05 g, 65.7 mmol) followed by heating at 90° C. for an hour. The reaction was cooled then diluted with 1.2 L ethyl acetate and washed several times with water and finally brine. The organic layer was dried over MgSO$_4$, filtered and condensed to give an orange viscous mixture. The residue was dissolved in 150 ml of 60% methylene chloride/hexanes, then concentrated to yellow foam to which a further 150 ml of 60% methylene chloride/hexanes was added and stirred overnight. The mixture was filtered and washed several times with 60% methylene chloride/hexanes until the solid was white giving 20.1 g of 99%

$^1$H NMR (CDCl$_3$, 400 MHz) δ 8.13 (d, J=1.9 Hz, 2H), 7.54 (dd, J=8.7, 1.9 Hz, 2H), 7.33 (t, J=8.1 Hz, 1H), 7.22 (d, J=8.7 Hz, 2H), 6.95 (dd, J=8.4, 2.3 Hz, 2H), 6.88 (s, 1H), 4.56-4.10 (m, 4H), 3.99 (m, 1H), 3.81 (s, 3H), 1.98 (d, J=4.2 Hz, 1H). MS (ESI), m/z: calculated 633.94. Found 678.6 (M+HCOO)$^-$.

P7C3-S246: ethyl 5-tosyl-5H-pyrimido[5,4-b]indole-2-carboxylate

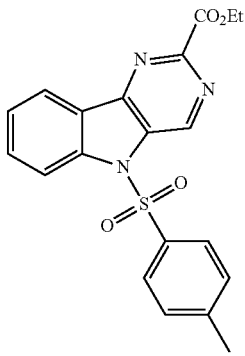 [SMILES: CCOC(=O)c1ncc2c(n1)c1ccccc1n2S(=O)(=O)c1ccc(C)cc1]

The title compound was synthesized following a reported procedure (Rahtz et al. U.S. Pat. No. 4,564,610 A1).

$^1$H NMR (CDCl$_3$, 500 MHz) δ 9.76 (s, 1H), 8.44 (d, 1H, J=7.7 Hz), 8.37 (d, 1H, J=8.5 Hz), 7.80 (t, 1H, J=7.9 Hz), 7.75 (d, 2H, J=8.4 Hz), 7.54 (t, 1H, J=7.5 Hz), 7.18 (d, 2H, J=8.1 Hz), 4.60 (q, 2H, J=7.1 Hz), 2.31 (s, 3H), 1.52 (t, 3H, J=7.1 Hz).

P7C3-S245: 2-(dimethylamino)-5H-pyrimido[5,4-b]indol-4-ol

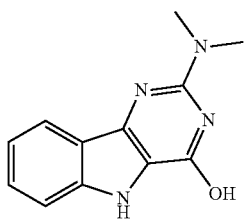 [SMILES: CN(C)c1nc(O)c2[nH]c3ccccc3c2n1]

To a suspension of 3-amino-1H-indole-2-carbonitrile (Michaelidou, S. S.; Koutentis, P. A. *Tetrahedron* 2010, 66, 685-688) (0.032 g, 0.200 mmol) in DCE (1.5 mL) was added Cl$_2$CN$^+$Me$_2$Cl$^-$ (0.046 g, 0.28 mmol) and the mixture was stirred under reflux overnight. Upon completion, the cooled reaction was concentrated and dissolved in AcOH (0.6 mL). Then, NH$_4$OAc (0.040 g, 0.52 mmol) was added and the mixture was stirred under reflux for 20 h. The cooled reaction was neutralized with saturated NaHCO$_3$ and the mixture extracted with EtOAc. The organic layers were washed with brine, dried over Na$_2$SO$_4$, filtered and condensed. The crude mixture was purified by chromatography (SiO$_2$, 0-10% MeOH/CH$_2$Cl$_2$) to afford the title compound (0.015 g, 33%).

$^1$H NMR (CDCl$_3$-MeOD [4:2], 500 MHz) δ 7.94 (d, 1H, J=8.0 Hz), 7.33-7.28 (m, 2H), 7.03 (t, 1H, J=7.1 Hz), 3.08 (s, 6H). MS (ESI) m/z 229.0 [M+H]$^+$ ([M+H]$^+$, C$_{12}$H$_{13}$N$_4$O requires 229.2).

P7C3-S247: ethyl 5-tosyl-4,5-dihydro-1H-pyrimido[5,4-b]indole-2-carboxylate

The title compound was synthesized following a reported procedure (Rahtz et al. U.S. Pat. No. 4,564,610 A1).

$^1$H NMR (CDCl$_3$, 500 MHz) δ 8.02 (d, 1H, J=8.1 Hz), 7.75 (d, 1H, J=7.4 Hz), 7.60 (d, 2H, J=8.4 Hz), 7.34-7.21 (m, 2H), 7.18 (d, 2H, J=8.1 Hz), 5.30 (s, 2H), 4.39 (q, 2H, J=7.1 Hz), 2.31 (s, 3H), 1.40 (t, 3H, J=7.1 Hz).

P7C3-S248: L-tryptophan

This compound was purchased from SigmaAldrich.

P7C3-S249: L-5-hydroxy-tryptophan

This compound was purchased from SigmaAldrich

P7C3-S248: L-tryptophan methyl ester hydrochloride

This compound was purchased from SigmaAldrich

P7C3-S251: N-(3-(3,6-dibromo-9H-carbazol-9-yl)-2-hydroxypropyl)-N-(3-methoxyphenyl)methanesulfonamide

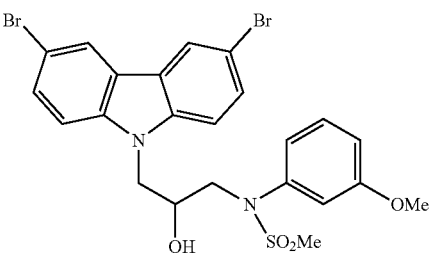 [SMILES: COc1cccc(N(CC(O)Cn2c3ccc(Br)cc3c3cc(Br)ccc32)S(C)(=O)=O)c1]

P7C3-S251 was synthesized analogously to P7C3-S244 in quantitative yield.

$^1$H NMR (CDCl$_3$, 400 MHz) δ 8.13 (d, J=1.6 Hz, 2H), 7.53 (dd, J=8.8, 1.8 Hz, 2H), 7.37-7.30 (m, 1H), 7.26 (d, J=7.7 Hz, 2H), 6.98-6.83 (m, 3H), 4.52-4.37 (m, 3H), 4.36-4.17 (m, 2H), 3.82-3.91 (m, 1H), 3.76 (s, 3H), 3.71 (s, 1H), 2.93 (s, 3H), 2.28 (d, J=3.7 Hz, 1H). MS (ESI), m/z: calculated 579.97. Found 624.6 (M+HCOO)$^-$.

P7C3-S252: N-(3-(3,6-dibromo-9H-carbazol-9-yl)-2-hydroxypropyl)-N-(3-methoxyphenyl)benzenesulfonamide

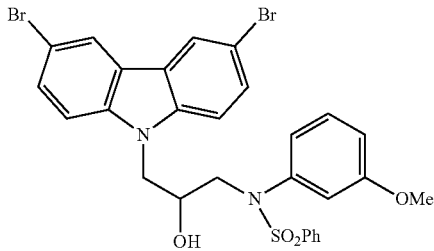

P7C3-S252 was synthesized analogously to P7C3-S244 using representative procedure 3 and N-(3-methoxyphenyl)benzenesulfonamide and in quantitative yield.

$^1$H NMR (CDCl$_3$, 400 MHz) δ 8.13 (d, J=1.9 Hz, 2H), 7.67-7.38 (m, 8H), 7.26 (d, J=8.7 Hz, 2H), 6.90 (dd, J=8.4, 2.5 Hz, 1H), 6.73-6.55 (m, 3H), 4.50 (dd, J=15.1, 3.4 Hz, 1H), 4.32 (dd, J=15.1, 8.3 Hz, 1H), 4.22 (bs, 1H), 3.80-3.65 (m, 5H), 2.32 (d, J=3.9 Hz, 1H). MS (ESI), m/z: calculated 641.98. Found 686.6 (M+HCOO)$^-$.

P7C3-S253: N-(3-(3,6-dibromo-9H-carbazol-9-yl)-2-hydroxypropyl)-N-(3-methoxyphenyl)-2-(trifluoromethyl)benzenesulfonamide

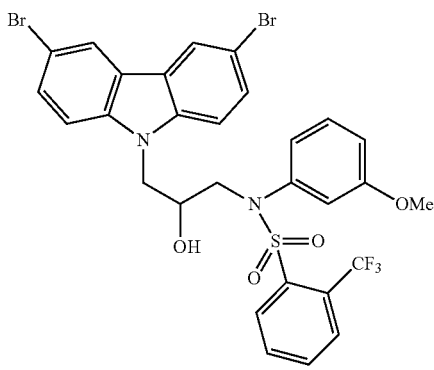 [SMILES: COc1cccc(N(CC(O)Cn2c3ccc(Br)cc3c3cc(Br)ccc32)S(=O)(=O)c2ccccc2C(F)(F)F)c1]

P7C3-S253 was synthesized analogously to P7C3-S244 using representative procedure 3 and N-(3-methoxyphenyl)-2-(trifluoromethyl)benzenesulfonamide and in quantitative yield.

$^1$H NMR (CDCl$_3$, 400 MHz) δ) 8.11 (d, J=1.9 Hz, 2H), 7.88 (d, J=7.9 Hz, 1H), 7.72 (d, J=8.2 Hz, 1H), 7.65 (t, J=7.7 Hz, 1H), 7.59-7.42 (m, 3H), 7.36-7.17 (m, 2H), 7.17 (t, J=8.1 Hz, 1H), 6.85-6.62 (m, 3H), 4.46 (dd, J=15.1, 3.6 Hz, 1H), 4.32 (dd, J=15.0, 8.4 Hz, 1H), 4.20 (bs, 1H), 3.93 (d, J=6.1 Hz, 1H), 3.75-3.66 (m, 4H), 2.14 (d, J=4.0 Hz, 1H). MS (ESI), m/z: calculated 709.97. Found 754.5 (M+HCOO)$^-$.

P7C3-S254: N-(3-(3,6-dibromo-9H-carbazol-9-yl)-2-hydroxypropyl)-4-methoxy-N-(3-methoxyphenyl)benzenesulfonamide

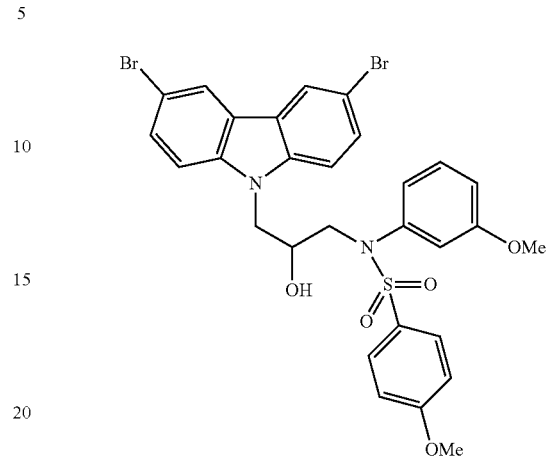

P7C3-S254 was synthesized analogously to P7C3-S244 using representative procedure 3 and 4-methoxy-N-(3-methoxyphenyl)benzenesulfonamide and in quantitative yield.

$^1$H NMR (CDCl$_3$, 400 MHz) δ 8.20-8.01 (m, 2H), 7.52 (dd, J=8.6, 1.8 Hz, 2H), 7.48 (d, J=8.8 Hz, 2H), 7.23 (m, 3H), 6.91 (d, J=8.9 Hz, 2H), 6.89-6.83 (m, 1H), 6.67 (t, J=2.3 Hz, 1H), 6.63-6.57 (m, 1H), 4.53-4.39 (m, 1H), 4.37-4.25 (m, 1H), 4.20 (bs, 1H), 3.89 (s, 3H), 3.75 (s, 3H), 3.68-3.58 (m, 2H), 2.29 (d, J=4.1 Hz, 1H). MS (ESI), m/z: calculated 671.99. Found 716.5 (M+HCOO)$^-$.

P7C3-S256: N-(3-(3,6-dibromo-9H-carbazol-9-yl)-2-fluoropropyl)-N-(3-methoxyphenyl)methanesulfonamide

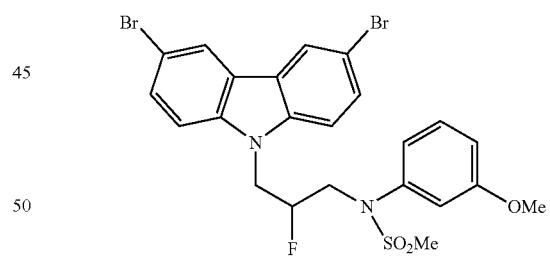

P7C3-S256 was synthesized analogously to P7C3-S241 using representative procedure 4 with morpho-DAST and N-(3-(3,6-dibromo-9H-carbazol-9-yl)-2-hydroxypropyl)-N-(3-methoxyphenyl)methanesulfonamide and in quantitative yield.

$^1$H NMR (CDCl$_3$, 400 MHz) δ 8.14 (d, J=2.1 Hz, 2H), 7.55 (dd, J=8.6, 1.9 Hz, 2H), 7.33 (t, J=8.0 Hz, 1H), 7.25 (d, J=9.6 Hz, 2H), 7.01-6.82 (m, 3H), 4.97 (dm, J$_{H-F}$=49.2 Hz, 1H), 4.73-4.35 (m, 2H), 4.14-3.98 (m, 2H), 3.81 (s, 3H), 2.96 (s, 3H). MS (ESI), m/z: calculated 581.96. Found 626.5 (M+HCOO)$^-$.

P7C3-S257: N-(3-(3,6-dibromo-9H-carbazol-9-yl)-2-fluoropropyl)-N-(3-methoxyphenyl)-2-(trifluoromethyl)benzenesulfonamide

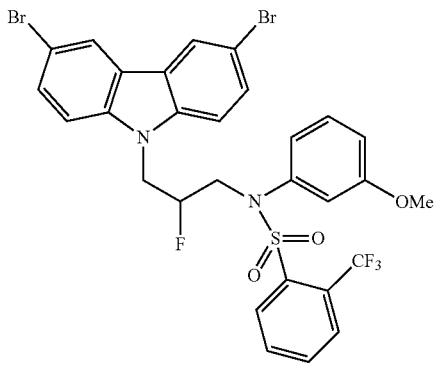 [SMILES: COc1cccc(N(CC(F)Cn2c3ccc(Br)cc3c3cc(Br)ccc32)S(=O)(=O)c2ccccc2C(F)(F)F)c1]

P7C3-S257 was synthesized analogously to P7C3-S241 using representative procedure 4 with morpho-DAST and N-(3-(3,6-dibromo-9H-carbazol-9-yl)-2-hydroxypropyl)-N-(3-methoxyphenyl)-2-(trifluoromethyl)benzenesulfonamide and in 95% yield.

$^1$H NMR (CDCl$_3$, 400 MHz) δ 8.13 (d, J=1.8 Hz, 2H), 7.90 (d, J=7.9 Hz, 1H), 7.72 (d, J=8.0 Hz, 1H), 7.65 (t, J=7.8 Hz, 1H), 7.56 (dd, J=8.7, 1.9 Hz, 2H), 7.49 (t, J=7.8 Hz, 1H), 7.29 (d, J=8.8 Hz, 2H), 7.16 (t, J=8.1 Hz, 1H), 6.81 (dd, J=8.4, 2.5 Hz, 1H), 6.78-6.64 (m, 2H), 4.93 (dm, J$_{H-F}$=48.1 Hz, 1H), 4.76-4.44 (m, 2H), 4.23 (t, J=14.3 Hz, 1H), 4.06 (dd, J=15.2, 6.1 Hz, 1H), 3.71 (s, 3H).

MS (ESI), m/z: calculated 711.97. Found 756.5 (M+HCOO)$^-$.

P7C3-S258: N-(3-(3,6-dibromo-9H-carbazol-9-yl)-2-fluoropropyl)-4-methoxy-N-(3-methoxyphenyl)benzenesulfonamide

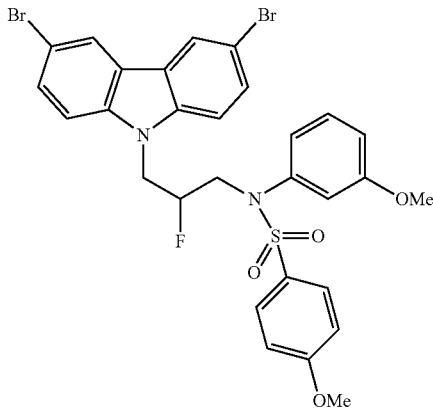 [SMILES: COc1ccc(S(=O)(=O)N(CC(F)Cn2c3ccc(Br)cc3c3cc(Br)ccc32)c2cccc(OC)c2)cc1]

P7C3-S258 was synthesized analogously to P7C3-S241 using representative procedure 4 with morpho-DAST and N-(3-(3,6-dibromo-9H-carbazol-9-yl)-2-hydroxypropyl)-4-methoxy-N-(3-methoxyphenyl)benzenesulfonamide and in quantitative yield.

$^1$H NMR (CDCl$_3$, 400 MHz) δ 8.14 (d, J=1.9 Hz, 2H), 7.55 (dd, J=8.8, 1.9 Hz, 2H), 7.51 (d, J=8.9 Hz, 2H), 7.26-7.20 (m, 3H), 6.93 (d, J=8.9 Hz, 2H), 6.88 (dd, J=8.2, 2.5 Hz, 1H), 6.70 (t, J=2.2 Hz, 1H), 6.64 (dt, J=7.9, 1.4 Hz, 1H), 4.93 (dm, J$_{H-F}$=48.1, 6.6 Hz, 1H), 4.72 (ddd, J=31.8, 16.0, 2.4 Hz, 1H), 4.52 (td, J=16.9, 16.2, 8.2 Hz, 1H), 4.03-3.91 (m, 1H), 3.89 (s, 3H), 3.86-3.76 (m, 1H), 3.75 (s, 3H). MS (ESI), m/z: calculated 673.99. Found 718.6 (M+HCOO)$^-$.

P7C3-S262: ethyl 5H-pyrimido[5,4-b]indole-2-carboxylate

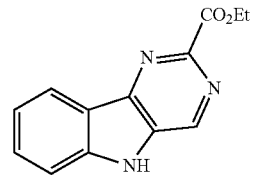 [SMILES: CCOC(=O)c1ncc2[nH]c3ccccc3c2n1]

The title compound was synthesized following a reported procedure (Rahtz et al. U.S. Pat. No. 4,564,610 A1, incorporated herein by reference).

$^1$H NMR (CDCl$_3$, 400 MHz) δ 9.06 (s, 1H), 8.50 (d, 1H, J=8.0 Hz), 7.64 (ddd, 1H, J=1.2, 7.1, 8.2 Hz), 7.56 (d, 1H, J=8.3 Hz), 7.36 (ddd, 1H, J=0.9, 7.1, 8.0 Hz), 4.58 (q, 2H, J=7.1 Hz), 1.50 (t, 3H, J=7.1 Hz).

P7C3-S264: N-(3-(3,6-dibromo-9H-carbazol-9-yl)-2-hydroxypropyl)-1,1,1-trifluoromethanesulfonamide

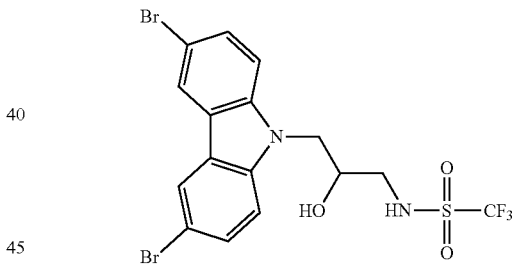

1-amino-3-(3,6-dibromo-9H-carbazol-9-yl)propan-2-ol (100 mg, 0.2518 mmol) and triethylamine (42 µL, 0.3022 mmol) were dissolved in 1.7 mL DCM. The vial was cooled to 0° C. Triflic anhydride (51 µL, 0.3022 mmol) was then added and the solution was left to react overnight. The reaction mixture was basified with 1M NaOH, and the layers were separated. The aqueous layer was washed 3× with DCM and the combined organic layers were then acidified using 18% HCl. The mixture was separated and the aqueous layer washed 3× with DCM. The combined organic layers were dried and concentrated to afford crude material as a yellow residue. This was purified by column chromatography using a gradient 60% DCM/Hex to 90% DCM/MeOH eluent and afforded 8.8 mg (6.6% yield) of product as a white solid. $^1$H NMR (500 MHz, CD$_3$OD) δ 8.23 (d, J=2.1 Hz, 1H), 8.21 (d, J=2.3 Hz, 1H), 7.56 (dq, J=8.7, 1.9 Hz, 2H), 7.49 (dd, J=8.7, 5.1 Hz, 2H), 4.40 (ddd, J=15.3, 6.6, 3.6 Hz, 1H), 4.36-4.26 (m, 1H), 4.13 (s, 1H), 3.42 (dd, J=13.7, 4.7 Hz, 1H), 3.39-3.32 (m, 1H). MS (ESI) m/z=526.6 ([M−H]$^-$, C16H13Br2F3N2O3S requires 527.90.

P7C3-S265: alpidem, also known as 6-Chloro-2-(4-chlorophenyl)-N,N-dipropyl-imidazo[1,2-a]pyridine-3-acetamide, 6-Chloro-2-(p-chlorophenyl)-N,N-dipropylimidazo[1,2-a]pyridine-3-acetamide This compound was purchased from SigmaAldrich.

P7C3-S266: TRO 19622, also known as Cholest-4-en-3-one, oxime

This compound was purchased from SigmaAldrich.

P7C3-S267: (+)-a-tocopherol

This compound was purchased from SigmaAldrich.

P7C3-S268: 3-amino-1H-indole-2-carbonitrile

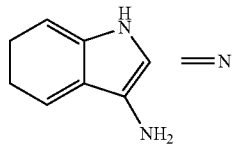

The title compound was made analogously to P7C3-S222. MS (ESI) m/z: 158.0 [M+H]$^+$, C9H7N3 requires 157.1.

P7C3-S269:
8-bromo-1H-pyrimido[5,4-b]indole-2,4(3H,5H)-dione

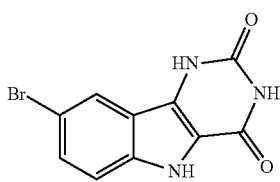 [SMILES: O=c1[nH]c(=O)c2[nH]c3ccc(Br)cc3c2[nH]1]

The title compound was synthesized following a reported procedure (Reichelt et al. US2011/0021511 A1, incorporated herein by reference).
$^1$H NMR (d$_6$-DMSO, 400 MHz) δ 11.97 (s, 1H), 11.57 (s, 1H), 11.15 (s, 1H), 8.13 (s, 1H), 7.46 (d, 1H, J=8.9 Hz), 7.36 (d, 1H, J=8.9 Hz). MS (ESI) m/z 281.8 [M+H]$^+$ ([M+H]$^+$, C$_{10}$H$_7$BrN$_3$O$_2$ requires 281.0).

P7C3-S270: 8-bromo-2-(dimethylamino)-5H-pyrimido[5,4-b]indol-4-ol

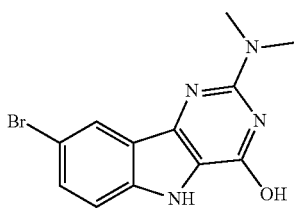 [SMILES: CN(C)c1nc(O)c2[nH]c3ccc(Br)cc3c2n1]

P7C3-S270 was synthesized and isolated in 72% yield analogously to P7C3-S245 except P7C3-S222 was used.
$^1$H NMR (d$_6$-DMSO, 400 MHz) δ 11.60 (s, 1H), 11.13 (brs, 1H), 7.97 (s, 1H), 7.45 (d, 1H, J=8.8 Hz), 7.36 (d, 1H, J=8.8 Hz), 3.09 (s, 6H). MS (ESI) m/z 307.8 [M+H]$^+$ ([M+H]$^+$, C$_{12}$H$_{12}$BrN$_4$O requires 308.1).

P7C3-S272: 8-bromo-1,3,5-trimethyl-1H-pyrimido[5,4-b]indole-2,4(3H,5H)-dione

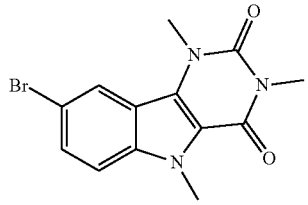 [SMILES: Cn1c(=O)c2c(c3cc(Br)ccc3n2C)n(C)c1=O]

NaH (0.087 g, of 60% suspension (in oil), 2.16 mmol) was added to a solution of P7C3-S269 (0.100 g, 0.36 mmol) in dry DMF (1.8 mL) at 0° C. and stirred for 30 min. Then, MeI (168 μL 2.7 mmol) was added dropwise to the reaction mixture. The reaction was warmed to room temperature and stirred for 3 h. Upon completion, the product was precipitated by the addition of water, collected by filtration and washed with water. The title compound was isolated as a brown solid (0.115 g, 99%).
$^1$H NMR (CDCl$_3$-MeOD [4:2], 500 MHz) δ 7.96 (d, 1H, J=1.7 Hz), 7.39 (dd, 1H, J=1.7, 9.0 Hz), 7.20 (d, 1H, J=9.0 Hz), 3.96 (s, 3H), 3.74 (s, 3H), 3.30 (s, 3H). MS (ESI) m/z 321.8 [M−H]$^−$ ([M−H]$^−$, C$_{13}$H$_{11}$BrN$_3$O$_2$ requires 321.1).

P7C3-S275: 8-bromo-4-methoxy-N,N,5-trimethyl-5H-pyrimido[5,4-b]indol-2-amine

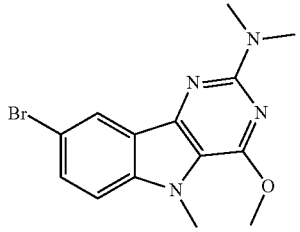 [SMILES: COc1nc(N(C)C)nc2c3cc(Br)ccc3n(C)c12]

P7C3-S275 was synthesized and isolated in 24% yield analogously to P7C3-S272 except P7C3-S270 was used.
$^1$H NMR (CDCl$_3$, 500 MHz) δ 8.30 (d, 1H, J=1.7 Hz), 7.53 (dd, 1H, J=1.7, 8.8 Hz), 7.18 (d, 1H, J=8.8 Hz), 4.10 (s, 3H), 3.93 (s, 3H), 3.25 (s, 6H). MS (ESI) m/z 336.0 [M+H]$^+$ ([M+H]$^+$, C$_{14}$H$_{16}$BrN$_4$O requires 336.2).

P7C3-S276:
3-amino-5-methoxy-1H-indole-2-carbonitrile

Step 1. Synthesis of
2-((cyanomethyl)amino)-5-methoxybenzonitrile

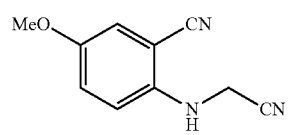 [SMILES: COc1ccc(NCC#N)c(C#N)c1]

Following a reported procedure (Michaelidou, S. S.; Koutentis, P. A. *Tetrahedron* 2010, 66, 685-688), 2-amino-5-methoxybenzonitrile (Manetsch, R. et al. *Chem. Eur. J.* 2004, 10, 2487-2506) (0.109 g, 0.74 mmol) was treated with paraformaldehyde (0.024 mg, 0.81 mmol), potassium cyanide (0.053 g, 0.81 mmol), zinc chloride (0.201 g, 1.473 mmol) and sulfuric acid (1 drop) in acetic acid (2.2 mL) in a sealed tube. The mixture was then stirred at 55° C. overnight. The reaction mixture was allowed to cool to room temperature, poured onto ice and made pH neutral with $Na_2CO_3$. Filtration of the precipitate gave the title compound (0.068 g, 50%).

$^1$H NMR (CDCl$_3$, 400 MHz) δ 7.11 (dd, 1H, J=2.8, 9.1 Hz), 6.98 (d, 1H, J=2.8 Hz), 6.75 (d, 1H, J=9.1 Hz), 4.15 (s, 2H), 3.74 (s, 3H).

MS (ESI) m/z 188.1 [M+H]$^+$ ([M+H]$^+$, $C_{10}H_{10}N_3O$ requires 188.2).

Step 2. Synthesis of
3-amino-5-methoxy-1H-indole-2-carbonitrile
(P7C3-S276)

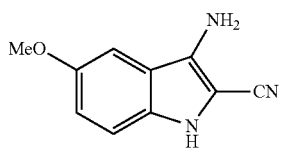 [SMILES: COc1ccc2[nH]c(C#N)c(N)c2c1]

P7C3-S276 (Step 2) was synthesized and isolated in quantitative yield analogously to P7C3-S222 (Step 2) except 2-((cyanomethyl)amino)-5-methoxybenzonitrile was used.

$^1$H NMR (CDCl$_3$, 400 MHz) δ 7.11 (d, 1H, J=9.0 Hz), 6.94 (dd, 1H, J=2.4, 9.0 Hz), 6.85 (d, 1H, J=2.3 Hz), 3.79 (s, 3H), 2.98 (brs, 2H). MS (ESI) m/z 188.1 [M+H]$^+$ ([M+H]$^+$, $C_{10}H_{10}N_3O$ requires 188.2).

P7C3-S277: 1-(3-(3,6-dibromo-9H-carbazol-9-yl)-2-hydroxypropyl)-3-phenylurea

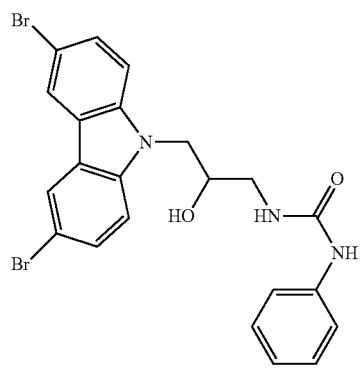 [SMILES: O=C(NCC(O)Cn1c2ccc(Br)cc2c2cc(Br)ccc21)Nc1ccccc1]

1-amino-3-(3,6-dibromo-9H-carbazol-9-yl)propan-2-ol (100 mg, 0.2518 mmol), potassium carbonate (41.8 mg, 0.3022 mmol), and phenyl isocyanate (33 µL, 0.3022 mmol) were dissolved in 5 mL THF. The reaction proceeded under inert atmosphere overnight. The reaction was quenched with water and the vial allowed to sit for one hour. A thin orange layer was carefully removed from the bottom of the vial and concentrated to give yellow residue. This was purified by column chromatography using 5% MeOH/DCM as the eluent to afford 10.1 mg (7.8% yield) of product as a translucent solid.

$^1$H NMR (500 MHz, CD$_3$OD) δ 8.16 (s, 2H), 7.63-7.50 (m, 4H), 7.25-7.15 (m, 4H), 7.00 (d, J=7.1 Hz, 1H), 5.16 (t, J=6.1 Hz, 1H), 4.54 (d, J=6.1 Hz, 2H), 2.89 (d, J=5.8 Hz, 2H). MS (ESI) m/z=516.0 ([M+H]$^+$, C22H19Br2N3O2 requires 514.98.

P7C3-S280: 3-bromo-6,9-dimethyl-9H-carbazole

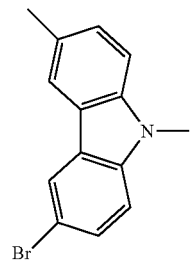

3-bromo-6-methyl-9H-carbazole (100 mg, 0.3844 mmol), NaH (18 mg, 0.4497 mmol, 60%), and iodomethane (32 µL, 0.5113 mmol) were dissolved in 0.3 mL DMF. The mixture was heated to 60° C. for six hours. The reaction mixture was then quenched with water to give product as a white precipitate. Product was collected via vacuum filtration and rinsed with hexanes. 85.1 mg (83.3% yield) product was collected.

$^1$H NMR (400 MHz, CDCl$_3$) δ 8.16 (d, J=2.0 Hz, 1H), 7.83 (dt, J=1.7, 0.9 Hz, 1H), 7.52 (dd, J=8.6, 2.0 Hz, 1H), 7.33 (d, J=1.6 Hz, 0H), 7.31 (d, J=1.6 Hz, 1H), 7.30 (d, J=0.7 Hz, 1H), 7.28 (s, OH), 7.26 (s, 1H), 7.23 (s, OH), 3.81 (s, 3H), 2.53 (s, 3H). MS (APCI) m/z=274.0 ([M+H]$^+$, $C_{14}H_{12}BrN$ requires 273.02.

Additional compounds include:

(P7C3-S76)

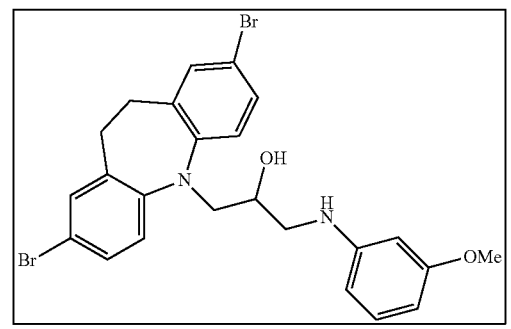

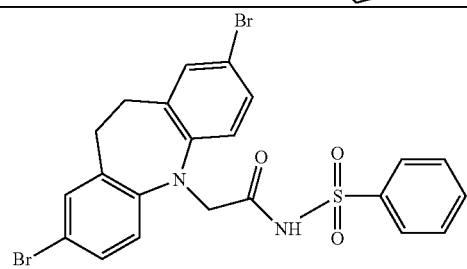

-continued

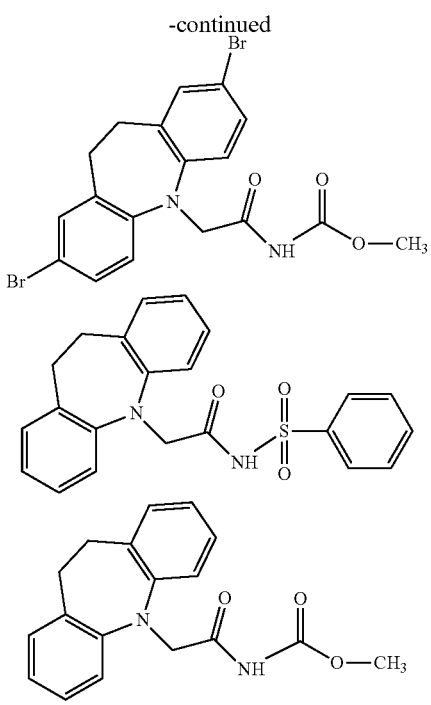

Pro-Neurogenic Efficacy/Neuroprotection Activity of Various Compounds:

Compounds were administered at a concentration of 10 μM for each molecule. After seven days of infusion at a constant rate of 0.5 μL/hour, a total of 84 μL of volume will have left the pump (0.00084 μMoles) and entered the cerebrospinal fluid. The average volume of a brain from a 12 week old male, C57/B6 mouse in the study is 500 mm³. The maximal amount of drug was estimated that could potentially be present in the brain, taking the extreme and unlikely scenario of 100% absorbance of the drug into brain tissue and 0% clearance throughout the seven day infusion period. Under these conditions, at the end of one week of infusion each compound would be present at 1.7 μMolar concentration. Since the actual amount of chemical compound in the brain is likely to be only a fraction of this predicted level, it is reasonable to estimate that compounds were administered at mid to low-nanomolar concentrations.

During compound infusion, animals were intraperitoneally (IP) injected daily with the thymidine analog, bromodeoxyuridine (BrdU), as a means of scoring the birth and survival of proliferating neural precursor cells in the hippocampus. Because both social interaction and voluntary exercise are known to stimulate hippocampal neurogenesis, mice were housed individually without access to running wheels throughout the screening period. Following the week-long period of compound administration, animals were perfused and sacrificed. Dissected brain tissue was fixed, embedded, sectioned, stained with antibodies to BrdU, and evaluated by light microcopy as a means of quantifying neurogenesis and survival of newborn neural precursor cells localized to the subgranular layer of the dentate gyms on the brain hemisphere contralateral to the side of mini-pump cannulation. Every fifth section throughout the entire rostral-caudal extent of the hippocampus was analyzed, and the total number of BrdU+ cells was normalized against the measured volume of the dentate gyms.

Intracranial infusions of either fibroblast growth factor 2 (FGF-2) or artificial cerebral spinal fluid (aCSF) vehicle via the same, week-long protocol were employed as positive and negative controls. There was no difference in the number of BrdU-labeled cells in the dentate gyrus between mice subjected to surgical pump implantation and infusion with vehicle, and mice having had no surgery.

Various compounds were tested in vivo for dose-responsive neurotrophic efficacy. The results are shown in Table 1.

TABLE 1

In Vivo Activity

| Test Material | ($\times 10^{-06}$) BrdU+ cells/mm³ dentate gyrus | SEM: (standard error of the mean) |
|---|---|---|
| Vehicle | 14.5 | 1.08 |
| FGF-2: (fibroblast growth factor 2) | 28.4 | 2.12 |
| P7C3-S76 | 28.3 | 1.7 |
| P7C3-S132 | 22.8 | 0.9 |
| P7C3-S133 | 20.2 | 1.9 |
| P7C3-S134 | 19.4 | 2.1 |
| P7C3-S135 | 14.2 | 0.9 |
| P7C3-S139 | 24.9 | 1.8 |
| P7C3-S140 | 23.4 | 3 |
| P7C3-S143 | 14.5 | 1.5 |
| P7C3-S144 | 18.1 | 1.3 |
| P7C3-S145 | 25 | 3.1 |
| P7C3-S148 | 22.6 | 1.7 |
| P7C3-S149 | 23.2 | 1.3 |
| P7C3-S152 | 26.8 | 2.6 |
| P7C3-S158 | 25 | 0.8 |
| P7C3-S162 | 25.2 | 3.6 |
| P7C3-S163 | 24.2 | 2.6 |
| P7C3-S169 | 18.4 | 1 |
| P7C3-S170 | 22.4 | 1.1 |
| P7C3-S171 | 26.2 | 2.1 |
| P7C3-S180 | 25.9 | 4.6 |
| P7C3-S180 | 18.7 | 1.6 |
| P7C3-S185 | 25.1 | 2.3 |
| P7C3-S189 | 13.7 | 1.3 |
| P7C3-S193 | 15.6 | 0.9 |
| P7C3-S199 | 26.5 | 3-Feb |
| P7C3-S200 | 22.1 | 1.6 |
| P7C3-S201 | 24.8 | 2.8 |
| P7C3-S203 | 21.5 | 2.8 |
| P7C3-S206 | 29.6 | 1.4 |
| P7C3-S207 | 32.4 | 2.6 |
| P7C3-S209 | 30 | 0.4 |
| P7C3-S210 | 21.4 | 2 |
| P7C3-S211 | 23 | 3 |
| P7C3-S212 | 20.5 | 2.4 |
| P7C3-S216 | 25.9 | 1 |
| P7C3-S222 | 30.1 | 3.5 |
| P7C3-S223 | 15.8 | 0.9 |
| P7C3-S224 | 20.2 | 0.8 |
| P7C3-S225 | 30.4 | 2.2 |
| P7C3-S227 | 25.8 | 1.5 |
| P7C3-S228 | 40.3 | 2.5 |
| P7C3-S229 | 26.5 | 3.7 |
| P7C3-S230 | 30.5 | 1.7 |
| P7C3-S231 | 26.1 | 1.8 |
| P7C3-S232 | 16.8 | 1.3 |
| P7C3-S235 | 23.4 | 2.1 |
| P7C3-S236 | 24.6 | 2.6 |
| P7C3-S237 | 23.5 | 1.3 |
| P7C3-S238 | 18.8 | 1.5 |
| P7C3-S239 | 22.8 | 1.4 |
| P7C3-S240 | 28.5 | 2.5 |
| P7C3-S241 | 30.9 | 1.5 |
| P7C3-S242 | 21.5 | 1.7 |
| P7C3-S244 | 23.2 | 1.9 |
| P7C3-S245 | 32.4 | 1.8 |
| P7C3-S246 | 29 | 2.4 |
| P7C3-S247 | 31.1 | 1 |
| P7C3-S248 | 20.1 | 1.9 |
| P7C3-S249 | 34.8 | 4.1 |
| P7C3-S250 | 23.7 | 1.9 |
| P7C3-S251 | 17.7 | 1.2 |

TABLE 1-continued

In Vivo Activity

| Test Material | ($\times 10^{-06}$) BrdU+ cells/mm$^3$ dentate gyrus | SEM: (standard error of the mean) |
|---|---|---|
| P7C3-S252 | 33.2 | 1.2 |
| P7C3-S253 | 28.5 | 3 |
| P7C3-S254 | 25.5 | 0.7 |
| P7C3-S256 | 31.5 | 3.5 |
| P7C3-S257 | 29.4 | 2.7 |
| P7C3-S258 | 29.8 | 2.3 |
| P7C3-S262 | 18 | 1.2 |
| P7C3-S264 | 20.6 | 0.8 |
| P7C3-S265 | 29.3 | 3.6 |
| P7C3-S266 | 42.3 | 2.3 |
| P7C3-S267 | 21.4 | 1.2 |
| P7C3-S268 | 32.1 | 1.6 |
| P7C3-S269 | 35.4 | 3.7 |
| P7C3-S270 | 28 | 4.3 |
| P7C3-S275 | 20.5 | 2.3 |
| P7C3-S276 | 29.3 | 3 |
| P7C3-S277 | 20.3 | 2.2 |
| P7C3-S280 | 25.1 | 1.5 |

Compounds were evaluated for pro-neurogenic efficacy/neuroprotection in a standard in vivo hippocampal neurogenesis assay at 10 µM concentration in four 12 week old adult male C57/B16 mice. As shown in Table 1, many compounds showed high pro-neurogenic and/or neuroprotective activity in this assay. As such, these compounds can be used to promote neurogenesis and/or reduce neuronal cell death, which are the underlying causes for a variety of neuropsychiatric and neurodegenerative diseases.

Additional methods, assays and animal models for testing pro-neurogenic and/or neuroprotective activity are described in detail in U.S. Pat. No. 8,362,277, U.S. Publication No. 2011/0015217, U.S. Publication No. 2012/0022096 and U.S. Publication No. 2013/0040977, the entire disclosures of which are incorporated herein by reference in their entirety. For example, one of ordinary skill in the art would understand that the methods and animal models such as in vivo screening for pro-neurogenic compounds, structure activity relationship study, neuron survival study, neuronal apoptosis assay, mitochondrial integrity assay, aged rats model, NPAS3-deficient mice, G93A-SOD1 transgenic mice model of Amyotrophic Lateral Sclerosis, MPTP (1-methyl-4-phenyl-1,2,3,6-tetrahydropyridine) toxicity model of Parkinson's disease, and R6/2 transgenic mice model of Huntington's Disease described in these patent and patent application publications can be used to further demonstrate the efficacy of the compounds described herein.

Compound Forms and Salts

The compounds described herein may contain one or more asymmetric centers and thus occur as racemates and racemic mixtures, enantiomerically enriched mixtures, single enantiomers, individual diastereomers and diastereomeric mixtures. All such isomeric forms of these compounds are expressly included in the presently disclosed embodiments. The compounds of the presently disclosed embodiments may also contain linkages (e.g., carbon-carbon bonds, carbon-nitrogen bonds such as amide bonds) wherein bond rotation is restricted about that particular linkage, e.g. restriction resulting from the presence of a ring or double bond. Accordingly, all cis/trans and E/Z isomers and rotational isomers are expressly included in the presently disclosed embodiments. The compounds of the presently disclosed embodiments may also be represented in multiple tautomeric forms, in such instances, the presently disclosed embodiments expressly include all tautomeric forms of the compounds described herein, even though only a single tautomeric form may be represented. All such isomeric forms of such compounds are expressly included in the presently disclosed embodiments.

Optical isomers can be obtained in pure form by standard procedures known to those skilled in the art, and include, but are not limited to, diastereomeric salt formation, kinetic resolution, and asymmetric synthesis. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, NY, 1962); Wilen, S. H. Tables of Resolving Agents and Optical Resolutions p. 268 (E. L. Eliel, Ed., Univ. of Notre Dame Press, Notre Dame, Ind. 1972), each of which is incorporated herein by reference in their entireties. It is also understood that the presently disclosed embodiments encompass all possible regioisomers, and mixtures thereof, which can be obtained in pure form by standard separation procedures known to those skilled in the art, and include, but are not limited to, column chromatography, thin-layer chromatography, and high-performance liquid chromatography.

The compounds of the presently disclosed embodiments include the compounds themselves, as well as their salts and their prodrugs, if applicable. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion. Examples of prodrugs include $C_{1-6}$ alkyl esters of carboxylic acid groups, which, upon administration to a subject, are capable of providing active compounds.

Pharmaceutically acceptable salts of the compounds of the presently disclosed embodiments include those derived from pharmaceutically acceptable inorganic and organic acids and bases. As used herein, the term "pharmaceutically acceptable salt" refers to a salt formed by the addition of a pharmaceutically acceptable acid or base to a compound disclosed herein. As used herein, the phrase "pharmaceutically acceptable" refers to a substance that is acceptable for use in pharmaceutical applications from a toxicological perspective and does not adversely interact with the active ingredient.

Examples of suitable acid salts include acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the presently disclosed embodiments and their pharmaceutically acceptable acid addition salts. Salts derived from appropriate bases include alkali metal (e.g., sodium), alkaline earth metal (e.g., magnesium), ammonium and N-(alkyl)$_4^+$ salts. The presently disclosed embodiments also envision the quaternization of any basic nitrogen-containing groups of the compounds disclosed herein. Water or oil-soluble or dispersible products may be obtained by such quaternization. Salt forms of the compounds of any of the formulae herein can be amino acid salts of carboxyl groups (e.g. L-arginine, -lysine, -histidine salts).

Lists of suitable salts are found in Remington's Pharmaceutical Sciences, 17th ed., Mack Publishing Company, Easton, Pa., 1985, p. 1418; Journal of Pharmaceutical Science, 66, 2 (1977); and "Pharmaceutical Salts: Properties, Selection, and Use A Handbook; Wermuth, C. G. and Stahl, P. H. (eds.) Verlag Helvetica Chimica Acta, Zurich, 2002 [ISBN 3-906390-26-8] each of which is incorporated herein by reference in their entireties.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the presently disclosed embodiments.

In addition to salt forms, the presently disclosed embodiments provide compounds which are in a prodrug form. Prodrugs of the compounds described herein are those compounds that undergo chemical changes under physiological conditions to provide the compounds of the presently disclosed embodiments. Additionally, prodrugs can be converted to the compounds of the presently disclosed embodiments by chemical or biochemical methods in an ex vivo environment. For example, prodrugs can be slowly converted to the compounds of the presently disclosed embodiments when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the presently disclosed embodiments which is administered as an ester (the "prodrug"), but then is metabolically hydrolyzed to the carboxylic acid, the active entity. Additional examples include peptidyl derivatives of a compound of the presently disclosed embodiments.

The presently disclosed embodiments also include various hydrate and solvate forms of the compounds.

The compounds of the presently disclosed embodiments may also contain unnatural proportions of atomic isotopes at one or more of the atoms that constitute such compounds. For example, the compounds may be radiolabeled with radioactive isotopes, for example tritium ($^3H$), iodine-125 ($^{125}I$) or carbon-14 ($^{14}C$). All isotopic variations of the compounds of the presently disclosed embodiments, whether radioactive or not, are intended to be encompassed within the scope of the presently disclosed embodiments.

Synthesis

The compounds of the presently disclosed embodiments can be conveniently prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures. Those skilled in the art of organic synthesis will recognize that the nature and order of the synthetic steps presented may be varied for the purpose of optimizing the formation of the compounds described herein.

Synthetic chemistry transformations (including protecting group methodologies) useful in synthesizing the compounds described herein are known in the art and include, for example, those such as described in R. C. Larock, *Comprehensive Organic Transformations*, 2d. ed., Wiley-VCH Publishers (1999); P. G. M. Wuts and T. W. Greene, *Protective Groups in Organic Synthesis*, 4th Ed., John Wiley and Sons (2007); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The processes described herein can be monitored according to any suitable method known in the art. For example, product formation can be monitored by spectroscopic means, such as nuclear magnetic resonance spectroscopy (e.g., $^1H$ or $^{13}C$), infrared spectroscopy (FT-IR), spectrophotometry (e.g., UV-visible), or mass spectrometry (MS), or by chromatography such as high performance liquid chromatography (HPLC) or thin layer chromatography (TLC).

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis*, 2d. Ed., Wiley & Sons, 1991, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvents. Depending on the particular reaction step, suitable solvents for a particular reaction step can be selected.

Resolution of racemic mixtures of compounds can be carried out by any of numerous methods known in the art. An exemplary method includes preparation of the Mosher's ester or amide derivative of the corresponding alcohol or amine, respectively. The absolute configuration of the ester or amide is then determined by proton and/or $^{19}F$ NMR spectroscopy. An exemplary method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Resolution of racemic mixtures can also be carried out by elution on a column packed with an optically active resolving agent (e.g., dinitrobenzoylphenylglycine). Suitable elution solvent compositions can be determined by one skilled in the art.

In certain embodiments, compounds or intermediates thereof maybe synthesized by the following representative scheme.

Pharmaceutical Compositions

The term "pharmaceutically acceptable carrier" refers to a carrier or adjuvant that may be administered to a subject (e.g., a patient), together with a compound of the presently disclosed embodiments, and which does not destroy the pharmacological activity thereof and is nontoxic when administered in doses sufficient to deliver a therapeutic amount of the compound.

Pharmaceutically acceptable carriers, adjuvants and vehicles that may be used in the compositions of the presently disclosed embodiments include, but are not limited

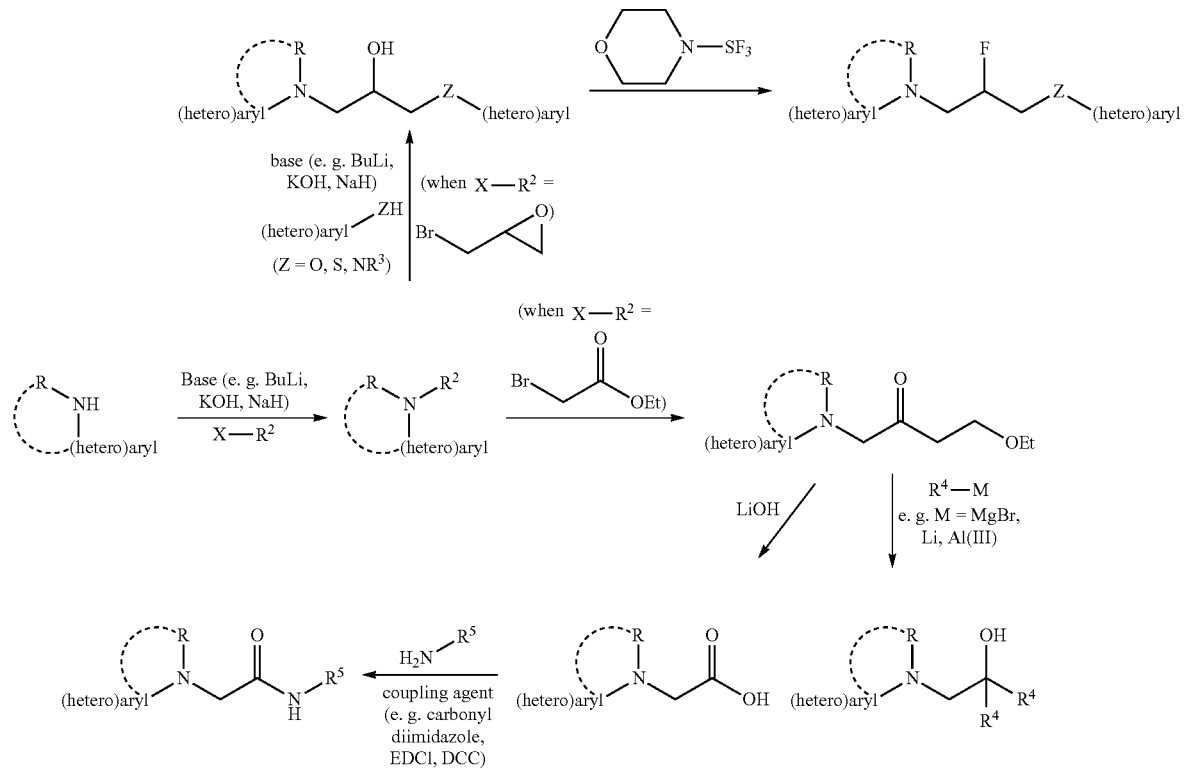

In the above scheme, "(hetero)aryl" means an aryl or heteroaryl group. R, $R^2$, $R^3$, $R^4$ and $R^5$ represent generic groups or substitutents suitable for the corresponding chemical compound or reaction, as one of ordinary skill in organic chemistry would understand. For example, R together with the nitrogen it is connected to can form a C4 or C6 ring, which can be connected to one or more aryl and/or heteroaryl (e.g., optionally substituted phenyl, pyridine or pyrimidine). Groups $R^2$, $R^3$ and $R^5$ may be any group that can form a bond with nitrogen as generally known in the art, such as alkyl, alkenyl, cycloalkyl, heterocycloalkyl, aryl, heteroaryl, and/or sulfonyl, each optionally substituted with one or more halo, hydroxyl, alkoxyl, carboxyl, alkoxycarbonyl, amine, cyano, azide, sulfonyl, alkyl, alkenyl, cycloalkyl, aryl and/or heteroaryl. $R^4$.M may be a salt in which $R^4$ is a nucleophilic group, such as a negatively charged alkyl group, and M is a positively changed ion such as a metal ion.

Additional synthesis procedures are described in detail in U.S. Pat. No. 8,362,277, U.S. Publication No. 2011/0015217, U.S. Publication No. 2012/0022096 and U.S. Publication No. 2013/0040977, the entire disclosures of which are incorporated herein by reference in their entirety.

to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts, or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The compositions for administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules, losenges or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

The amount administered depends on the compound formulation, route of administration, etc. and is generally empirically determined in routine trials, and variations will necessarily occur depending on the target, the host, and the route of administration, etc. Generally, the quantity of active compound in a unit dose of preparation may be varied or adjusted from about 1, 3, 10 or 30 to about 30, 100, 300 or 1000 mg, according to the particular application. In a particular embodiment, unit dosage forms are packaged in a multipack adapted for sequential use, such as blisterpack, comprising sheets of at least 6, 9 or 12 unit dosage forms. The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired.

The following are examples (Formulations 1-4) of capsule formulations.

| Capsule Formulations | Formulation 1; mg/capsule | Formulation 2; mg/capsule | Formulation 3; mg/capsule | Formulation 4; mg/capsule |
| --- | --- | --- | --- | --- |
| Compound (solid solution) | 100 | 400 | 400 | 200 |
| Silicon Dioxide | 0.625 | 2.5 | 3.75 | 1.875 |
| Magnesium Stearate NF2 | 0.125 | 0.5 | 0.125 | 0.625 |
| Croscarmellose Sodium NF | 11.000 | 44.0 | 40.0 | 20.0 |
| Pluronic F68 NF | 6.250 | 25.0 | 50.0 | 25.0 |
| Silicon Dioxide NF | 0.625 | 2.5 | 3.75 | 1.875 |
| Magnesium Stearate NF | 0.125 | 0.5 | 1.25 | 0.625 |
| Total | 118.750 | 475.00 | 475.00 | 475.00 |
| Capsule Size | No. 4 | No. 0 | No. 0 | No. 2 |

Preparation of Solid Solution

Crystalline compound (e.g., 80 g/batch) and the povidone (NF K29/32 at 160 g/batch) are dissolved in methylene chloride (5000 mL). The solution is dried using a suitable solvent spray dryer and the residue reduced to fine particles by grinding. The powder is then passed through a 30 mesh screen and confirmed to be amorphous by x-ray analysis.

The solid solution, silicon dioxide and magnesium stearate are mixed in a suitable mixer for 10 minutes. The mixture is compacted using a suitable roller compactor and milled using a suitable mill fitted with 30 mesh screen. Croscarmellose sodium, Pluronic F68 and silicon dioxide are added to the milled mixture and mixed further for 10 minutes. A premix is made with magnesium stearate and equal portions of the mixture. The premix is added to the remainder of the mixture, mixed for 5 minutes and the mixture encapsulated in hard shell gelatin capsule shells.

Use

In one aspect, methods for treating (e.g., controlling, relieving, ameliorating, alleviating, or slowing the progression of) or methods for preventing (e.g., delaying the onset of or reducing the risk of developing) one or more diseases, disorders, or conditions caused by, or associated with, aberrant (e.g., insufficient) neurogenesis or accelerated neuron cell death in a subject in need thereof are featured. The methods include administering to the subject an effective amount of a compound of formula (I) (and/or a compound of any of the other formulae described herein) or a salt (e.g., a pharmaceutically acceptable salt) thereof as defined anywhere herein to the subject.

In another aspect, the use of a compound any of the other described herein or a salt (e.g., a pharmaceutically acceptable salt) thereof as defined anywhere herein in the preparation of, or for use as, a medicament for the treatment (e.g., controlling, relieving, ameliorating, alleviating, or slowing the progression of) or prevention (e.g., delaying the onset of or reducing the risk of developing) of one or more diseases, disorders, or conditions caused by, or associated with, aberrant (e.g., insufficient) neurogenesis or exacerbated neuronal cell death is featured.

In some embodiments, the one or more diseases, disorders, or conditions can include neuropathies, nerve trauma, and neurodegenerative diseases. In some embodiments, the one or more diseases, disorders, or conditions can be diseases, disorders, or conditions caused by, or associated with aberrant (e.g., insufficient) neurogenesis (e.g., aberrant hippocampal neurogenesis as is believed to occur in neuropsychiatric diseases) or accelerated death of existing neurons. Examples of the one or more neuropsychiatric and neurodegenerative diseases include, but are not limited to, schizophrenia, major depression, bipolar disorder, normal aging, epilepsy, traumatic brain injury, post-traumatic stress disorder, Parkinson's disease, Alzheimer's disease, Down syndrome, spinocerebellar ataxia, amyotrophic lateral sclerosis, Huntington's disease, stroke, radiation therapy, chronic stress, and abuse of neuro-active drugs (such as alcohol, opiates, methamphetamine, phencyclidine, and cocaine), retinal degeneration, spinal cord injury, peripheral nerve injury, physiological weight loss associated with various conditions, and cognitive decline associated with normal aging, radiation therapy, and chemotherapy. The resultant promotion of neurogenesis or survival of existing neurons (i.e. a resultant promotion of survival, growth, development, function and/or generation of neurons) may be detected directly, indirectly or inferentially from an improvement in, or an amelioration of one or more symptoms of the disease or disorder caused by or associated with aberrant neurogenesis or survival of existing neurons. Suitable assays which directly or indirectly detect neural survival, growth, development, function and/or generation are known in the art, including axon regeneration in rat models (e.g. Park et al., Science. 2008 Nov. 7; 322:963-6), nerve regeneration in a rabbit facial nerve injury models (e.g. Zhang et al., J Transl Med. 2008 Nov. 5; 6(1):67); sciatic nerve regeneration in rat models (e.g. Sun et al., Cell Mol. Neurobiol. 2008 Nov. 6); protection against motor neuron degeneration in mice (e.g. Poesen et al., J. Neurosci. 2008 Oct. 15; 28(42):10451-9); rat model of Alzheimer's disease, (e.g. Xuan et al., Neurosci Lett. 2008 Aug. 8; 440(3):331-5); animal models of depression (e.g. Schmidt et al., Behav Pharmacol. 2007 September; 18(5-6):391-418; Krishnan et al., Nature 2008, 455, 894-902); and/or those exemplified herein.

Administration

The compounds and compositions described herein can, for example, be administered orally, parenterally (e.g., subcutaneously, intracutaneously, intravenously, intramuscularly, intraarticularly, intraarterially, intrasynovially, intrasternally, intrathecally, intralesionally and by intracranial injection or infusion techniques), by inhalation spray, topically, rectally, nasally, buccally, vaginally, via an implanted reservoir, by injection, subdermally, intraperitoneally, transmucosally, or in an ophthalmic preparation, with a dosage ranging from about 0.01 mg/kg to about 1000 mg/kg, (e.g., from about 0.01 to about 100 mg/kg, from about 0.1 to about 100 mg/kg, from about 1 to about 100 mg/kg, from about 1 to about 10 mg/kg) every 4 to 120 hours, or according to the requirements of the particular drug. The interrelationship of dosages for animals and humans (based on milligrams per meter squared of body surface) is described by Freireich et al., Cancer Chemother. Rep. 50, 219 (1966). Body surface area may be approximately determined from height and weight of the patient. See, e.g., Scientific Tables, Geigy Pharmaceuticals, Ardsley, N.Y., 537 (1970). In certain embodiments, the compositions are administered by oral administration or administration by injection. The methods herein contemplate administration of an effective amount of compound or compound composition to achieve the desired or stated effect. Typically, the pharmaceutical compositions of the presently disclosed embodiments will be administered from about 1 to about 6 times per day or alternatively, as a continuous infusion. Such administration can be used as a chronic or acute therapy.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of the presently disclosed embodiments may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

In some embodiments, the compounds described herein can be coadministered with one or more other therapeutic agents. In certain embodiments, the additional agents may be administered separately, as part of a multiple dose regimen, from the compounds of the presently disclosed embodiments (e.g., sequentially, e.g., on different overlapping schedules with the administration of one or more compounds of formula (I) (including any subgenera or specific compounds thereof)). In other embodiments, these agents may be part of a single dosage form, mixed together with the compounds of the presently disclosed embodiments in a single composition. In still another embodiment, these agents can be given as a separate dose that is administered at about the same time that one or more compounds of formula (I) (including any subgenera or specific compounds thereof) are administered (e.g., simultaneously with the administration of one or more compounds of formula (I) (including any subgenera or specific compounds thereof)). When the compositions of the presently disclosed embodiments include a combination of a compound of the formulae described herein and one or more additional therapeutic or prophylactic agents, both the compound and the additional agent can be present at dosage levels of between about 1 to 100%, and more preferably between about 5 to 95% of the dosage normally administered in a monotherapy regimen.

The compositions of the presently disclosed embodiments may contain any conventional nontoxic pharmaceutically-acceptable carriers, adjuvants or vehicles. In some cases, the pH of the formulation may be adjusted with pharmaceutically acceptable acids, bases or buffers to enhance the stability of the formulated compound or its delivery form.

The compositions may be in the form of a sterile injectable preparation, for example, as a sterile injectable aqueous or oleaginous suspension. This suspension may be formulated according to techniques known in the art using suitable dispersing or wetting agents (for example, Tween 80) and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The compositions of the presently disclosed embodiments may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The compositions of the presently disclosed embodiments may also be administered in the form of suppositories for rectal administration. These compositions can be prepared by mixing a compound of the presently disclosed embodiments with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the compositions of the presently disclosed embodiments is useful when the desired treatment involves areas or organs readily accessible by topical application. For application topically to the skin, the composition should be formulated with a suitable ointment containing the active components suspended or dissolved in a carrier. Carriers for topical administration of the compounds of the presently disclosed embodiments include, but are not limited to, mineral oil, liquid petroleum, white petroleum, propylene glycol, polyoxyethylene polyoxypropylene compound, emulsifying wax and water. Alternatively, the composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The compositions of the presently disclosed embodiments may also be topically applied to the lower intestinal tract by rectal suppository formulation or in a suitable enema formulation.

In some embodiments, topical administration of the compounds and compositions described herein may be presented in the form of an aerosol, a semi-solid pharmaceutical composition, a powder, or a solution. By the term "a semi-solid composition" is meant an ointment, cream, salve, jelly, or other pharmaceutical composition of substantially similar consistency suitable for application to the skin. Examples of semi-solid compositions are given in Chapter 17 of The Theory and Practice of Industrial Pharmacy, Lachman, Lieberman and Kanig, published by Lea and Febiger (1970) and in Remington's Pharmaceutical Sciences, 21st Edition (2005) published by Mack Publishing Company, which is incorporated herein by reference in its entirety.

Topically-transdermal patches are also included in the presently disclosed embodiments. Also within the presently disclosed embodiments is a patch to deliver active chemotherapeutic combinations herein. A patch includes a material layer (e.g., polymeric, cloth, gauze, bandage) and the compound of the formulae herein as delineated herein. One side of the material layer can have a protective layer adhered to it to resist passage of the compounds or compositions. The patch can additionally include an adhesive to hold the patch in place on a subject. An adhesive is a composition, including those of either natural or synthetic origin, that when contacted with the skin of a subject, temporarily adheres to the skin. It can be water resistant. The adhesive can be placed on the patch to hold it in contact with the skin of the subject for an extended period of time. The adhesive can be made of a tackiness, or adhesive strength, such that it holds the device in place subject to incidental contact, however, upon an affirmative act (e.g., ripping, peeling, or other intentional removal) the adhesive gives way to the external pressure placed on the device or the adhesive itself, and allows for breaking of the adhesion contact. The adhesive can be pressure sensitive, that is, it can allow for positioning of the adhesive (and the device to be adhered to the skin) against the skin by the application of pressure (e.g., pushing, rubbing,) on the adhesive or device.

The compositions of the presently disclosed embodiments may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

A composition having the compound of the formulae herein and an additional agent (e.g., a therapeutic agent) can be administered using any of the routes of administration described herein. In some embodiments, a composition having the compound of the formulae herein and an additional agent (e.g., a therapeutic agent) can be administered using an implantable device. Implantable devices and related technology are known in the art and are useful as delivery systems where a continuous, or timed-release delivery of compounds or compositions delineated herein is desired. Additionally, the implantable device delivery system is useful for targeting specific points of compound or composition delivery (e.g., localized sites, organs). Negrin et al., Biomaterials, 22(6):563 (2001). Timed-release technology involving alternate delivery methods can also be used in the presently disclosed embodiments. For example, timed-release formulations based on polymer technologies, sustained-release techniques and encapsulation techniques (e.g., polymeric, liposomal) can also be used for delivery of the compounds and compositions delineated herein.

In an aspect, compounds of the presently disclosed embodiments may include those represented by formula (I):

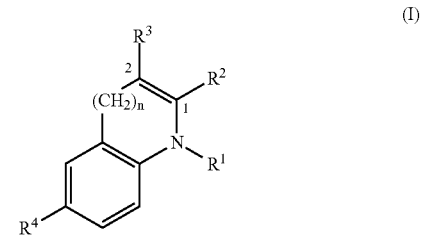

(I)

wherein:
$R^2$ and $R^3$, together with C1 and C2, form the optionally substituted phenyl, pyridine or pyrimidine ring of formulas (II)-(IV) described below, or are defined as $R^{2d}$ and $R^{3d}$ of formula (V), respectively;
$R^4$ is defined as any one of $R^{4a}$-$R^{4d}$ in formulas (II)-(IV); and
n is 0 or 2.

For example, a compound or pharmaceutically acceptable salt thereof, for promoting neurogenesis and/or reducing neuronal cell death, can be represented by formula (II):

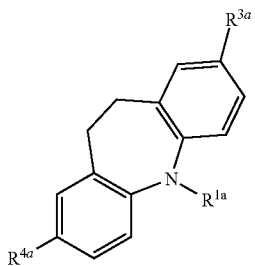

(II)

wherein $R^{1a}$ is selected from the group consisting of: —$CH_2$—$C(O)$—$Z^{1a}$ and —$CH_2$—$C(R^{A1})(R^{A2})$—$CH_2$—$Z^{2a}$; and $R^{3a}$ and $R^{4a}$ are each independently selected from the group consisting of: hydrogen, halo, hydroxyl, $C_{1-3}$ alkoxyl, cyano, carboxyl, and formamide;

wherein $Z^{1a}$ is selected from the group consisting of: hydroxyl; $C_{1-6}$ alkoxyl; amine optionally substituted with 1 or more $C_{1-12}$ alkyl, $C_{2-12}$ alkenyl, $C_{3-12}$ cycloalkyl, $C_{1-12}$ alkyl sulfonyl optionally substituted with 1-6 halo, $C_{6-12}$ aryl sulfonyl optionally substituted with 1-6 halo, $C_{4-12}$ heteroaryl sulfonyl optionally substituted with 1-6 halo, $C_{2-12}$ alkyl carbonyl optionally substituted with 1-6 halo, and/or $C_{2-12}$ carboxyalkyl optionally substituted with 1-6 halo; $C_{2-12}$ heterocyclyl; $C_{6-12}$ aryl optionally substituted with 1 or more halo, hydroxyl, $C_{1-6}$ alkyl and/or $C_{1-6}$ alkoxyl; and $C_{4-12}$ heteroaryl optionally substituted with 1 or more halo, hydroxyl, $C_{1-6}$ alkyl and/or $C_{1-6}$ alkoxyl;

wherein one of $R^{A1}$ and $R^{A2}$ is hydroxyl, halo, or amine optionally substituted with 1 or more $C_{1-6}$ alkyl, $C_{2-6}$ alkenyl, $C_{3-6}$ cycloalkyl, $C_{2-6}$ heterocyclyl, $C_{6-12}$ aryl, and/or $C_{4-12}$ heteroaryl; and the other of $R^{A1}$ and $R^{A2}$ is hydrogen;

wherein $Z^{2a}$ is selected from the group consisting of: halo, $O(R^a)$, $S(R^b)$ and $N(R^c)(R^d)$;

wherein $R^a$ and $R^b$ are each independently selected from the group consisting of: $C_{1-12}$ alkyl; $C_{2-12}$ alkenyl; $C_{3-12}$ cycloalkyl; $C_{2-6}$ heterocyclyl; $C_{6-12}$ aryl optionally substituted with 1 or more halo, hydroxyl, $C_{1-6}$ alkyl and/or $C_{1-6}$ alkoxyl; and $C_{4-12}$ heteroaryl optionally substituted with 1 or more halo, hydroxyl, $C_{1-6}$ alkyl and/or $C_{1-6}$ alkoxyl;

wherein $R^c$ and $R^d$ are each independently selected from the group consisting of: hydrogen; $C_{1-12}$ alkyl; $C_{2-12}$ alkenyl; $C_{3-12}$ cycloalkyl; $C_{2-6}$ heterocyclyl; $C_{6-12}$ aryl optionally substituted with 1 or more halo, hydroxyl, $C_{1-6}$ alkyl and/or $C_{1-6}$ alkoxyl; and $C_{4-12}$ heteroaryl optionally substituted with 1 or more halo, hydroxyl, $C_{1-6}$ alkyl and/or $C_{1-6}$ alkoxyl; or wherein $R^c$ and $R^d$ together with the nitrogen they are attached to form a $C_{4-14}$ heteroaryl optionally substituted with 1 or more halo, hydroxyl, $C_{1-6}$ alkyl and/or $C_{1-6}$ alkoxyl.

In some embodiments, one or more of the following definitions apply:

(6) $R^{3a}$ and $R^{4a}$ are both hydrogen or both bromo;
(7) $Z^{1a}$ is hydroxyl or amine optionally substituted with 1 or more $C_{1-12}$ alkyl, $C_{2-12}$ alkenyl, and/or $C_{3-12}$ cycloalkyl;
(8) one of $R^{A1}$ and $R^{A2}$ is hydroxyl or halo; and the other of $R^{A1}$ and $R^{A2}$ is hydrogen;
(9) $Z^{2a}$ is $O(R^a)$ or $S(R^b)$; and/or
(10) $Z^{2a}$ is $N(R^c)(R^d)$.

For example, $R^{1a}$ may be —$CH_2$—$C(O)$—$Z^{1a}$ or —$CH_2$—$C(R^{A1})(R^{A2})$—$CH_2$—$Z^{2a}$.

When $R^{1a}$ is —$CH_2$—$C(O)$—$Z^{1a}$, $Z^{1a}$ may be hydroxyl or $C_{1-6}$ alkoxyl. $Z^{1a}$ may also be amine optionally substituted with 1 or more $C_{1-12}$ alkyl, $C_{2-12}$ alkenyl, $C_{3-12}$ cycloalkyl, $C_{1-12}$ alkyl sulfonyl optionally substituted with 1-6 halo, $C_{6-12}$ aryl sulfonyl optionally substituted with 1-6 halo, $C_{4-12}$ heteroaryl sulfonyl optionally substituted with 1-6 halo, $C_{2-12}$ alkyl carbonyl optionally substituted with 1-6 halo, and/or $C_{2-12}$ carboxyalkyl optionally substituted with 1-6 halo. For example, $Z^{1a}$ can be amine optionally substituted with 1 or more $C_{1-12}$ alkyl, $C_{2-12}$ alkenyl, and/or $C_{3-12}$ cycloalkyl. $Z^{1a}$ may also be $C_{2-12}$ heterocyclyl; $C_{6-12}$ aryl optionally substituted with 1 or more halo, hydroxyl, $C_{1-6}$ alkyl and/or $C_{1-6}$ alkoxyl; or $C_{4-12}$ heteroaryl optionally substituted with 1 or more halo, hydroxyl, $C_{1-6}$ alkyl and/or $C_{1-6}$ alkoxyl.

When $R^{1a}$ is —$CH_2$—$C(R^{A1})(R^{A2})$—$CH_2$—$Z^{2a}$, both of $R^{A1}$ and $R^{A2}$ can be hydrogen. Alternatively, one of $R^{A1}$ and $R^{A2}$ is hydroxyl, halo (e.g., fluoro), or amine optionally substituted with 1 or more $C_{1-6}$ alkyl (e.g., methyl), $C_{2-6}$ alkenyl, $C_{3-6}$ cycloalkyl, $C_{2-6}$ heterocyclyl, $C_{6-12}$ aryl, and/or $C_{4-12}$ heteroaryl; and the other of $R^{A1}$ and $R^{A2}$ is hydrogen. $Z^{2a}$ can be halo, $O(R^a)$, $S(R^b)$ or $N(R^c)(R^d)$. $R^a$ and $R^b$ are each common substitutients such as: $C_{1-12}$ alkyl; $C_{2-12}$ alkenyl; $C_{3-12}$ cycloalkyl; $C_{2-6}$ heterocyclyl; $C_{6-12}$ aryl optionally substituted with 1 or more halo, hydroxyl, $C_{1-6}$ alkyl and/or $C_{1-6}$ alkoxyl; and $C_{4-12}$ heteroaryl optionally substituted with 1 or more halo, hydroxyl, $C_{1-6}$ alkyl and/or $C_{1-6}$ alkoxyl. $R^c$ and $R^d$ can both be hydrogen or each common substitutients such as: $C_{1-12}$ alkyl; $C_{2-12}$ alkenyl; $C_{3-12}$ cycloalkyl; $C_{2-6}$ heterocyclyl; $C_{6-12}$ aryl optionally substituted with 1 or more halo, hydroxyl, $C_{1-6}$ alkyl and/or $C_{1-6}$ alkoxyl; and $C_{4-12}$ heteroaryl optionally substituted with 1 or more halo, hydroxyl, $C_{1-6}$ alkyl and/or $C_{1-6}$ alkoxyl. Alternatively, $R^c$ and $R^d$ together with the nitrogen they are attached to can form a ring structure, such as a $C_{4-14}$ heteroaryl optionally substituted with 1 or more halo, hydroxyl, $C_{1-6}$ alkyl and/or $C_{1-6}$ alkoxyl.

$R^{3a}$ may be hydrogen, halo (e.g., bromo), hydroxyl, $C_{1-3}$ alkoxyl (e.g., methoxyl), cyano, carboxyl, or formamide. In certain embodiments, $R^{3a}$ is hydrogen. In some embodiments, $R^{3a}$ is bromo.

$R^{4a}$ may be hydrogen, halo (e.g., bromo), hydroxyl, $C_{1-3}$ alkoxyl (e.g., methoxyl), cyano, carboxyl, or formamide. In certain embodiments, $R^{4a}$ is hydrogen. In some embodiments, $R^{4a}$ is bromo.

In certain embodiments, the presently disclosed embodiments include a compound or pharmaceutically acceptable salt thereof, for promoting neurogenesis and/or reducing neuronal cell death, the compound having formula (III):

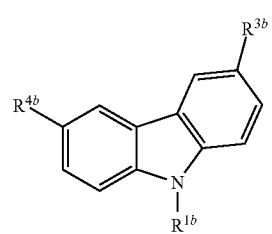

(III)

wherein $R^{1b}$ is selected from the group consisting of: hydrogen; $C_{1-6}$ alkyl optionally substituted with 1 or more halo, hydroxyl, cyano and/or azide; —CH($R^5$)—C(O)—$Z^{1b}$; and —CH$_2$—C($R^{41}$)($R^{42}$)—CH$_2$—$Z^{2b}$;

wherein $R^5$ is hydrogen or $C_{1-3}$ alkyl;

wherein one of $R^{41}$ and $R^{42}$ is hydroxyl or halo and the other is hydrogen;

wherein $Z^{1b}$ is selected from the group consisting of: hydroxyl; $C_{1-6}$ alkoxyl; and amine optionally substituted with a hydroxyl, $C_{1-12}$ alkyl sulfonyl optionally substituted with 1-6 halo, $C_{6-12}$ aryl sulfonyl optionally substituted with 1-6 halo, $C_{4-12}$ heteroaryl sulfonyl optionally substituted with 1-6 halo, $C_{2-12}$ alkyl carbonyl optionally substituted with 1-6 halo, and/or $C_{2-12}$ carboxyalkyl optionally substituted with 1-6 halo;

wherein $Z^{2b}$ is selected from the group consisting of: $C_{1-3}$ alkyl, azide, and N($R^6$)($R^7$);

wherein $R^6$ and $R^7$ are each independently selected from the group consisting of: hydrogen; carboxamide optionally substituted with 1 or more $C_{1-6}$ alkyl, $C_{6-12}$ aryl and/or $C_{4-12}$ heteroaryl; $C_{6-12}$ aryl optionally substituted with 1 or more halo, hydroxyl, $C_{1-6}$ alkyl and/or $C_{1-6}$ alkoxyl; $C_{1-12}$ alkyl sulfonyl optionally substituted with 1-6 halo; $C_{6-12}$ aryl sulfonyl optionally substituted with 1-6 halo; and $C_{4-12}$ heteroaryl sulfonyl optionally substituted with 1-6 halo; wherein no more than one of $R^6$ and $R^7$ is hydrogen; and wherein $R^{3b}$ and $R^{4b}$ are each independently selected from the group consisting of: hydrogen, halo, hydroxyl, $C_{1-3}$ alkoxyl, cyano, carboxyl, and formamide.

In some embodiments, one or more of the following definitions apply:

(5) when $R^{1b}$ is optionally substituted $C_{1-6}$ alkyl, Rib is selected from unsubstituted $C_{1-6}$ alkyl or $C_{3-6}$ alkyl substituted with 1 hydroxyl or $C_{1-6}$ alkyl substituted with 1 cyano;

(6) when Rib unsubstituted $C_{1-6}$ alkyl, $R^{1b}$ is unsubstituted $C_{2-6}$ alkyl;

(7) when $R^5$ is hydrogen, $Z^{1b}$ is amine optionally substituted with a hydroxyl, $C_{1-12}$ alkyl sulfonyl optionally substituted with 1-6 halo, $C_{6-12}$ aryl sulfonyl optionally substituted with 1-6 halo, $C_{4-12}$ heteroaryl sulfonyl optionally substituted with 1-6 halo, $C_{2-12}$ alkyl carbonyl optionally substituted with 1-6 halo, and/or $C_{2-12}$ carboxyalkyl optionally substituted with 1-6 halo; and/or (8) $Z^{2b}$ is azide or N($R^6$)($R^7$).

For example, $R^{1b}$ may be hydrogen. $R^{1b}$ may also be $C_{1-6}$ alkyl optionally substituted with 1 or more halo, hydroxyl, cyano and/or azide, such as unsubstituted $C_{1-6}$ alkyl (e.g., methyl, ethyl, n-propyl, isopropyl, or tert-butyl) or $C_{3-6}$ alkyl substituted with 1 hydroxyl (e.g., at the beta-carbon) or $C_{1-6}$ alkyl substituted with 1 cyano. $R^{1b}$ may also be —CH($R^5$)—C(O)—$Z^{1b}$ or —CH$_2$—C($R^{41}$)($R^{42}$)—CH$_2$—$Z^{2b}$.

$R^5$ can be hydrogen or $C_{1-3}$ alkyl (e.g., methyl). $Z^{1b}$ can be hydroxyl or $C_{1-6}$ alkoxyl. $Z^{1b}$ can also be amine optionally substituted with 1 hydroxyl, or amine optionally substituted with $C_{1-12}$ alkyl sulfonyl, $C_{6-12}$ aryl sulfonyl, $C_{4-12}$ heteroaryl sulfonyl, $C_{2-12}$ alkyl carbonyl, or $C_{2-12}$ carboxyalkyl (e.g., —CH$_2$C(O)OH). The $C_{1-12}$ alkyl sulfonyl, $C_{6-12}$ aryl sulfonyl, $C_{4-12}$ heteroaryl sulfonyl, $C_{2-12}$ alkyl carbonyl, and $C_{2-12}$ carboxyalkyl groups can contain one or more common substitutients such as alkyl, halo, hydroxyl, alkoxyl, aryl and/or heteroaryl.

One of $R^{41}$ and $R^{42}$ can be hydroxyl or halo (e.g., fluoro) and the other of $R^{41}$ and $R^{42}$ can be hydrogen. Alternatively, both $R^{41}$ and $R^{42}$ can be hydrogen. $Z^{2b}$ can be $C_{1-3}$ alkyl. $Z^{2b}$ can also be azide or N($R^6$)($R^7$). $R^6$ and $R^7$ can both be hydrogen. Alternatively, only one of $R^6$ and $R^7$ is hydrogen, or none of $R^6$ and $R^7$ is hydrogen. $R^6$ and $R^7$ can also be carboxamide optionally substituted with 1 or more $C_{1-6}$ alkyl, $C_{6-12}$ aryl and/or $C_{4-12}$ heteroaryl; $C_{6-12}$ aryl optionally substituted with 1 or more halo, hydroxyl, $C_{1-6}$ alkyl and/or $C_{1-6}$ alkoxyl; $C_{1-12}$ alkyl sulfonyl optionally substituted with 1-6 halo; $C_{6-12}$ aryl sulfonyl optionally substituted with 1-6 halo; or $C_{4-12}$ heteroaryl sulfonyl optionally substituted with 1-6 halo.

$R^{3b}$ may be hydrogen, halo (e.g., bromo), hydroxyl, $C_{1-3}$ alkoxyl (e.g., methoxyl), cyano, carboxyl, or formamide. In certain embodiments, $R^{3b}$ is hydrogen. In some embodiments, $R^{3b}$ is bromo.

$R^{4b}$ may be hydrogen, halo (e.g., bromo), hydroxyl, $C_{1-3}$ alkoxyl (e.g., methoxyl), cyano, carboxyl, or formamide. In certain embodiments, $R^{4b}$ is hydrogen. In some embodiments, $R^{4b}$ is bromo.

For example, both $R^{3b}$ and $R^{4b}$ are hydrogen. Both $R^{3b}$ and $R^{4b}$ can be bromo.

In certain embodiments, the presently disclosed embodiments include a compound or pharmaceutically acceptable salt thereof, for promoting neurogenesis and/or reducing neuronal cell death, the compound having formula (IV):

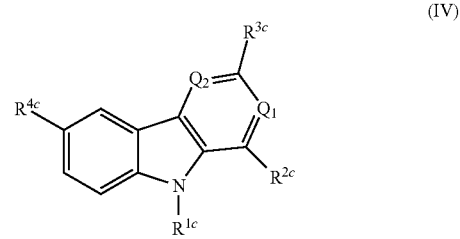

(IV)

wherein:

$R^{1c}$ is selected from the group consisting of: hydrogen, $C_{1-6}$ alkyl, $C_{1-6}$carboxyalkyl, $C_{1-12}$ alkyl sulfonyl optionally substituted with 1-6 halo, $C_{6-12}$ aryl sulfonyl optionally substituted with 1-6 halo and $C_{4-12}$ heteroaryl sulfonyl optionally substituted with 1-6 halo;

$R^{2c}$ is selected from the group consisting of: hydrogen; hydroxyl; cyano; halo; amine optionally substituted with 1 or more $C_{1-6}$ alkyl, $C_{2-6}$ alkenyl, $C_{3-6}$ cycloalkyl, aryl, and/or heteroaryl; and $C_{1-12}$ alkoxyl;

$R^{3c}$ is selected from the group consisting of: carboxyl; $C_{1-6}$ alkoxycarbonyl; hydroxyl; $C_{1-12}$ alkoxyl; cyano; halo; and amine optionally substituted with 1 or more $C_{1-6}$ alkyl, $C_{2-6}$ alkenyl, $C_{3-6}$ cycloalkyl, aryl, and/or heteroaryl;

$R^{4c}$ is selected from the group consisting of: hydrogen, halo, hydroxyl, and $C_{1-3}$ alkoxyl; and one or both of $Q_1$ and $Q_2$ are nitrogen.

In some embodiments, one or more of the following definitions apply:

(3) $R^{2c}$ is hydrogen; hydroxyl; or $C_{1-12}$ alkoxyl; and/or (4) $R^{3c}$ is carboxyl; $C_{1-6}$ alkoxycarbonyl; hydroxyl; or amine substituted with 1-2 $C_{1-6}$ alkyl.

For example, $R^{1c}$ can be hydrogen. $R^{1c}$ can also be $C_{1-6}$ alkyl or $C_{2-6}$ carboxyalkyl (e.g., —CH$_2$C(O)OH). $R^{1c}$ can also be $C_{1-12}$ alkyl sulfonyl optionally substituted with 1-6 halo or $C_{6-12}$ aryl sulfonyl (e.g., —S(O)$_2$Ph) optionally substituted with 1-6 alkyl, substituted alkyl (e.g., $CF_3$) and/or halo. $R^{1c}$ can also be $C_{4-12}$ heteroaryl sulfonyl optionally substituted with 1-6 alkyl, substituted alkyl (e.g., $CF_3$) and/or halo.

$R^{2c}$ can be hydrogen or hydroxyl. $R^{2c}$ can also be cyano; halo; or amine optionally substituted with 1 or more $C_{1-6}$ alkyl, $C_{2-6}$ alkenyl, $C_{3-6}$ cycloalkyl, aryl, and/or heteroaryl. $R^{2c}$ can also be $C_{1-12}$ alkoxyl.

$R^{3c}$ can be carboxyl or $C_{1-6}$ alkoxycarbonyl (e.g., —C(O)OCH$_3$ or —C(O)OCH$_2$CH$_3$). $R^{3c}$ can also be hydroxyl. $R^{3c}$ can also be $C_{1-12}$ alkoxyl; cyano; or halo (e.g., bromo). $R^{3c}$ can also be amine optionally substituted with 1 or more $C_{1-6}$ alkyl, $C_{2-6}$ alkenyl, $C_{3-6}$ cycloalkyl, aryl, and/or heteroaryl, such as $N(CH_3)_2$.

$R^{4c}$ can be hydrogen or halo (e.g., bromo). $R^{4c}$ can also be hydroxyl or and $C_{1-3}$ alkoxyl.

$Q_1$ and $Q_2$ can both be nitrogen. Alternatively, one of $Q_1$ and $Q_2$ is nitrogen and the other of $Q_1$ and $Q_2$ is carbon. In some embodiments, when both $Q_1$ and $Q_2$ are be nitrogen and both $R^{2c}$ and $R^{3c}$ are hydroxyl, the corresponding ring structure is typically represented by:

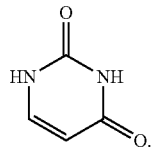

In certain embodiments, the presently disclosed embodiments include a compound or pharmaceutically acceptable salt thereof, for promoting neurogenesis and/or reducing neuronal cell death, the compound having formula (V):

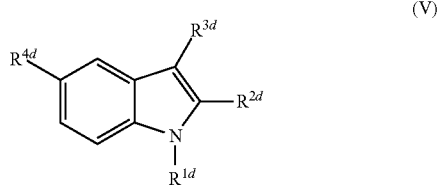

(V)

wherein $R^{1d}$ is selected from the group consisting of: hydrogen and $CH_2$—$C(R^{41})(R^{42})$—$CH_2$—$N(R^6)(R^7)$;
wherein one of $R^{41}$ and $R^{42}$ is hydroxyl or halo and the other is hydrogen; and
wherein $R^6$ and $R^7$ are each independently selected from the group consisting of: hydrogen; $C_{6-12}$ aryl optionally substituted with 1 or more halo, hydroxyl, $C_{1-6}$ alkyl and/or $C_{1-6}$ alkoxyl; and $C_{4-12}$ heteroaryl optionally substituted with 1 or more halo, hydroxyl, $C_{1-6}$ alkyl and/or $C_{1-6}$ alkoxyl;
wherein $R^{2d}$ is selected from the group consisting of: halo, hydroxyl, $C_{1-12}$ alkoxyl, cyano, aryl, and heteroaryl;
wherein $R^{3d}$ is selected from the group consisting of: hydrogen and amine optionally substituted with 1 or more $C_{1-6}$ alkyl, $C_{2-6}$ alkenyl, $C_{3-6}$ cycloalkyl, $C_{2-6}$ heterocyclyl, aryl, and/or heteroaryl; and
wherein $R^{4d}$ is selected from the group consisting of: hydrogen, halo, hydroxyl, and $C_{1-3}$ alkoxyl.

In some embodiments, $R^{2d}$ is cyano, and/or $R^{4d}$ is hydrogen, bromo or methoxy.

For example, $R^{1d}$ can be hydrogen. $R^{1d}$ can also be $CH_2$—$C(R^{41})(R^{42})$—$CH_2$—$N(R^6)(R^7)$. One of $R^{41}$ and $R^{42}$ can be hydroxyl and the other is hydrogen. One of $R^{41}$ and $R^{42}$ can be halo (e.g., fluoro) and the other is hydrogen. Alternatively, both $R^{41}$ and $R^{42}$ can be hydrogen. $R^6$ and $R^7$ can both be hydrogen. Alternatively, one or both of $R^6$ and $R^7$ can be $C_{6-12}$ aryl optionally substituted with 1 or more halo, hydroxyl, $C_{1-6}$ alkyl and/or $C_{1-6}$ alkoxyl; or $C_{4-12}$ heteroaryl optionally substituted with 1 or more halo, hydroxyl, $C_{1-6}$ alkyl and/or $C_{1-6}$ alkoxyl.

$R^{2d}$ can be halo, hydroxyl, or $C_{1-12}$ alkoxyl. $R^{2d}$ can also be cyano. $R^{2d}$ can also be aryl (e.g., $C_{6-12}$) or heteroaryl (e.g., $C_{4-12}$).

$R^{3d}$ can be hydrogen. $R^{3d}$ can also be amine optionally substituted with 1 or more $C_{1-6}$ alkyl, $C_{2-6}$ alkenyl, $C_{3-6}$ cycloalkyl, $C_{2-6}$ heterocyclyl, aryl (e.g., $C_{6-12}$), and/or heteroaryl (e.g., $C_{4-12}$).

$R^{4d}$ can be hydrogen, halo (e.g., bromo), hydroxyl, or $C_{1-3}$ alkoxyl (e.g., methoxyl).

Compounds or salts thereof having any combinations of the above definitions of the various groups are all included in the presently disclosed embodiments.

All publications and patents mentioned herein are hereby incorporated by reference in their entirety as if each individual publication or patent was specifically and individually indicated to be incorporated by reference.

What is claimed is:

1. A method of treating a neuropsychiatric or neurodegenerative disease, disorder, or condition, the method comprising administering to a subject in need thereof an effective amount of a compound having formula (III), or a pharmaceutically acceptable salt thereof:

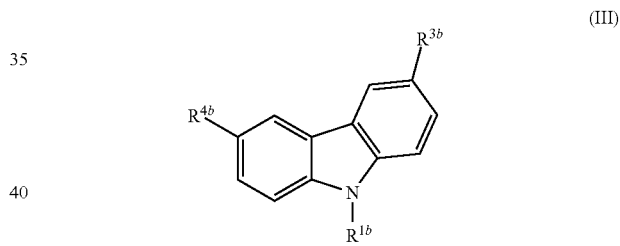

(III)

wherein $R^{1b}$ is selected from the group consisting of: hydrogen; $C_{1-6}$ alkyl optionally substituted with one or more halo, hydroxyl, cyano and/or azide; —CH($R^5$)—C(O)—$Z^{1b}$; and —$CH_2$—$C(R^{41})(R^{42})$—$CH_2$—$Z^{2b}$;
wherein $R^5$ is hydrogen or $C_{1-3}$ alkyl;
wherein $Z^{1b}$ is selected from the group consisting of: hydroxyl; $C_{1-6}$ alkoxyl; and amine optionally substituted with a hydroxyl, $C_{1-12}$ alkyl sulfonyl, $C_{6-12}$ aryl sulfonyl, $C_{4-12}$ heteroaryl sulfonyl, $C_{2-12}$ alkyl carbonyl, and/or $C_{2-12}$ carboxyalkyl; wherein each of the $C_{1-12}$ alkyl sulfonyl, $C_{6-12}$ aryl sulfonyl, $C_{4-12}$ heteroaryl sulfonyl, $C_{2-12}$ alkyl carbonyl, and $C_{2-12}$ carboxyalkyl is optionally substituted with 1-6 halo, hydroxyl, $C_{1-6}$ alkyl, and/or $C_{1-6}$ alkoxyl;
wherein one of $R^{41}$ and $R^{42}$ is hydroxyl or halo and the other is hydrogen;
wherein $Z^{2b}$ is selected from the group consisting of: $C_{1-3}$ alkyl, azide, and $N(R^6)(R^7)$;
wherein $R^6$ and $R^7$ are each independently selected from the group consisting of:
hydrogen; carboxamide optionally substituted with 1 or more $C_{1-6}$ alkyl, $C_{6-12}$ aryl and/or $C_{4-12}$ heteroaryl; $C_{1-12}$ alkyl sulfonyl; $C_{6-12}$ aryl sulfonyl; and $C_{4-12}$ heteroaryl sulfonyl; wherein each of the $C_{1-12}$ alkyl sulfonyl, $C_{6-12}$ aryl sulfonyl, and $C_{4-12}$ heteroaryl sulfonyl is optionally substituted with 1-6 halo; wherein no more than one of $R^6$ and $R^7$ is hydrogen; or wherein one of $R^6$ and $R^7$ is $C_{6-12}$ aryl optionally substituted with 1 or more halo, hydroxyl, $C_{1-6}$ alkyl and/or $C_{1-6}$ alkoxyl; and the other of $R^6$ and $R^7$ is $C_{1-12}$ alkyl sulfonyl, $C_{6-12}$ aryl sulfonyl, or $C_{4-12}$ heteroaryl sulfonyl, wherein each of the $C_{1-12}$ alkyl sulfonyl, $C_{6-12}$ aryl sulfonyl, and $C_{4-12}$ heteroaryl sulfonyl is optionally substituted with 1-6 halo; and wherein $R^{3b}$ and $R^{4b}$ are each independently selected from the group consisting of: hydrogen, halo, hydroxyl, $C_{1-3}$ alkoxyl, cyano, carboxyl, and formamide; wherein the disease, disorder, or condition is selected from one or more of schizophrenia, major depression, bipolar disorder, normal aging, epilepsy, traumatic brain injury, post-traumatic stress disorder, Parkinson's disease, Alzheimer's disease, Down syndrome, spinocerebellar ataxia, amyotrophic lateral sclerosis, Huntington's disease, stroke, radiation therapy, chronic stress, abuse of neuroactive drugs, retinal degeneration, spinal cord injury, peripheral nerve injury, physiological weight loss, and cognitive decline associated with normal aging, radiation therapy, and chemotherapy.

2. The method of claim 1, wherein $R^{1b}$ is optionally substituted $C_{1-6}$ alkyl.

3. The method of claim 2, wherein $R^{1b}$ is selected from unsubstituted $C_{1-6}$ alkyl or $C_{3-6}$ alkyl substituted with one hydroxyl or $C_{1-6}$ alkyl substituted with one cyano.

4. The method of claim 3, wherein $R^{1b}$ is unsubstituted $C_{1-6}$ alkyl.

5. The method of claim 4, wherein $R^{1b}$ is unsubstituted $C_{2-6}$ alkyl.

6. The method of claim 3, wherein $R^{1b}$ is $C_{3-6}$ alkyl substituted with one hydroxyl.

7. The method of claim 3, wherein $R^{1b}$ is $C_{1-6}$ alkyl substituted with one cyano.

8. The method of claim 1, wherein $R^{1b}$ is —CH($R^5$)—C(O)—$Z^{1b}$.

9. The method of claim 8, wherein $R^5$ is hydrogen.

10. The method of claim 9, wherein $Z^{1b}$ is amine optionally substituted with a hydroxyl, $C_{1-12}$ alkyl sulfonyl, $C_{6-12}$ aryl sulfonyl, $C_{4-12}$ heteroaryl sulfonyl, $C_{2-12}$ alkyl carbonyl, and/or $C_{2-12}$ carboxyalkyl; wherein each of the $C_{1-12}$ alkyl sulfonyl, $C_{6-12}$ aryl sulfonyl, $C_{4-12}$ heteroaryl sulfonyl, $C_{2-12}$ alkyl carbonyl, and $C_{2-12}$ carboxyalkyl is optionally substituted with 1-6 halo, hydroxyl, $C_{1-6}$ alkyl, and/or $C_{1-6}$ alkoxyl.

11. The method of claim 10, wherein $Z^{1b}$ is $C_{6-12}$ aryl sulfonyl optionally substituted with 1-6 halo, hydroxyl, $C_{1-6}$alkyl, and/or $C_{1-6}$alkoxyl.

12. The method of claim 11, wherein the compound is 2-(3,6-dibromo-9H-carbazol-9-yl)-N-(phenylsulfonyl)acetamide.

13. The method of claim 1, wherein $R^{1b}$ is —CH$_2$—C($R^{41}$)($R^{42}$)—CH$_2$—$Z^{2b}$.

14. The method of claim 12, wherein $Z^{2b}$ is azide or N($R^6$)($R^7$).

* * * * *

UNITED STATES PATENT AND TRADEMARK OFFICE
CERTIFICATE OF CORRECTION

PATENT NO. : 9,701,676 B2  
APPLICATION NO. : 13/974642  
DATED : July 11, 2017  
INVENTOR(S) : Steven L. McKnight et al.

Page 1 of 1

It is certified that error appears in the above-identified patent and that said Letters Patent is hereby corrected as shown below:

In the Specification

In Column 1, Lines 14-18 below the STATEMENT REGARDING FEDERALLY SPONSORED RESEARCH, delete:
"This invention was made with government support under Grant Numbers 5DPIOD00027605, 5R37MH05938809, and 1RO1MH087986, which were awarded by the National Institute of Health; the Government has certain rights in the invention."

And add:
--This invention was made with government support under grant numbers CA095471 and MH087986 awarded by The National Institutes of Health. The government has certain rights in the invention.--

Signed and Sealed this
Thirtieth Day of June, 2020

Andrei Iancu
*Director of the United States Patent and Trademark Office*